(12) United States Patent
Negre et al.

(10) Patent No.: US 10,280,435 B2
(45) Date of Patent: May 7, 2019

(54) GENE THERAPY METHODS

(71) Applicant: bluebird bio, Inc., Cambridge, MA (US)

(72) Inventors: Olivier Negre, Orsay (FR); Emmanuel Payen, Ville d'Avray (FR); Philippe Leboulch, Bangkok (TH); Yves Beuzard, Paris (FR)

(73) Assignee: bluebird bio, Inc., Cambridge, MA (US)

(*) Notice: Subject to any disclaimer, the term of this patent is extended or adjusted under 35 U.S.C. 154(b) by 0 days.

(21) Appl. No.: 15/728,381

(22) Filed: Oct. 9, 2017

(65) Prior Publication Data

US 2018/0201952 A1    Jul. 19, 2018

Related U.S. Application Data

(63) Continuation of application No. 14/346,647, filed as application No. PCT/US2011/053096 on Sep. 23, 2011, now Pat. No. 9,783,822.

(51) Int. Cl.
| | |
|---|---|
| *C12N 15/85* | (2006.01) |
| *A61K 35/28* | (2015.01) |
| *A61K 35/18* | (2015.01) |
| *A61K 38/18* | (2006.01) |
| *A61K 48/00* | (2006.01) |
| *C07K 14/71* | (2006.01) |
| *C07K 14/805* | (2006.01) |
| *C12N 15/86* | (2006.01) |
| *A61K 35/12* | (2015.01) |

(52) U.S. Cl.
CPC .............. *C12N 15/85* (2013.01); *A61K 35/18* (2013.01); *A61K 35/28* (2013.01); *A61K 38/1816* (2013.01); *A61K 48/00* (2013.01); *A61K 2035/124* (2013.01); *C07K 14/71* (2013.01); *C07K 14/805* (2013.01); *C12N 15/86* (2013.01); *C12N 2740/16043* (2013.01); *C12N 2800/22* (2013.01); *C12N 2830/008* (2013.01); *C12N 2830/15* (2013.01); *C12N 2830/20* (2013.01); *C12N 2830/40* (2013.01)

(58) Field of Classification Search
None
See application file for complete search history.

(56) References Cited

U.S. PATENT DOCUMENTS

| | | | |
|---|---|---|---|
| 5,399,363 A | 3/1995 | Liversidge et al. | |
| 5,460,964 A | 10/1995 | McGlave et al. | |
| 5,466,468 A | 11/1995 | Schneider et al. | |
| 5,543,158 A | 8/1996 | Gref et al. | |
| 5,635,387 A | 6/1997 | Fei et al. | |
| 5,641,515 A | 6/1997 | Ramtoola | |
| 5,677,136 A | 10/1997 | Simmons et al. | |
| 5,716,827 A | 2/1998 | Tsukamoto et al. | |
| 5,750,397 A | 5/1998 | Tsukamoto et al. | |
| 5,759,793 A | 6/1998 | Schwartz et al. | |
| 5,861,488 A | 1/1999 | Leboulch et al. | |
| 5,864,029 A | 1/1999 | Townes et al. | |
| 5,877,288 A | 3/1999 | Townes et al. | |
| 5,994,136 A | 11/1999 | Naldini et al. | |
| 6,013,516 A | 1/2000 | Verma et al. | |
| 6,022,535 A | 2/2000 | Bauer et al. | |
| 6,051,402 A | 4/2000 | Leboulch et al. | |
| 6,670,323 B1 | 12/2003 | Looker et al. | |
| 6,682,907 B1 | 1/2004 | Charneau et al. | |
| 7,901,671 B2 | 3/2011 | Leboulch et al. | |
| 9,783,822 B2 | 10/2017 | Negre et al. | |
| 2002/0120098 A1 | 8/2002 | Bell et al. | |
| 2006/0057725 A1 | 3/2006 | Leboulch et al. | |
| 2009/0274671 A1 | 11/2009 | Sadelain et al. | |
| 2015/0203868 A1 | 7/2015 | Negre et al. | |

FOREIGN PATENT DOCUMENTS

| | | |
|---|---|---|
| WO | WO 2001/036489 A2 | 5/2001 |
| WO | WO 2005/021579 A2 | 3/2005 |
| WO | WO 2006/120030 A1 | 11/2006 |
| WO | WO 2008/065372 A2 | 6/2008 |
| WO | WO 2013/043196 A1 | 3/2013 |

OTHER PUBLICATIONS

Alt and Caselmann, "Liver-directed gene therapy: molecular tools and current preclinical and clinical studies", J Hepatol. (1995), 23(6): 746-758.
Bell, A.C. et al., "The protein CTCF is required for the enhancer blocking activity of vertebrate insulators", Cell. (1999), 98(3):387-96.
Bradley, M.B. et al., "Correction of phenotype in a thalassemia mouse model using a nonmyeloablative marrow transplantation regimen", Biol Blood Marrow Transplant (2002), 8(8): 453-461.
Brody and Crystal, "Adenovirus-mediated in vivo gene transfer", Ann NY Acad Sci. (1994), 716: 90-101; discussion 101-3.
Burgess-Belisse, B. et al., "The insulation of genes from external enhancers and silencing chromatin", Proc Nati Acad Sci USA (2002). 99(Suppl 4):16433-16437.
Beard, B.C. et al., "Efficient and stable MGMT-mediated selection of long-term repopulating stem cells in nonhuman primates", J Clin Invest. (2010), 120(7): 2345-2354.
Cavazzana-Calvo, M. et al., "Transfusion independence and HMGA2 activation after gene therapy of human β-thalassaemia", Nature (2010), 467(7313): 318-322.
Chang, A.H., et al., "Erythroid-specific Human Factor IX Delivery From In Vivo Selected Hematopoietic Stem Cells Following Nonmyeloablative Conditioning in Hemophilia B Mice", Molecular Therapy (2008), 16(10): 1745-1752.

(Continued)

*Primary Examiner* — Robert M Kelly
(74) *Attorney, Agent, or Firm* — Cooley LLP

(57) ABSTRACT

The present invention generally provides improved gene therapy vectors, cell-based compositions, and methods of using the same in methods of gene therapy. The present invention further provides improved gene therapy compositions for expanding hematopoietic cells and related methods for treatment of diseases, disorders, and conditions of the hematopoietic system such as thalassemias and anemias.

16 Claims, 15 Drawing Sheets

Specification includes a Sequence Listing.

(56) References Cited

OTHER PUBLICATIONS

Chung, J.H. et al., "A 5' element of the chicken beta-globin domain serves as an insulator in human erythroid cells and protects against position effect in Drosophila", Cell (1993), 74(3): 505-514.
Chung, J.H. et al., "Characterization of the chicken beta-globin insulator", Proc Natl Acad Sci USA (1997), 94(2): 575-580.
Clever, J. et al., "RNA Secondary Structure and Binding Sites for gag Gene Products in the 59 Packaging Signal of Human Immunodeficiency Virus Type 1", J. of Virology (1995), 69(4): 2101-2109.
Cornetta, K. et al., "A pilot study of dose-intensified procarbazine, CCNU, vincristine for poor prognosis brain tumors utilizing fibronectin-assisted, retroviral-mediated modification of CD34+ peripheral blood cells with O6-methylguanine DNA methyltransferase", Cancer Gene Therapy (2006), 13: 886-895.
Cullen, B.R., "Human immunodeficiency virus as a prototypic complex retrovirus", Journal of Virology (1991), 65(3): 1053-1056.
Cullen and Greene, "Regulatory pathways governing HIV-1 replication", Cell (1989), 58: 423-426.
Damen, J.E. et al., "Tyrosine 343 in the erythropoietin receptor positively regulates erythropoietin-induced cell proliferation and Stat5 activation", EMBO J. (1995), 14(22): 5557-5568.
Dull et al., "A third-generation lentivirus vector with a conditional packaging system", Journal of Virology (1998), 72(11): 8463-8471.
Dunbar, C.E. et al., "Retroviral Transfer of the Glucocerebrosidase Gene into CD34+ Cells from Patients with Gaucher Disease: In Vivo Detection of Transduced Cells without Myeloablation", Human Gene Therapy (1998), 9(17): 2629-2640.
Eschbach, J.W. et al., "Anemia of end-stage renal disease (ESRD)", Kidney Int. (1985), 28(1): 1-5.
Ferry and Heard, "Liver-directed gene transfer vectors", Hum Gene Ther. (1998), 9(14): 1975-1981.
Graber, S.E. "Erythropoietin and the control of red cell production", Annu Rev Med. (1978), 29: 51-66.
Huang and Yen, "Role of the hepatitis B virus posttranscriptional regulatory element in export of intronless transcripts", Mol. Cell. Biol. (1995), 15(7): 3864-3869.
Imren, S. et al., "Permanent and panerythroid correction of murine β thalassemia by multiple lentiviral integration in hematopoietic stem cells", Proc Natl Acad Sci USA (2002), 99(22): 14380-14385.
Kay, M.A. "Adenoviral vectors for hepatic gene transfer in animals", Chest (1997),111(6 Suppl): 138S-142S.
Kirby et al., "Hematopoietic stem cells with controllable tEpoR transgenes have a competitive advantage in bone marrow transplantation", Blood (2000), 95(12): 3710-3715.
Kirby et al., "Proliferation of multipotent hematopoietic cells controlled by a truncated erythropoietin receptor transgene", Proc Natl Acad Sci USA (1996), 93: 9402-9407.
Kirito, K. et al., "A distinct function of STAT proteins in erythropoietin signal transduction", J Biol Chem. (1997), 272(26): 16507-16513.
Kittler, E.L.W. et al., "Cytokine-facilitated transduction leads to low-level engraftment in nonablated hosts", Blood (1997), 90(2): 865-872.
Lee, H.C. et al., "Remission in models of type 1 diabetes by gene therapy using a single-chain insulin analogue", Nature (2000), 408(6811): 483-488.
Levasseur, D.N. et al., "Correction of a mouse model of sickle cell disease: lentiviral/antisickling betaglobin gene transduction of unmobilized, purified hematopoietic stem cells", Blood (2003), 102(13): 4312-4319.
Liu and Mertz, "HnRNP L binds a cis-acting RNA sequence element that enables intron-dependent gene expression", Genes & Dev. (1995), 9: 1766-1780.
Malik, P. et al., "Successful correction of the human Cooley's anemia β-thalassemia major phenotype using a lentiviral vector flanked by the chicken hypersensitive site 4 chromatin insulator", Annals of the New York Academy of Sciences (2005), Annals of the New York Academy of Sciences vol. 1054, Cooley's Anemia: Eighth Symposium pp. 238-249, Nov. 2005.

May, C. et al., "Therapeutic haemoglobin synthesis in β-thalassaemic mice expressing lentivirus-encoded human β-globin", Nature (2000), 406(6791): 82-86.
Milsom, M.D. et al., "Reciprocal relationship between $O^6$-Methylguanine-DNA methyltransferase P140K expression level and chemoprotection of hematopoietic stem cells", Cancer Res. (2008), 68(15): 6171-6180.
Miyoshi, H., "Transduction of hematopoietic stem cells by lentiviral vectors", Virus (2002), 52(2): 225-231 (and English translation of Summary/Abstract).
Moreau-Gaudry et al., "High-level erythroid-specific gene expression in primary human and murine hematopoietic cells with self-inactivating lentiviral vectors." Blood (2001); 98(9): 2664-2672.
Nakamura et al., "Role of a truncated erythropoietin receptor for erythroid differentiation", Biochem Biophys Res Commun. (1996), 218(1): 205-209.
Naldini L. et al., "Efficient transfer, integration, and sustained long-term expression of the transgene in adult rat brains injected with a lentiviral vector", *Proc Natl Acad Sci USA* (1996), 93(21): 11382-11388.
Naldini, L. et al., "In vivo gene delivery and stable transduction of nondividing cells by a lentiviral vector", Science (1996), 272(5259): 263-267.
Naldini, L., "Lentiviruses as gene transfer agents for delivery to non-dividing cells", *Curr Opin Biotechnol.* (1998), 5: 457-63.
Negre et al., "Correction of murine β-thalassemia after minimal lentiviral gene transfer and homeostatic in vivo erythroid expansion." Blood (2011); 117(20): 5321-5331.
Oka, K. et al., "Recent advances in liver-directed gene therapy: implications for the treatment of dyslipidemia", Curr Opin Lipidol. (2000), 11(2): 179-186.
Pawliuk, R. et al., "Correction of sickle cell disease in transgenic mouse models by gene therapy", Science (2001), 294(5550): 2368-2371 (and Supplementary Material).
PCT Application No. PCT/US2011/053096, International Search Report and Written Opinion dated Jul. 31, 2012.
PCT Application No. PCT/US2011/053096, International Preliminary Report on Patentability dated Mar. 25, 2014.
Peters, S.O. et al., "Ex vivo expansion of murine marrow cells with interleukin-3 (IL-3), IL-6, IL-11, and stem cell factor leads to impaired engraftment in irradiated hosts", Blood (1996), 87(1): 30-37.
Ramshaw, H.S. et al., "Engraftment of bone marrow cells into normal unprepared hosts: effects of 5-fluorouracil and cell cycle status", Blood (1995), 86(3): 924-929.
Ronen, K. "Distribution of lentiviral vector integration sites in mice following therapeutic gene transfer to treat β-thalassemia", Molecular Therapy (2011), 19(7):1273-86.
Santoni De Sio and Naldini, "Short-term culture of human CD34+ cells for lentiviral gene transfer", Methods Mol Biol. (2009), 506: 59-70.
Roberts, C. et al., "Murine and math models for the level of stable mixed chimerism to cure β-thalassemia by nonmyeloablative bone marrow transplantation", Ann N Y Acad Sci. (2005), 1054: 423-428.
Shiratori, Y. et al., "Strategy of liver-directed gene therapy: present status and future prospects", Liver (1999), 19(4): 265-274.
Smith-Arica, J.R. et al., "Gene therapy: recombinant adeno-associated virus vectors", Curr Cardiol Rep. (2001), 3(1): 43-49.
Strayer, D.S. "Viral gene delivery", Expert Opin Investig Drugs (1999), 8(12): 2159-2172.
Takenaga, M. et al., "Microparticle resins as a potential nasal drug delivery system for insulin", Journal of Controlled Release (1998), 52(Issues 1-2): 81-87.
Thule, P.M. et al., "Regulated hepatic insulin gene therapy of STZ-diabetic rats", Gene Ther. (2000), 7(20):1744-52.
Torti, M. et al., "Erythropoietin induces $p21^{ras}$ activation and p120GAP tyrosine phosphorylation in human erythroleukemia cells", J. Biol. Chem. (1992), 267: 8293-8298.
Urbinati et al., "Competitive engraftment of hematopoietic stem cells genetically modified with a truncated erythropoietin receptor." Human Gene Therapy (2005); 16(5): 594-608.

(56) References Cited

OTHER PUBLICATIONS

Witthuhn, B.A. et al., "JAK2 associates with the erythropoietin receptor and is tyrosine phosphorylated and activated following stimulation with erythropoietin", Cell (1993), 74(2): 227-236.

Yang, N.S., "Gene transfer into mammalian somatic cells in vivo", Crit Rev Biotechnol. (1992), 12(4): 335-356.

Zennou, V. et al., "HIV-1 genome nuclear import is mediated by a central DNA flap", Cell (2000), 101(2): 173-185.

Zhan, H.C. et al., "Insulator: from chromatin domain boundary to gene regulation", Hum Genet. (2001), 109(5): 471-478.

Zufferey, R. et al., "Woodchuck hepatitis virus posttranscriptional regulatory element enhances expression of transgenes delivered by retroviral vectors", J Virol. (1999), 73(4): 2886-2892.

Zufferey, et al., "Multiply attenuated lentiviral vector achieves efficient gene delivery in vivo", Nat Biotechnol. (1997), 15(9): 871-875.

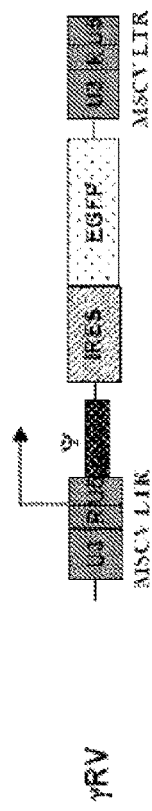
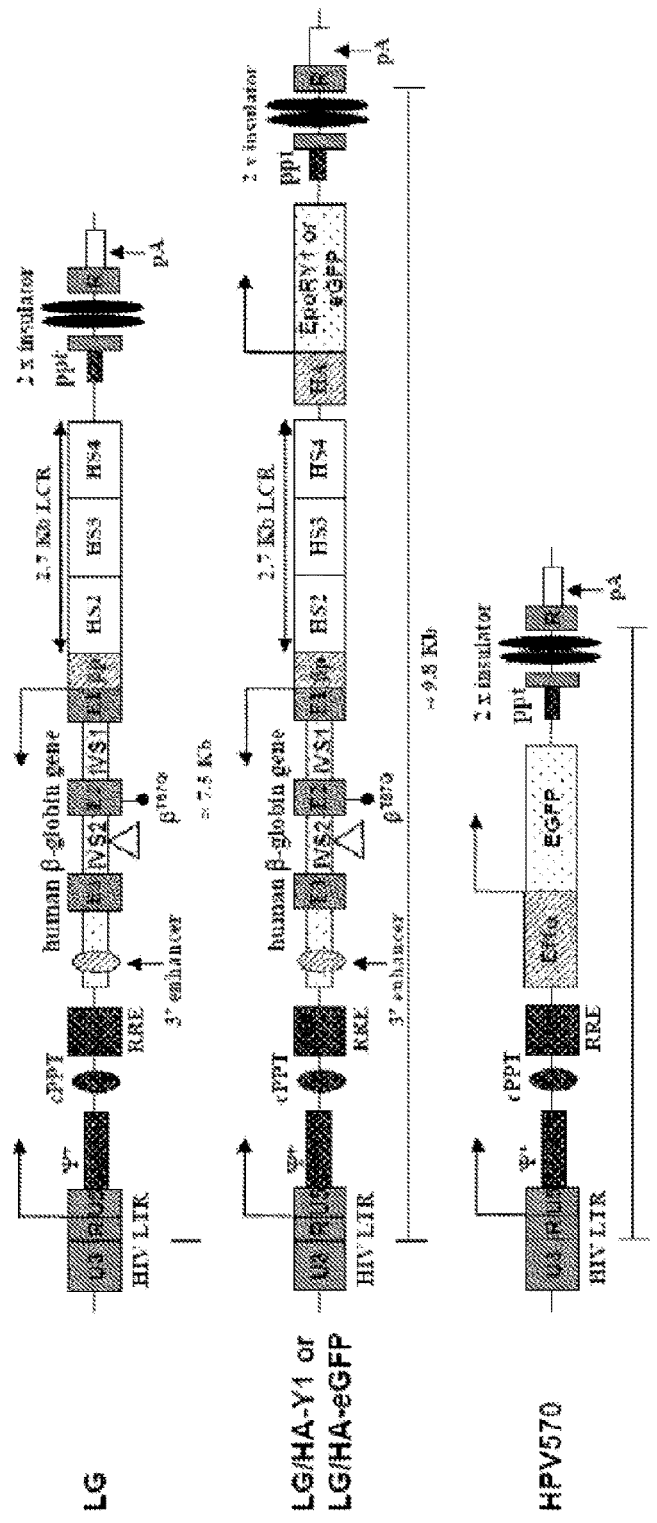
FIG. 1A
FIG. 1B

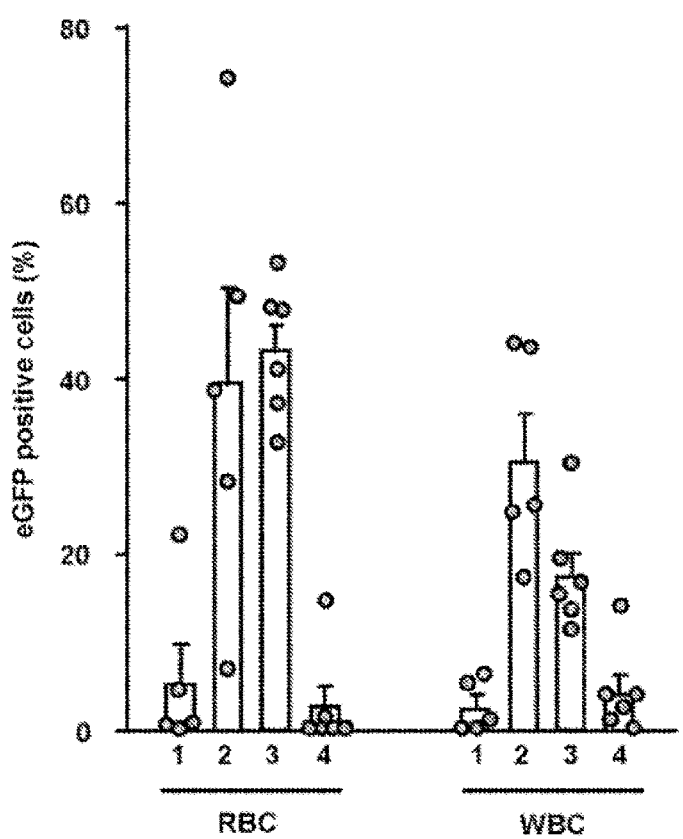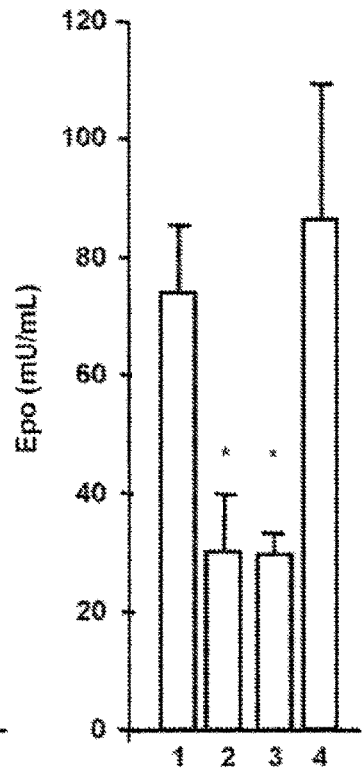
*FIG. 2A*  *FIG. 2B*

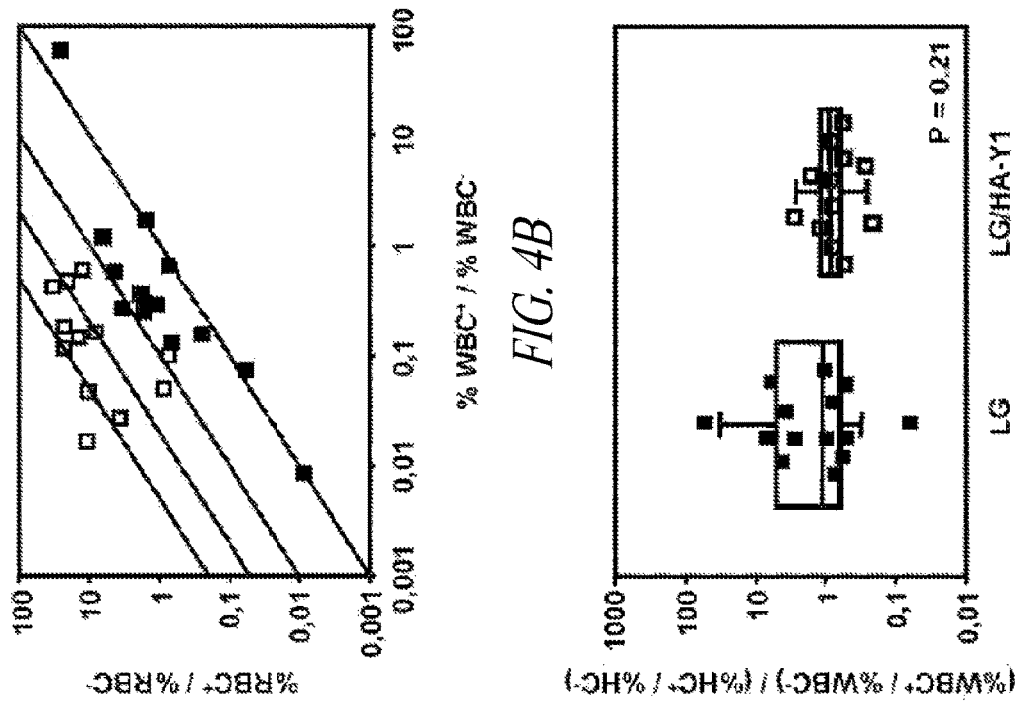
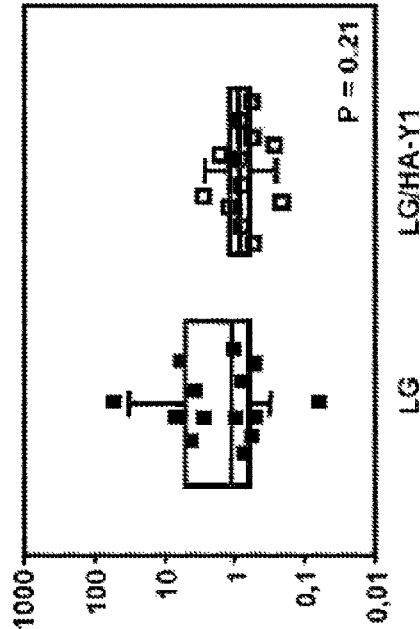
FIG. 4B
FIG. 4A
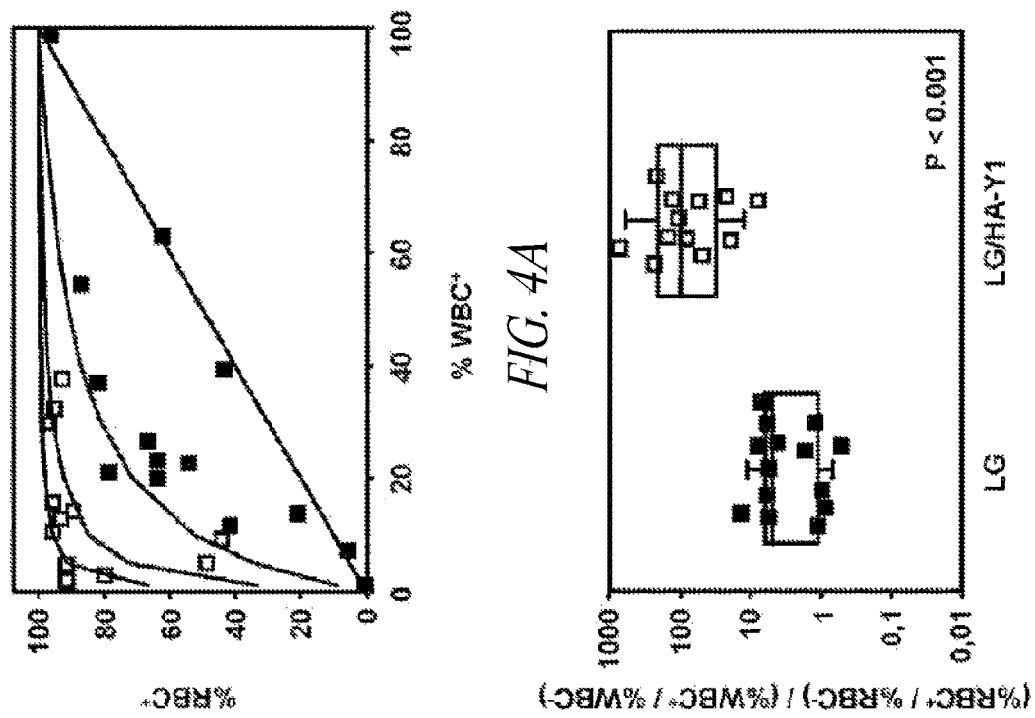
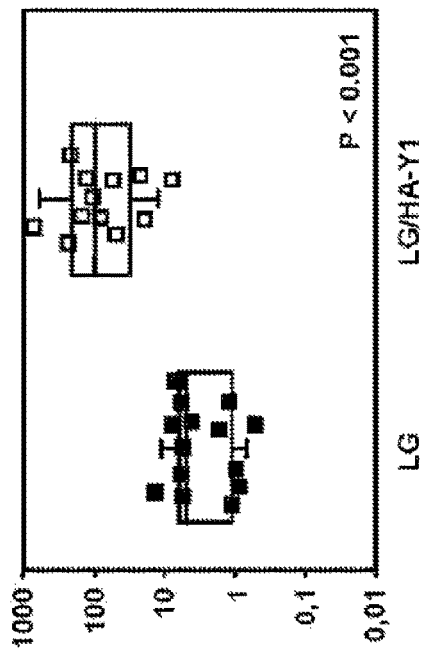
FIG. 4D
FIG. 4C

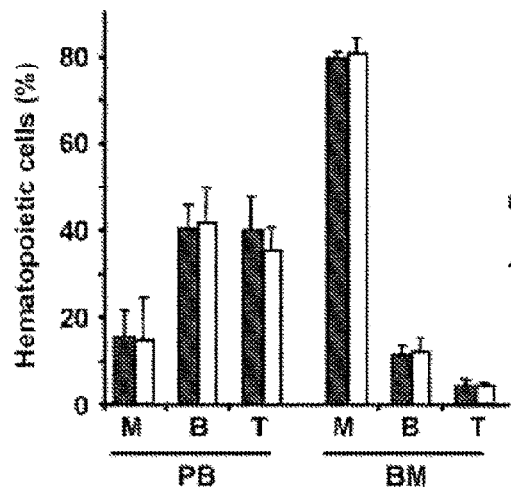
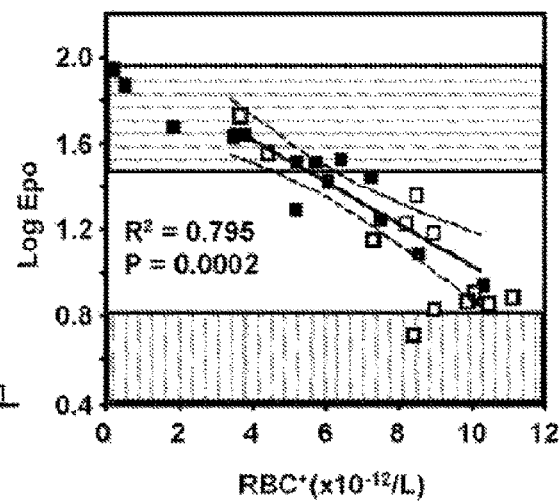
*FIG. 7A*  *FIG. 7B*
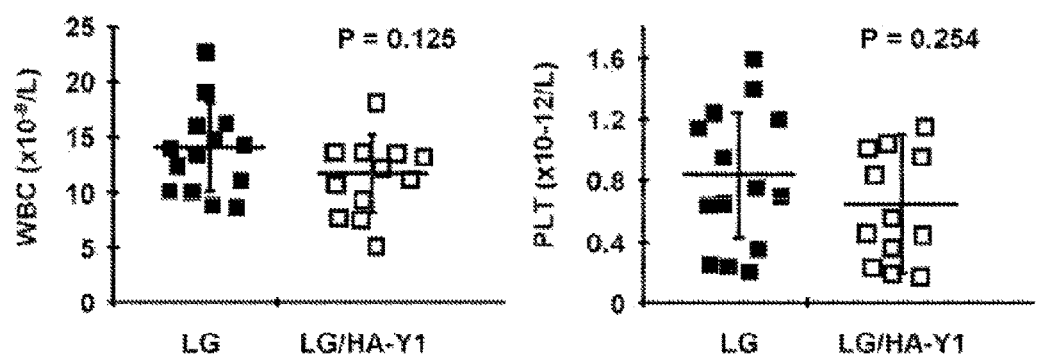
*FIG. 7C*

GENE THERAPY METHODS

CROSS REFERENCE TO RELATED APPLICATIONS

This application is a continuation of U.S. application Ser. No. 14/346,647 (now U.S. Pat. No. 9,783,822), which is a 371 of International Application No. PCT/US2011/053096, filed Sep. 23, 2011, which applications are hereby incorporated by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BLBD_005_03US_ST25.txt. The text file is 95 KB, was created on Oct. 9, 2017, and is being submitted electronically via EFS-Web.

BACKGROUND

Technical Field

The present invention generally relates to compositions used for expanding cells and for treatment of disorders using gene therapy. More particularly, the present invention relates to improved gene therapy compositions for expanding hematopoietic cells and related methods for treatment of diseases, disorders, and conditions of the hematopoietic system.

Description of the Related Art

Recent progress in the field of gene therapy has raised the hope that patients afflicted with hemoglobinopathies such as β thalassemia and sickle cell anemia will benefit from novel therapeutic approaches. Transplantation of hematopoietic cells (HCs) modified with lentiviral vectors carrying the β-globin gene has resulted in long-term correction of several mouse models of hemoglobin disorders Imren et al., *Proc Natl Acad Sci USA*. 2002; 99(22):14380-14385; Malik et al., *Ann NY Acad Sci*. 2005; 1054:238-249; May et al., *Nature*. 2000; 406(6791):82-86; Pawliuk et al., *Science*. 2001; 294 (5550): 2368-2371), but in contrast, has led to transfusion independency in only one β thalassemic patient (Cavazzana-Calvo et al., *Nature*. 2010; 467(7313):318-322). Although the main advantages of infusing genetically modified autologous cells are to avoid the risks of GVHD and immunosuppressive pretransplant conditioning as well as to address the lack of compatible donors, current therapy faces at least three substantive caveats: the requirement for toxic myeloablation (Dunbar et al., *Hum Gene Ther*. 1998; 9(17): 2629-2640); current gene transfer methods are unable to transduce more than a fraction of hematopoietic stem cells (HSCs) (Santoni de Sio and Naldini, *Methods Mol Biol*. 2009; 506:59-70); and various in vivo selection strategies available suffer from suboptimal efficacy and safety (Beard et al., *J Clin Invest*. 2010; 120(7):2345-2354; Cornetta et al., *Cancer Gene Ther*. 2006; 13(9):886-895; Milsom et al., *Cancer Res*. 2008; 68(15): 6171-6180).

For example, β thalassemic recipient mice required at least 200 rads of irradiation and a very high dose of bone marrow cells ($>20\times10^6$) to achieve stable engraftment and phenotypic improvement (Bradley et al., *Biol Blood Marrow Transplant* 2002; 8(8):453-461. However, cytokine-expanded marrow cells have a defective long-term repopulating capability in irradiated (Peters et al., *Blood*. 1996; 87(1):30-37) as well as nonmyeloablated mouse recipients, (Ramshaw et al., *Blood*. 1995; 86(3):924-929) leading to low-level engraftment of retroviral transduced cells in mice and patients in the absence of a pretransplantation conditioning regimen (Dunbar et al., 1998; Kittler et al., *Blood*. 1997; 90(2):865-872).

Accordingly, there is a need in the art for improved methods of gene therapy for the treatment or prevention of hematopoietic disorders. The present invention offers solutions to these and other problems that plague the art.

BRIEF SUMMARY

The present provides compositions for expanding cells and for treatment of disorders using gene therapy. In various embodiments, the present invention provides improved gene therapy compositions for expanding hematopoietic cells and related methods for treatment of diseases, disorders, and conditions of the hematopoietic system.

In various embodiments, the present invention contemplates, in part, a vector comprising: a left (5') retroviral LTR; hematopoietic cell expression control sequence operably linked to a gene of interest; an ubiquitous expression control sequence operably linked to a truncated erythropoietin receptor (tEpoR); and a right (3') retroviral LTR.

In a particular embodiment, the hematopoietic cell expression control sequence is a hematopoietic stem cell promoter or a hematopoietic progenitor cell promoter.

In a certain embodiment, the hematopoietic cell expression control sequence comprises an erythroid cell specific promoter and optionally an erythroid cell specific enhancer.

In a further embodiment, the hematopoietic cell expression control sequence is selected from the group consisting of: a human β-globin promoter; a human β-globin LCR; and a human α-globin HS40 enhancer and an ankyrin-1 promoter.

In an additional embodiment, the ubiquitous expression control sequence is selected from the group consisting of: a cytomegalovirus immediate early gene promoter (CMV), an elongation factor 1 alpha promoter (EF1-α), a phosphoglycerate kinase-1 promoter (PGK), a ubiquitin-C promoter (UBQ-C), a cytomegalovirus enhancer/chicken beta-actin promoter (CAG), polyoma enhancer/herpes simplex thymidine kinase promoter (MC1), a beta actin promoter (β-ACT), and a simian virus 40 promoter (SV40).

In one particular embodiment, the gene of interest is selected from the group consisting of: human β-globin, human δ-globin, and human γ-globin.

In another particular embodiment, the human β-globin gene is the human βA-globin gene encoding a threonine to glutamine mutation at codon 87 ($\beta^{A-T87Q}$) or a human βA-globin gene.

In a certain particular embodiment, the tEpoR comprises a C-terminal truncation.

In an additional particular embodiment, the C-terminal truncation reduces the turnover of the tEpoR compared to an endogenous erythropoietin receptor (EpoR).

In a further particular embodiment, the C-terminal truncation increases the half-life of the tEpoR compared to an endogenous erythropoietin receptor (EpoR).

In various embodiments, the present invention contemplates, in part, a vector comprising: a left (5') retroviral LTR; a first erythroid cell specific expression control sequence operably linked to a gene of interest; a second erythroid cell specific expression control sequence operably linked to a tEpoR; and a right (3') retroviral LTR.

In one embodiment, the first erythroid cell specific expression control sequence is selected from the group consisting of: a human β-globin promoter; a human β-globin LCR; and a human α-globin HS40 enhancer and an ankyrin-1 promoter.

In a particular embodiment, the second erythroid cell specific expression control sequence is selected from the group consisting of: a human β-globin promoter; a human β-globin LCR; and a human α-globin HS40 enhancer and an ankyrin-1 promoter.

In a certain embodiment, the gene of interest is selected from the group consisting of: human β-globin, human δ-globin, and human γ-globin.

In a certain particular embodiment, the human β-globin gene is selected from the group consisting of a wild type human β-globin gene, a deleted human β-globin gene comprising one or more deletions of intron sequences, and a mutated human β-globin gene encoding at least one antisickling amino acid residue.

In a further embodiment, the human β-globin gene is the human βA-globin gene encoding a threonine to glutamine mutation at codon 87 (βA-T87Q) or a human βA-globin gene.

In a further particular embodiment, the tEpoR comprises a C-terminal truncation.

In an additional embodiment, the tEpoR comprises a C-terminal truncation of about 10 to about 100 amino acids.

In a further additional embodiment, the tEpoR comprises a C-terminal truncation of 50 to 60 amino acids.

In one particular embodiment, the tEpoR comprises a C-terminal truncation of 80 to 90 amino acids.

In another particular embodiment, the tEpoR comprises a C-terminal truncation of 85 to 95 amino acids.

In yet another particular embodiment, the tEpoR comprises a C-terminal truncation of about 55, about 83, or about 91 amino acids.

In various embodiments, the present invention contemplates, in part, a vector comprising: a left (5') retroviral LTR; a β-globin promoter and a β-globin locus control region (LCR) operably linked to a gene of interest; an expression control sequence operably linked to a truncated erythropoietin receptor (tEpoR); and a right (3') retroviral LTR.

In one embodiment, any of the vectors contemplated herein is a lentivirus vector.

In a certain embodiment, any of the vectors contemplated herein comprise a 5' LTR or 3' LTR from a lentivirus, i.e., a lentivirus LTR.

In a certain particular embodiment, any of the vectors contemplated herein comprise a 5' LTR and 3' LTR from a lentivirus, i.e., lentivirus LTRs.

In a certain further embodiment, the lentivirus is selected from the group consisting of: human immunodeficiency virus type 1 (HIV-1), human immunodeficiency virus type 2 (HIV-2), visna virus, caprine arthritis-encephalitis virus (CAEV), equine infectious anemia virus (EIAV), feline immunodeficiency virus (Hy), bovine immune deficiency virus (BIV), and simian immunodeficiency virus (SIV).

In a certain additional embodiment, the lentivirus is HIV-1.

In a particular additional embodiment, the promoter of the 5' LTR is replaced with a heterologous promoter.

In a particular further embodiment, the heterologous promoter is a cytomegalovirus (CMV) promoter, a Rous Sarcoma Virus (RSV) promoter, a thymidine kinase promoter, or an Simian Virus 40 (SV40) promoter.

In a particular certain embodiment, any of the vectors contemplated herein comprise a 3' LTR comprising one or more modifications.

In a particular embodiment, any of the vectors contemplated herein comprise a 3' LTR comprising one or more deletions.

In one particular embodiment, any of the vectors contemplated herein comprise a 3' LTR that is a self-inactivating (SIN) LTR.

In one embodiment, the β-globin promoter is a human β-globin promoter.

In another embodiment, the β-globin LCR comprises one or more of DNAase I hypersensitive sites 2, 3 and 4 from the human β-globin LCR.

In an additional embodiment, the gene of interest is a globin gene.

In a further embodiment, the globin gene is selected from the group consisting of: human β-globin, human δ-globin, and human γ-globin.

In a certain embodiment, the human β-globin gene is selected from the group consisting of a wild type human β-globin gene, a deleted human β-globin gene comprising one or more deletions of intron sequences, and a mutated human β-globin gene encoding at least one antisickling amino acid residue.

In a particular embodiment, the human β-globin gene is the human βA-globin gene encoding a threonine to glutamine mutation at codon 87 ($β^{A-T87Q}$) or a human βA-globin gene.

In one particular embodiment, any of the vectors contemplated herein further comprise a human β-globin 3' enhancer element.

In a further embodiment, the expression control sequence is a ubiquitous expression control sequence selected from the group consisting of: a cytomegalovirus immediate early gene promoter (CMV), an elongation factor 1 alpha promoter (EF1-α), a phosphoglycerate kinase-1 promoter (PGK), a ubiquitin-C promoter (UBQ-C), a cytomegalovirus enhancer/chicken beta-actin promoter (CAG), polyoma enhancer/herpes simplex thymidine kinase promoter (MC1), a beta actin promoter (β-ACT), and a simian virus 40 promoter (SV40).

In a particular embodiment, the expression control sequence is an erythroid specific expression control sequence is selected from the group consisting of: a human β-globin promoter; a human β-globin LCR; and a human α-globin HS40 enhancer and an ankyrin-1 promoter.

In a certain particular embodiment, the erythroid specific expression control sequence comprises a human α-globin HS40 enhancer and an ankyrin-1 promoter.

In a particular embodiment, any of the vectors contemplated herein comprise one or more of a Psi packaging sequence (Ψ+), a central polypurine tract/DNA flap (cPPT/FLAP), a retroviral export element, a posttranscriptional regulatory element, an insulator element, a polyadenylation sequence, a selectable marker, and a cell suicide gene.

In a certain embodiment, any of the vectors contemplated herein comprise a Psi packaging sequence (Ψ+), a central polypurine tract/DNA flap (cPPT/FLAP), a retroviral export element, an insulator element, and a polyadenylation sequence.

In a further embodiment, any of the vectors contemplated herein comprise a retroviral export element that is a rev response element (RRE).

In an additional, embodiment, any of the vectors contemplated herein comprise a cPPT/FLAP from HIV-1.

In one embodiment, any of the vectors contemplated herein comprise a gene of interest comprising an optimized Kozak sequence.

In various embodiments, the tEpoR comprises an optimized Kozak sequence.

In a particular embodiment, any of the vectors contemplated herein comprise an optimal Kozak sequence, (GCC) RCCATGG, wherein R is a purine (A or G).

In an additional embodiment, the 3' LTR comprises at least one insulator element.

In a certain additional embodiment, the 3' LTR comprises two insulator elements.

In a particular additional embodiment, an insulator comprises a polynucleotide sequence as set forth in SEQ ID NOs: 37 or 38.

In a further additional embodiment, an insulator comprises a polynucleotide sequence as set forth in nucleotides 8-49 of SEQ ID NO: 37.

In a certain embodiment, the polyadenylation sequence is selected from the group consisting of: AATAAA, ATTAAA, AGTAAA, a bovine growth hormone polyA sequence (BGHpA), and a rabbit β-globin polyA sequence (rβgpA).

In one embodiment, the tEpoR comprises a C-terminal truncation.

In another embodiment, the tEpoR comprises a C-terminal truncation of about 10 to about 100 amino acids.

In yet another embodiment, the tEpoR comprises a C-terminal truncation of 50 to 60 amino acids.

In still yet another embodiment, the tEpoR comprises a C-terminal truncation of 80 to 90 amino acids.

In a particular embodiment, the tEpoR comprises a C-terminal truncation of 85 to 95 amino acids.

In a further embodiment, the tEpoR comprises a C-terminal truncation of about 55, about 83, or about 91 amino acids.

In various embodiments, the present invention contemplates, in part, a vector comprising: a left (5') retroviral LTR; a Psi packaging sequence (Ψ+); a central polypurine tract/DNA flap (cPPT/FLAP); a retroviral export element; a β-globin promoter and a β-globin locus control region (LCR) operably linked to a gene of interest; an erythroid cell specific expression control sequence operably linked to a truncated erythropoietin receptor (tEpoR); and a right (3') retroviral LTR that comprises one or more insulator elements, or a polyadenylation sequence.

In various particular embodiments, the present invention contemplates, in part, a lentiviral vector comprising: a left (5') HIV-1 LTR; a Psi packaging sequence (Ψ+); an HIV-1 central polypurine tract/DNA flap (cPPT/FLAP); a rev response element (RRE); a β-globin promoter and a β-globin locus control region (LCR) operably linked to a gene of interest; an erythroid cell specific expression control sequence operably linked to a truncated erythropoietin receptor (tEpoR); and a right (3') retroviral LTR that comprises one or more insulator elements, and a rabbit β-globin polyA sequence (rβgpA).

In various other embodiments, the present invention contemplates, in part, a composition comprising any of the vectors contemplated herein.

In one embodiment, the composition comprises a cell.

In an additional embodiment, the cell is selected from the group consisting of: an embryonic stem cell, an adult stem cell, an adult progenitor cell, and a differentiated adult cell.

In a particular embodiment, the cell is a hematopoietic stem cell or a hematopoietic progenitor cell.

In a further embodiment, the source of the stem or progenitor cell is bone marrow, cord blood, placental blood, or peripheral blood.

In a certain embodiment, the cell is transduced with the vector.

In another embodiment, the vector is an episomal vector or is not integrated into the genome of the cell.

In a particular embodiment, the vector is integrated into the genome of the cell.

In one particular embodiment, the integration is targeted to a location in the genome.

In various embodiments, the present invention contemplates, in part, a method of providing a transduced cell to a subject comprising: administering a population of cells comprising a cell transduced with any of the vectors contemplated herein.

In a particular embodiment, the transduced cells comprise hematopoietic stem cells.

In a certain particular embodiment, the transduced cells comprise hematopoietic progenitor cells.

In a certain embodiment, the population of cells comprises 5% cells transduced with any of the vectors contemplated herein.

In a further embodiment, the population of cells comprises 10% cells transduced with any of the vectors contemplated herein.

In a related particular embodiment, the population of cells comprises 25% cells transduced with any of the vectors contemplated herein.

In various embodiments, a method of providing a transduced cell to a subject further comprises administering erythropoietin to the subject.

In one embodiment, the population of cells and erythropoietin are administered parenterally.

In certain embodiments, the parenteral administration is intravenous administration.

In additional embodiments, the population of cells is administered to the subject before the erythropoietin is administered to the subject.

In one embodiment, the subject has a hemoglobinopathy.

In particular embodiments, the hemoglobinopathy is selected from the group consisting of: hemoglobin C disease, hemoglobin sickle cell disease (SCD), sickle cell anemia, hereditary anemia, thalassemia, β-thalassemia, thalassemia major, thalassemia intermedia, α-thalassemia, and hemoglobin H disease.

In various other embodiments, the present invention contemplates, in part, a method of treating a hemoglobinopathy in a subject comprising: administering a population of cells comprising hematopoietic stem or progenitor cells transduced with any of the vectors contemplated herein, wherein the hematopoietic stem or progenitor cells or progeny cells of the hematopoietic stem or progenitor cells are increased in the subject after the administration of erythropoietin compared to hematopoietic stem or progenitor cells or progeny cells in the subject before the administration of erythropoietin.

In a particular embodiment, the population of cells was isolated from bone marrow, cord blood, placental blood, or peripheral blood.

In an additional embodiment, 5% of the hematopoietic stem or progenitor cells have been transduced.

In a certain embodiment, 10% of the hematopoietic stem or progenitor cells have been transduced.

In a further embodiment, 25% of the hematopoietic stem or progenitor cells have been transduced.

In a particular embodiment, a method of treating a hemoglobinopathy in a subject comprises administering erythropoietin to the subject.

In one embodiment, the population of cells and erythropoietin are administered intravascularly.

In a further embodiment, the administration is intravenous.

In another embodiment, the hemoglobinopathy is selected from the group consisting of: hemoglobin C disease, hemoglobin sickle cell disease (SCD), sickle cell anemia, hereditary anemia, thalassemia, β-thalassemia, thalassemia major, thalassemia intermedia, α-thalassemia, and hemoglobin H disease.

In another particular embodiment, the hemoglobinopathy is β-thalassemia.

In a certain particular embodiment, the subject has undergone is or undergoing bone marrow ablative chemotherapy or irradiation.

In a particular further embodiment, the progeny cells increased in the subject comprise erythroid cells.

In an additional particular embodiment, the erythroid cells are erythroid progenitor cells.

In one embodiment, the erythroid cells are erythrocytes.

In one embodiment, the erythroid cells are increased at least 10 fold after the administration of erythropoietin compared to the erythroid cells in the subject before the administration of erythropoietin.

In another embodiment, the erythroid cells are increased at least 25 fold after the administration of erythropoietin compared to the erythroid cells in the subject before the administration of erythropoietin.

In yet another embodiment, the erythroid cells are increased at least 50 fold after the administration of erythropoietin compared to the erythroid cells in the subject before the administration of erythropoietin.

In still yet another embodiment, the erythroid cells are increased at least 100 fold after the administration of erythropoietin compared to the erythroid cells in the subject before the administration of erythropoietin.

In a particular embodiment, the erythroid cells are increased at least 25 fold compared to non-erythroid cells in the subject after the administration of erythropoietin.

In another particular embodiment, the erythroid cells are increased at least 50 fold compared to non-erythroid cells in the subject after the administration of erythropoietin.

In yet another particular embodiment, the erythroid cells are increased at least 100 fold compared to non-erythroid cells in the subject after the administration of erythropoietin.

In still yet another particular embodiment, the erythroid cells are increased at least 150 fold compared to non-erythroid cells in the subject after the administration of erythropoietin.

In various other embodiments, the present invention contemplates, in part, a method of selectively expanding the number erythroid cells in a subject comprising: administering a population of cells comprising hematopoietic stem or progenitor cells transduced with any of the vectors contemplated herein, wherein the number of erythroid progeny cells of the hematopoietic stem cells are expanded in the subject.

In various particular embodiments, the present invention contemplates, in part, a method of increasing the proportion of red blood cells compared to white blood cells in a subject comprising: administering a population of cells comprising hematopoietic stem or progenitor cells transduced with any of the vectors contemplated herein, administering erythropoietin to the subject, wherein the proportion of red blood cell progeny cells of the hematopoietic stem cells are increased compared to white blood cell progeny cells of the hematopoietic stem cells in the subject.

In a particular embodiment, a method of selectively expanding the number erythroid cells in a subject comprises administering erythropoietin to the subject.

In a particular embodiment, a method of increasing the proportion of red blood cells compared to white blood cells in a subject comprises administering erythropoietin to the subject.

In a certain embodiment, the population of cells was isolated from bone marrow, cord blood, placental blood, or peripheral blood.

In one embodiment, 5% of the hematopoietic stem or progenitor cells have been transduced.

In another embodiment, 10% of the hematopoietic stem or progenitor cells have been transduced.

In yet another embodiment, 25% of the hematopoietic stem or progenitor cells have been transduced.

In a certain embodiment, the population of cells and erythropoietin are administered intravascularly.

In another certain embodiment, the administration is intravenous.

In a further embodiment, the subject has a hemoglobinopathy.

In a further particular embodiment, the hemoglobinopathy is selected from the group consisting of: hemoglobin C disease, hemoglobin sickle cell disease (SCD), sickle cell anemia, hereditary anemia, thalassemia, β-thalassemia, thalassemia major, thalassemia intermedia, α-thalassemia, and hemoglobin H disease.

In a further additional embodiment, the hemoglobinopathy is β-thalassemia.

In a further certain embodiment, the subject has undergone is or undergoing bone marrow ablative chemotherapy or irradiation.

In one embodiment, the erythroid progeny cells are increased at least 10 fold after the administration of erythropoietin compared to the erythroid progeny cells in the subject before the administration of erythropoietin.

In another embodiment, the erythroid progeny cells are increased at least 25 fold after the administration of erythropoietin compared to the erythroid progeny cells in the subject before the administration of erythropoietin.

In yet another embodiment, the erythroid progeny cells are increased at least 50 fold after the administration of erythropoietin compared to the erythroid progeny cells in the subject before the administration of erythropoietin.

In still yet another embodiment, the erythroid progeny cells are increased at least 100 fold after the administration of erythropoietin compared to the erythroid progeny cells in the subject before the administration of erythropoietin.

In a particular embodiment, the erythroid progeny cells are increased 25 fold compared to non-erythroid cells in the subject after the administration of erythropoietin.

In another particular embodiment, the erythroid progeny cells are increased 50 fold compared to non-erythroid cells in the subject after the administration of erythropoietin.

In yet another particular embodiment, the erythroid progeny cells are increased 100 fold compared to non-erythroid cells in the subject after the administration of erythropoietin.

In still yet another particular embodiment, the erythroid cells progeny are increased 150 fold compared to non-erythroid cells in the subject after the administration of erythropoietin.

In various embodiments, the erythroid progeny cells comprise erythrocytes.

In a certain embodiment, the RBCs are increased at least 25 fold compared to WBCs in the subject after the administration of erythropoietin.

In another certain embodiment, the RBCs are increased at least 50 fold compared to WBCs in the subject after the administration of erythropoietin.

In yet another certain embodiment, the RBCs are increased at least 100 fold compared to WBCs in the subject after the administration of erythropoietin.

In still yet another certain embodiment, the RBCs are increased at least 150 fold compared to WBCs in the subject after the administration of erythropoietin.

BRIEF DESCRIPTION OF THE SEVERAL VIEWS OF THE DRAWINGS

FIGS. 1A-1D show several viral vector constructs and mouse erythropoietin receptors (EpoR) used in particular experiments described herein. FIG. 1A shows a mouse gammaretroviral vector (γRV) that contains an internal ribosomal entry site (IRES)-driven enhanced green fluorescent protein (eGFP) reporter gene under the control of the MSCV (murine stem cell virus) LTR (long terminal repeat) promoter. EpoR cDNAs were cloned in front of the IRES. FIG. 1B shows a LentiGlobin (LG) vector that encodes a modified β-globin ($\beta^{A T87Q}$) chain under the control of the human β-globin promoter and locus control region (LCR). The LG vector also contains a deletion in the U3 region of the right long terminal repeat (LTR), the rabbit β-globin polyA signal, and the two 250 bp chromatin insulators of the hypersensitive site 4 (HS4) chicken β-globin locus. LG/HA-Y1 contains a truncated EpoR-Y1 cDNA under control of a human α-globin HS40 enhancer and an ankyrin-1 promoter. LG/HA-eGFP contains eGFP in place of EpoRY1. HPV570 contains eGFP under the control of an EF1α promoter. FIG. 1C shows murine wild type (EpoRY1-8) and truncated EpoR (EpoRY1-7 to EpoRY1). The first 24 amino acids that constitute the hydrophobic leader sequence are not present and are not taken into account in numbering. Tyrosine (Y) 343, 401, 429,431, 443, 460, 464 and 479 are shown. In EpoRY1 and EpoRY1-2, a stop codon replaces Y401 and Y429. FIG. 1D shows human wild type (hEpoRY1-8) and truncated EpoR (hEpoRY1-7 to EpoRY1). The first 24 amino acids that constitute the hydrophobic leader sequence are not present and are not taken into account in numbering. Tyrosine (Y) 344, 402, 430,432, 444, 461, 465 and 480 are shown.

FIGS. 2A-2B show an increase in the proportion of peripheral blood cells modified by tEpoR, 20 weeks after transplantation. FIG. 2A shows mean percentages, standard errors, and individual values of eGFP-positive RBCs and WBCs. Hematopoietic cells (HCs) were transduced by γRV (1), γRV/EpoRY1 (2), γRV/EpoRY1-2 (3), or γRV/EpoRY1-8 (4) retroviral vectors. FIG. 2B shows mean plasma Epo levels and standard errors measured in the same mice. *P<0.05 compared with groups 1 and 4.

FIGS. 4A-4D show that tEpoR mediates erythroid cell amplification. FIGS. 4A and 4B show the relationship between the percentage of modified RBCs and the percentage of transduced WBCs in the peripheral blood of LG (■) and LG/HA-EpoRY1 (□) mice. Assuming a minimal effect of tEpoR on modified leukocytes, 4 theoretical curves corresponding to 1-, 10-, 50-, and 200-fold preferential expansion of modified erythroid cells ($F^E$ factor) are derived from equations 3 (FIG. 4A) and 2 (FIG. 4B). Greater curvature (FIG. 4A) and left shift of the straight lines (FIG. 4B) corresponds to greater advantage for modified erythroid cells over unmodified cells. FIGS. 4C-4D show the bottom and top boundary of the boxes indicate the $25^{th}$ and $75^{th}$ percentiles. Whiskers (error bars) above and below the box indicate the $90^{th}$ and $10^{th}$ percentiles. The line within the box marks the median. (FIG. 4C) Median and individual erythroid amplification factor $F^E$ in LG (■) and LG/HA-EpoRY1 (□) mice. (FIG. 4D) Median and individual ratio between the genetically modified leukocyte (WBC) fraction and the ex vivo-modified HC fraction before transplantation in LG (■) and LG/HA-EpoRY1 (□) mice.

FIG. 5A shows the correlation of total and human hemoglobin concentrations (Hb), erythrocyte counts (RBC), reticulocyte percentages (Retic), and spleen weight with modified RBC of transplanted β thalassemic mice. Regression lines and 95% confidence intervals (dashed lines) were obtained from LG mice having a proportion of RBC greater than 40%. The bottom and top boundaries of the horizontally and vertically hatched boxes indicate mean±SD of values from β thalassemic and normal C57BL/6J mice. For hemoglobin, the bottom and top regression lines corresponds to therapeutic (human) and total hemoglobin, respectively. FIG. 5B shows the correlation of spleen weight with percentage of erythroid cells in the spleen. The regression line and 95% confidence interval were plotted with data from all mice. Three mice receiving mock-transduced cells were included (●).

FIG. 6A shows the correlation of modified RBC (RBC), hematocrit values (Hc), total hemoglobin concentrations (Hb), and reticulocyte percentages (Retic) with modified WBC (WBC) of transplanted β thalassemic mice. The hatched line separates data with WBC below and above 20%. FIG. 6B shows the mean±SD and individual modified RBC percentages, hematocrit values, total hemoglobin concentrations, and reticulocyte percentages of mice with WBC below and above 20%. Numbers below the graphs indicate the mean percentage of modified WBCs.

FIGS. 7A-7C show that BM homeostasis is maintained 10 months after transplantation. FIG. 7A shows the proportion of myeloid (M), B-lymphoid (B), and T-lymphoid (T) cells among CD45.2-positive leukocytes in peripheral blood (PB) and bone marrow (BM) of LG (filled bars) and LG/HA-Y1 (open bars) mice. FIG. 7B shows the logarithm of plasma Epo with human corrected RBC (RBC). The regression line and 95% confidence intervals (dashed lines) were obtained from LG mice having a proportion of RBC greater than 40%. The bottom and top boundaries of the horizontally and vertically hatched boxes indicate mean SD of values from β thalassemic and normal C57BL/6J mice, respectively. FIG.

7C shows the mean SD and individual leukocyte and platelet numbers in peripheral blood of LG (■) and LG/HA-Y1 (□) mice.

Figure 8A:
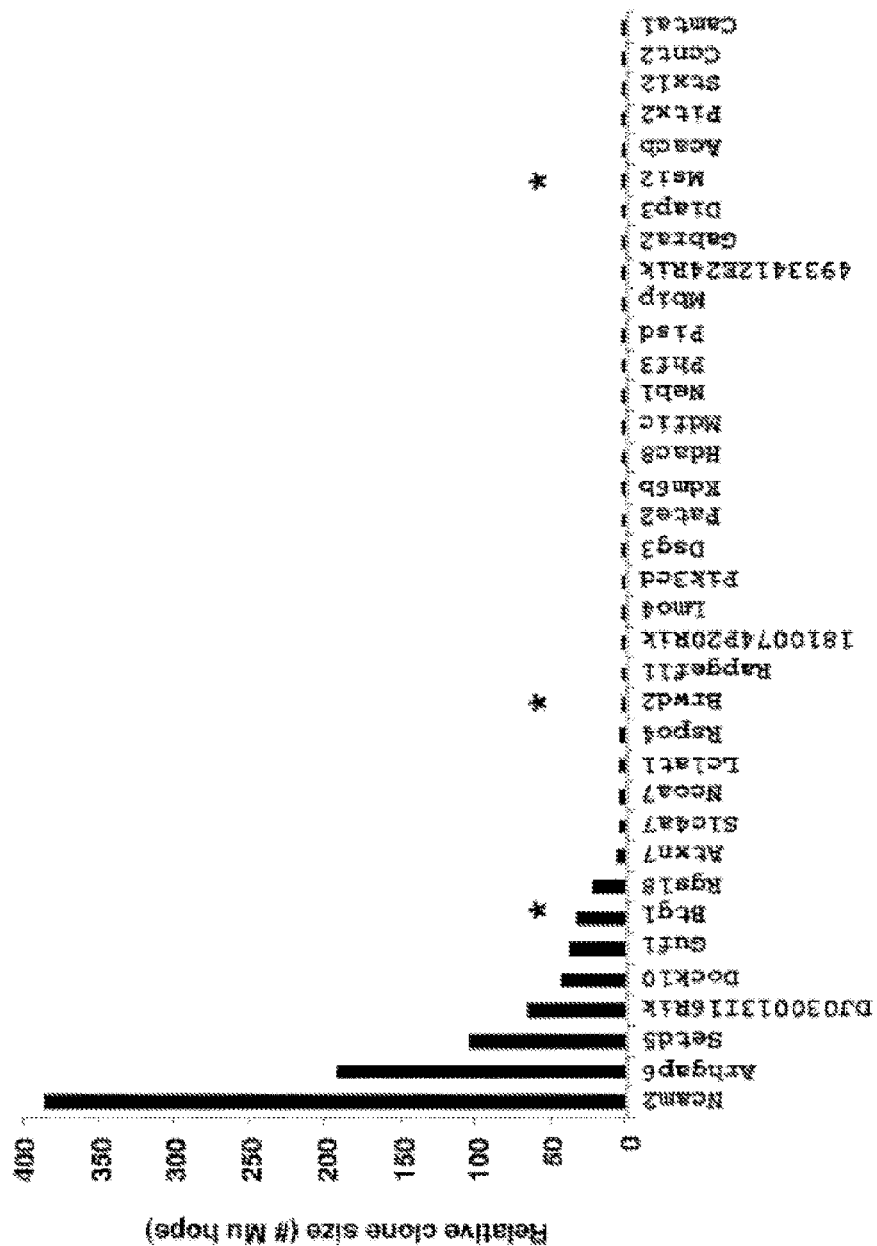
Figure 8C:
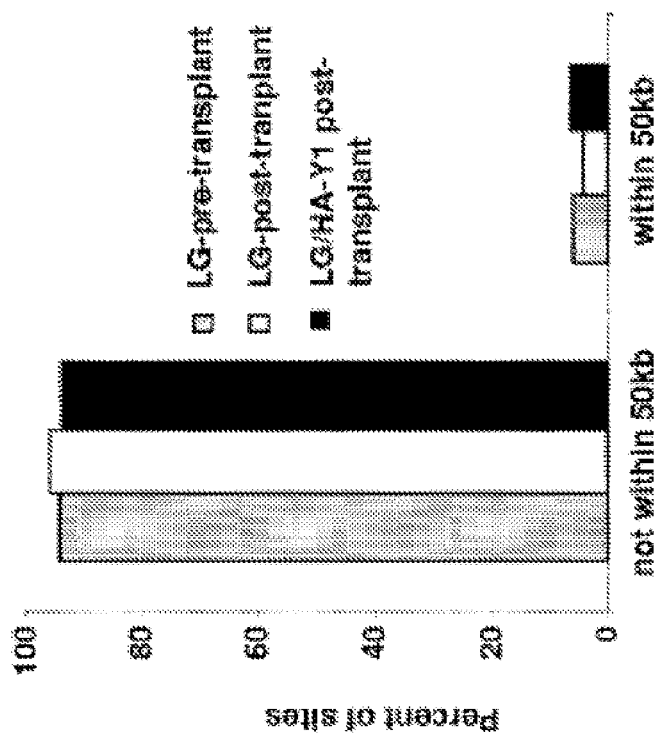
Figure 8B:
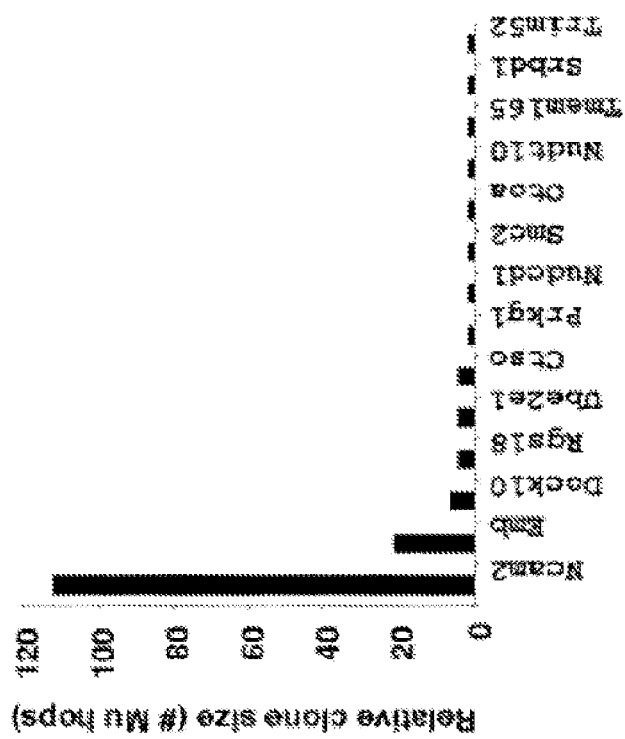

FIGS. 8A-8C show a lack of association of LG/HA-EpoRY1 vector integration sites (IS) with proto-oncogenes after erythroid cell expansion. Integration sites from all 4 mice were pooled for this analysis. Integration sites isolated from Ter119+ (FIG. 8A) and CD45+ (FIG. 8B) BM cells are labeled according to the nearest RefSeq gene. The relative clone size was quantified by the number of times it was isolated with independent integration events catalyzed by MuA transposase in vitro. Proto-oncogenes, as annotated in the allOnco database, are indicated by asterisks. The frequency of IS in which the nearest gene is an oncogene is not statistically different between erythroid and nonerythroid cells (P=0.5523). FIG. 8C shows integration site proximity to proto-oncogenes. The proportions of integration sites >50 kb and <50 kb from a proto-oncogene are shown. No significant differences in the number of integration sites found <50 kb from a proto-oncogene were found between integration sites identified in this study and IS characterized in HCs transduced with the LG vector before and after transplantation (P>0.05 with the 2-tailed Fisher exact test).

Figure 9:
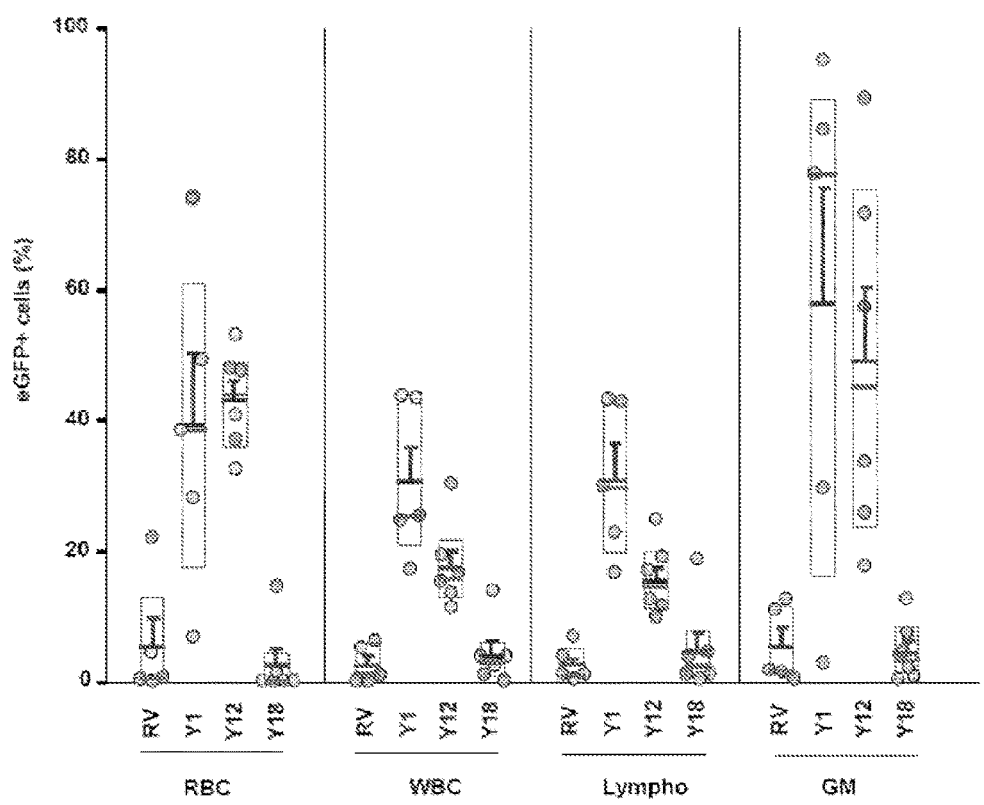

FIG. 9 shows that tEpoR induces a high proportion of eGFP+ erythroid, lymphoid and myeloid cells twenty weeks post-transplantation. Mean and median percentages (blue and red lines respectively), standard errors (blue error bars), 25th and 75th percentiles (bottom and top boundary of the boxes) and individual percentages (grey circles) of eGFP positive cells in the red blood cells (RBC), white blood cells (WBCs), lymphoid cells (lympho) and myeloid cells (GM: granulo/monocytes) compartments. Hematopoietic cells were transduced by γRV, γRV/EpoRY1 (Y1), γRV/EpoRY1-2 (Y1-2) or γRV/EpoRY1-8 (Y1-8) retroviral vectors.

Figure 10:
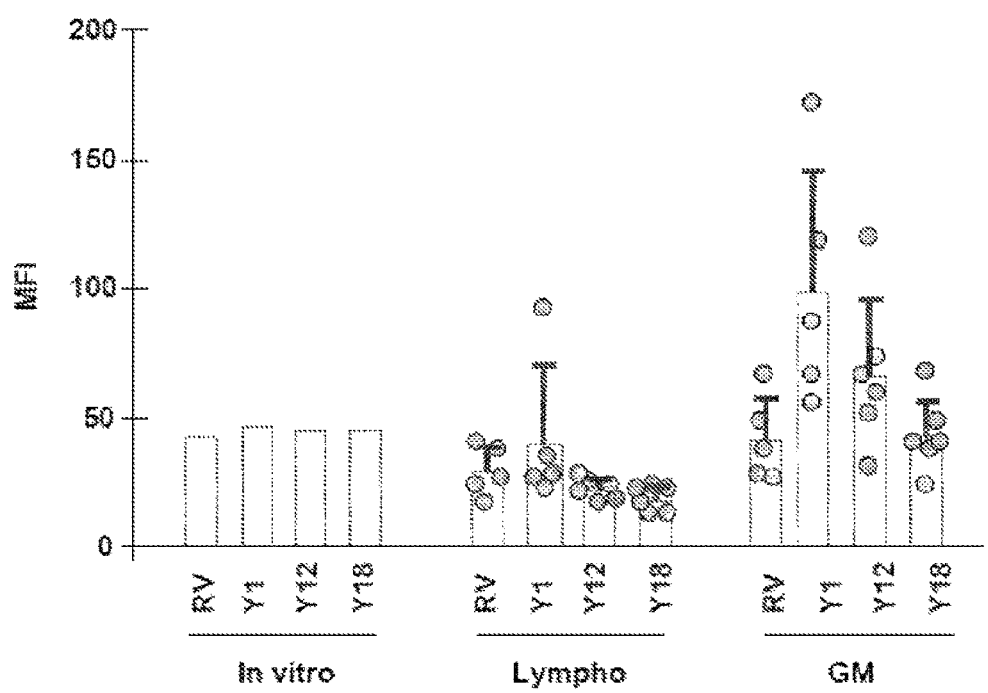

FIG. 10 shows that myeloid cells expressing the highest level of eGFP are selected in mouse transplanted with cells modified by tEpoR. Mean of the mean fluorescence intensities (histograms), standard deviations (blue error bars), and individual MFI (grey circles) in hematopoietic cells before transplantation (in vitro) and in lymphoid cells (lympho) and myeloid cells (GM) compartments. Hematopoietic cells were transduced by γRV, γRV/EpoRY1 (Y1), γRV/EpoRY1-2 (Y1-2) or γRV/EpoRY1-8 (Y1-8) retroviral vectors.

Figure 11:
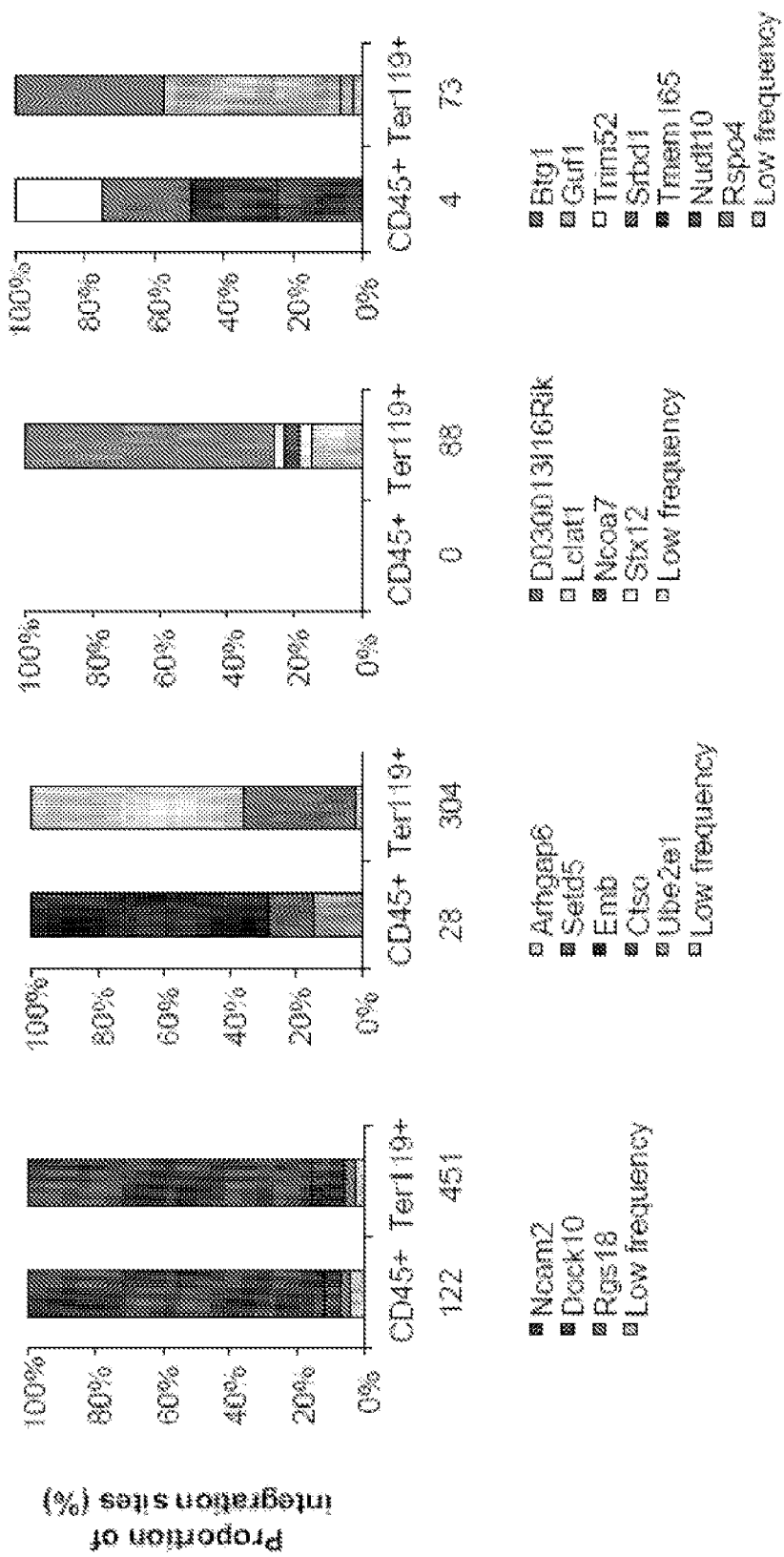

FIG. 11 shows the distribution of integration sites isolated from CD45+ and Ter119+ bone marrow cells of four LG/HA-EpoRY1 mice. Integration sites are labeled according to the nearest RefSeq gene. The proportion of sites recovered was quantified by the number of times it was isolated with independent integration events catalyzed by MuA transposase in vitro. Sites recovered that contributed to less than 2% of the isolated integration sites were combined into the low frequency group. The number of independent Mu transposition events, reflecting clonal abundance, is indicated below each cell type of each mouse.

BRIEF DESCRIPTION OF THE SEQUENCE IDENTIFIERS

SEQ ID NO: 1 sets forth a polynucleotide sequence of a human alpha globin cDNA.
SEQ ID NO: 2 sets forth an amino acid sequence of a human alpha globin polypeptide.
SEQ ID NO: 3 sets forth an amino acid sequence of a mouse alpha globin polypeptide.
SEQ ID NO: 4 sets forth an amino acid sequence of a rat alpha globin polypeptide.
SEQ ID NO: 5 sets forth a polynucleotide sequence of a human beta globin cDNA.
SEQ ID NO: 6 sets forth an amino acid sequence of a human beta globin polypeptide.
SEQ ID NO: 7 sets forth an amino acid sequence of a mutant human beta globin polypeptide.
SEQ ID NO: 8 sets forth an amino acid sequence of a mouse beta globin polypeptide.
SEQ ID NO: 9 sets forth an amino acid sequence of a rat beta globin polypeptide.
SEQ ID NO: 10 sets forth a polynucleotide sequence of a human gamma globin cDNA.
SEQ ID NO: 11 sets forth an amino acid sequence of a human gamma globin polypeptide.
SEQ ID NO: 12 sets forth an amino acid sequence of a mouse gamma globin polypeptide.
SEQ ID NO: 13 sets forth an amino acid sequence of a rat gamma globin polypeptide.
SEQ ID NO: 14 sets forth a polynucleotide sequence of a human delta globin cDNA.
SEQ ID NO: 15 sets forth an amino acid sequence of a human delta globin polypeptide.
SEQ ID NO: 16 sets forth a polynucleotide sequence of a human erythropoietin receptor cDNA.
SEQ ID NO: 17 sets forth a polynucleotide sequence of a mouse erythropoietin receptor cDNA.
SEQ ID NO: 18 sets forth a polynucleotide sequence of a rat erythropoietin receptor cDNA.
SEQ ID NO: 19 sets forth an amino acid sequence of a human erythropoietin receptor polypeptide.
SEQ ID NO: 20 sets forth an amino acid sequence of a truncated human erythropoietin receptor polypeptide.
SEQ ID NO: 21 sets forth an amino acid sequence of a truncated human erythropoietin receptor polypeptide.
SEQ ID NO: 22 sets forth an amino acid sequence of a human erythropoietin receptor polypeptide lacking the 24 amino acid N-terminal signal peptide.
SEQ ID NO: 23 sets forth an amino acid sequence of a truncated human erythropoietin receptor polypeptide lacking the 24 amino acid N-terminal signal peptide.
SEQ ID NO: 24 sets forth an amino acid sequence of a truncated human erythropoietin receptor polypeptide lacking the 24 amino acid N-terminal signal peptide.
SEQ ID NO: 25 sets forth an amino acid sequence of a mouse erythropoietin receptor polypeptide.
SEQ ID NO: 26 sets forth an amino acid sequence of a truncated mouse erythropoietin receptor polypeptide.
SEQ ID NO: 27 sets forth an amino acid sequence of a truncated mouse erythropoietin receptor polypeptide.
SEQ ID NO: 28 sets forth an amino acid sequence of a mouse erythropoietin receptor polypeptide lacking the 24 amino acid N-terminal signal peptide.
SEQ ID NO: 29 sets forth an amino acid sequence of a truncated mouse erythropoietin receptor polypeptide lacking the 24 amino acid N-terminal signal peptide.
SEQ ID NO: 30 sets forth an amino acid sequence of a truncated mouse erythropoietin receptor polypeptide lacking the 24 amino acid N-terminal signal peptide.
SEQ ID NO: 31 sets forth an amino acid sequence of a rat erythropoietin receptor polypeptide.
SEQ ID NO: 32 sets forth an amino acid sequence of a truncated rat erythropoietin receptor polypeptide.
SEQ ID NO: 33 sets forth an amino acid sequence of a truncated rat erythropoietin receptor polypeptide.

SEQ ID NO: 34 sets forth an amino acid sequence of a rat erythropoietin receptor polypeptide lacking the 24 amino acid N-terminal signal peptide.

SEQ ID NO: 35 sets forth an amino acid sequence of a truncated rat erythropoietin receptor polypeptide lacking the 24 amino acid N-terminal signal peptide.

SEQ ID NO: 36 sets forth an amino acid sequence of a truncated rat erythropoietin receptor polypeptide lacking the 24 amino acid N-terminal signal peptide.

SEQ ID NO: 37 sets forth a polynucleotide sequence comprising an insulator sequence.

SEQ ID NO: 38 sets forth a polynucleotide sequence comprising an insulator sequence.

DETAILED DESCRIPTION

A. Overview

The present invention generally relates to improved gene therapy vectors and methods of using the same to treat, prevent, or ameliorate genetic disorders. One significant challenge for gene therapy is to maintain and/or expand corrected cell populations in subjects undergoing transplantation where the corrected cells do not have an intrinsic selective advantage over nontransduced cells. For example, in inherited hematopoietic disorders, e.g., sickle cell disease and β-thalassemia, limitations include, but are not limited to, inefficient transduction of hematopoietic stem or progenitor cells, the requirement for toxic myelosuppressive or myeloablative therapy, and a lack of optimal methods for in vivo selection of transduced cells.

The present invention is based, in part, on the unexpected discovery that the gene therapy vectors of the invention can be used to selectively or specifically, expand or increase the numbers of therapeutic cells in vitro, ex vivo, or in vivo to further increase the efficacy and specificity of gene therapy. Without wishing to be bound to any particular theory, the present invention contemplates, in part, that because the therapeutic cells carrying the vectors of the invention can be substantially expanded, fewer cells are required to provide therapeutic, preventive, or ameliorative endpoints for the subjects receiving the gene therapy. Moreover, because all of or at least a portion of cells carrying the vectors of the invention have a proliferative advantage over other cells, myelosuppressive or myeloablative therapy is not necessarily required to achieve therapeutic, preventive, or ameliorative endpoints.

Accordingly, the present invention addresses an unmet clinical need for improving the efficacy of gene therapy in the treatment of genetic diseases, whereby only a portion of cells have been effectively targeted by a vector but at levels that are insufficient for conferring a therapeutic, preventive, or ameliorative effect. The invention specifically relates to vectors, genetically engineered cells, and selective expansion the genetically engineered cells or a population of cells thereof, in vitro, ex vivo, or in vivo, to facilitate the desired outcome.

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., Molecular Cloning: A Laboratory Manual (2nd Edition, 1989); Maniatis et al., Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); A Practical Guide to Molecular Cloning (B. Perbal, ed., 1984).

All publications, patents and patent applications cited herein are hereby incorporated by reference in their entirety.

B. Definitions

Unless defined otherwise, all technical and scientific terms used herein have the same meaning as commonly understood by those of ordinary skill in the art to which the invention belongs. For the purposes of the present invention, the following terms are defined below.

As used herein, the term "retrovirus" refers to an RNA virus that reverse transcribes its genomic RNA into a linear double-stranded DNA copy and subsequently covalently integrates its genomic DNA into a host genome. Retroviruses are a common tool for gene delivery (Miller, 2000, Nature. 357: 455-460). Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), Spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred.

Retroviral vectors and more particularly lentiviral vectors may be used in practicing the present invention. Accordingly, the term "retrovirus" or "retroviral vector", as used herein is meant to include "lentivirus" and "lentiviral vectors" respectively.

The term "vector" is used herein to refer to a nucleic acid molecule capable transferring or transporting another nucleic acid molecule. The transferred nucleic acid is generally linked to, e.g., inserted into, the vector nucleic acid molecule.

A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses.

As will be evident to one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, including LTRs that are primarily derived from a lentivirus. The term "hybrid" refers to a vector, LTR or other nucleic acid containing both retroviral, e.g., lentiviral, sequences and non-lentiviral viral sequences. In one embodiment, a hybrid vector refers to a vector or transfer plasmid comprising retroviral e.g., lentiviral, sequences for reverse transcription, replication, integration and/or packaging.

In particular embodiments, the terms "lentiviral vector," "lentiviral expression vector" may be used to refer to lentiviral transfer plasmids and/or infectious lentiviral particles. Where reference is made herein to elements such as cloning sites, promoters, regulatory elements, heterologous nucleic acids, etc., it is to be understood that the sequences of these elements are present in RNA form in the lentiviral particles of the invention and are present in DNA form in the DNA plasmids of the invention.

At each end of the provirus are structures called "long terminal repeats" or "LTRs." The term "long terminal repeat (LTR)" refers to domains of base pairs located at the ends of retroviral DNAs which, in their natural sequence context, are direct repeats and contain U3, R and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R and U5. The U3 region contains the enhancer and promoter elements. The U5 region is the sequence between the primer binding site and the R region and contains the polyadenylation sequence. The R (repeat) region is flanked by the U3 and U5 regions. The LTR composed of U3, R and U5 regions and appears at both the 5' and 3' ends of the viral genome. Adjacent to the 5' LTR are sequences necessary for reverse transcription of the genome (the tRNA primer binding site) and for efficient packaging of viral RNA into particles (the Psi site).

As used herein, the term "packaging signal" or "packaging sequence" refers to sequences located within the retroviral genome which are required for insertion of the viral RNA into the viral capsid or particle, see e.g., Clever et al., 1995. J. of Virology, Vol. 69, No. 4; pp. 2101-2109. Several retroviral vectors use the minimal packaging signal (also referred to as the psi [Ψ] sequence) needed for encapsidation of the viral genome. Thus, as used herein, the terms "packaging sequence," "packaging signal," "psi" and the symbol "Ψ," are used in reference to the non-coding sequence required for encapsidation of retroviral RNA strands during viral particle formation.

In various embodiments, vectors comprise modified 5' LTR and/or 3' LTRs. Modifications of the 3' LTR are often made to improve the safety of lentiviral or retroviral systems by rendering viruses replication-defective. As used herein, the term "replication-defective" refers to virus that is not capable of complete, effective replication such that infective virions are not produced (e.g., replication-defective lentiviral progeny). The term "replication-competent" refers to wild-type virus or mutant virus that is capable of replication, such that viral replication of the virus is capable of producing infective virions (e.g., replication-competent lentiviral progeny). "Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication. This is because the right (3') LTR U3 region is used as a template for the left (5') LTR U3 region during viral replication and, thus, the viral transcript cannot be made without the U3 enhancer-promoter. In a further embodiment of the invention, the 3' LTR is modified such that the U5 region is replaced, for example, with an ideal poly(A) sequence. It should be noted that modifications to the LTRs such as modifications to the 3' LTR, the 5' LTR, or both 3' and 5' LTRs, are also included in the invention.

An additional safety enhancement is provided by replacing the U3 region of the 5' LTR with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system. In certain embodiments, the heterologous promoter has additional advantages in controlling the manner in which the viral genome is transcribed. For example, the heterologous promoter can be inducible, such that transcription of all or part of the viral genome will occur only when the induction factors are present. Induction factors include, but are not limited to, one or more chemical compounds or the physiological conditions such as temperature or pH, in which the host cells are cultured.

In some embodiments, viral vectors comprise a TAR element. The term "TAR" refers to the "trans-activation response" genetic element located in the R region of lentiviral (e.g., HIV) LTRs. This element interacts with the lentiviral trans-activator (tat) genetic element to enhance viral replication. However, this element is not required in embodiments wherein the U3 region of the 5' LTR is replaced by a heterologous promoter.

The "R region" refers to the region within retroviral LTRs beginning at the start of the capping group (i.e., the start of transcription) and ending immediately prior to the start of the poly A tract. The R region is also defined as being flanked by the U3 and U5 regions. The R region plays a role during reverse transcription in permitting the transfer of nascent DNA from one end of the genome to the other.

As used herein, the term "FLAP element" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou, et al., 2000, Cell, 101:173. During HIV-1 reverse transcription, central initiation of the plus-strand DNA at the central polypurine tract (cPPT) and central termination at the central termination sequence (CTS) lead to the formation of a three-stranded DNA structure: the HIV-1 central DNA flap.

While not wishing to be bound by any theory, the DNA flap may act as a cis-active determinant of lentiviral genome nuclear import and/or may increase the titer of the virus. In particular embodiments, the retroviral or lentiviral vector backbones comprise one or more FLAP elements upstream or downstream of the heterologous genes of interest in the vectors. For example, in particular embodiments a transfer plasmid includes a FLAP element. In one embodiment, a vector of the invention comprises a FLAP element isolated from HIV-1.

In one embodiment, retroviral or lentiviral transfer vectors comprise one or more export elements. The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. *J. Virol.* 65: 1053; and Cullen et al., 1991. *Cell* 58: 423), and the hepatitis B virus post-transcriptional regulatory element (HPRE). Generally, the RNA export element is placed within the 3' UTR of a gene, and can be inserted as one or multiple copies.

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid at the protein, e.g., woodchuck hepatitis virus posttranscriptional regulatory element (WPRE; Zufferey et al., 1999, *J. Virol.*, 73:2886); the posttranscriptional regulatory element present in hepatitis B virus (HPRE) (Huang et al., *Mol. Cell. Biol.*, 5:3864); and the like (Liu et al., 1995, *Genes Dev.*, 9:1766). In particular embodiments, vectors of the invention lack or do not comprise a posttranscriptional regulatory element such as a WPRE or HPRE because in some instances these elements increase the risk of cellular transformation and/or do not substantially or significantly increase the amount of mRNA transcript or increase mRNA stability. Therefore, in some embodiments, vectors of the invention lack or do not comprise a WPRE or HPRE as an added safety measure.

Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Efficient polyadenylation of the recombinant transcript is desirable as transcripts lacking a poly A tail are unstable and are rapidly degraded. Illustrative examples of polyA signals that can be used in a vector of the invention, includes an ideal polyA sequence (e.g., AATAAA, ATTAAA AGTAAA), a bovine growth hormone polyA sequence (BGHpA), a rabbit β-globin polyA sequence (rβgpA), or another suitable heterologous or endogenous polyA sequence known in the art.

In certain embodiments, a retroviral or lentiviral vector further comprises one or more insulator elements. Insulators elements may contribute to protecting lentivirus-expressed sequences, e.g., therapeutic polypeptides, from integration site effects, which may be mediated by cis-acting elements present in genomic DNA and lead to deregulated expression of transferred sequences (i.e., position effect; see, e.g., Burgess-Beusse et al., 2002, *Proc. Natl. Acad. Sci., USA*, 99:16433; and Zhan et al., 2001, *Hum. Genet.*, 109:471). In some embodiments, transfer vectors comprise one or more insulator element the 3' LTR and upon integration of the provirus into the host genome, the provirus comprises the one or more insulators at both the 5' LTR or 3' LTR, by virtue of duplicating the 3' LTR. Suitable insulators for use in the invention include, but are not limited to, the chicken β-globin insulator (see Chung et al., 1993. *Cell* 74:505; Chung et al., 1997. *PNAS* 94:575; and Bell et al., 1999. *Cell* 98:387, incorporated by reference herein). Examples of insulator elements include, but are not limited to, an insulator from an β-globin locus, such as chicken HS4.

According to certain specific embodiments of the invention, most or all of the viral vector backbone sequences are derived from a lentivirus, e.g., HIV-1. However, it is to be understood that many different sources of lentiviral sequences can be used, and numerous substitutions and alterations in certain of the lentiviral sequences may be accommodated without impairing the ability of a transfer vector to perform the functions described herein. Moreover, a variety of lentiviral vectors are known in the art, see Naldini et al., (1996a, 1996b, and 1998); Zufferey et al., (1997); Dull et al., 1998, U.S. Pat. Nos. 6,013,516; and 5,994,136, many of which may be adapted to produce a viral vector or transfer plasmid of the present invention.

As used herein, the terms "polynucleotide" or "nucleic acid" refers to messenger RNA (mRNA), RNA, genomic RNA (gRNA), plus strand RNA (RNA(+)), minus strand RNA (RNA(−)), genomic DNA (gDNA), complementary DNA (cDNA) or DNA. Polynucleotides include single and double stranded polynucleotides. Preferably, polynucleotides of the invention include polynucleotides or variants having at least about 50%, 55%, 60%, 65%, 70%, 75%, 80%, 85%, 90%, 95%, 96%, 97%, 98%, 99% or 100% sequence identity to any of the reference sequences described herein (see, e.g., Sequence Listing), typically where the variant maintains at least one biological activity of the reference sequence. In various illustrative embodiments, the present invention contemplates, in part, viral vector and transfer plasmid polynucleotide sequences and compositions comprising the same. In particular embodiments, the invention provides polynucleotides encoding one or more therapeutic polypeptides and/or other genes of interest.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms include polynucleotides in which one or more nucleotides have been added or deleted, or replaced with different nucleotides compared to a reference polynucleotide. In this regard, it is well understood in the art that certain alterations inclusive of mutations, additions, deletions and substitutions can be made to a reference polynucleotide whereby the altered polynucleotide retains the biological function or activity of the reference polynucleotide.

As used herein, the term "isolated" means material, e.g., a polynucleotide, a polypeptide, a cell, that is substantially or essentially free from components that normally accompany it in its native state. In particular embodiments, the term "obtained" or "derived" is used synonymously with isolated. For example, an "isolated polynucleotide," as used herein, refers to a polynucleotide that has been purified from the sequences which flank it in a naturally-occurring state, e.g., a DNA fragment that has been removed from the sequences that are normally adjacent to the fragment.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation.

The terms "complementary" and "complementarity" refer to polynucleotides (i.e., a sequence of nucleotides) related by the base-pairing rules. For example, the complementary strand of the DNA sequence 5' A G T C AT G 3' is 3' T C A G T A C 5'. The latter sequence is often written as the reverse complement with the 5' end on the left and the 3' end on the right, 5' C A T G A C T 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

The term "nucleic acid cassette" as used herein refers to genetic sequences within the vector which can express an RNA, and subsequently a polypeptide. In one embodiment, the nucleic acid cassette contains a gene(s)-of-interest, e.g., a polynucleotide(s)-of-interest. In another embodiment, the nucleic acid cassette contains one or more expression control sequences and a gene(s)-of-interest, e.g., a polynucleotide(s)-of-interest. Vectors may comprise one, two, three, four, five or more nucleic acid cassettes. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. In a preferred embodiment of the invention, the nucleic acid cassette contains the sequence of a therapeutic gene used to treat, prevent, or ameliorate a genetic disorder, such as a hematopoietic disorder. The cassette can be removed and inserted into a plasmid or viral vector as a single unit.

Polynucleotides include a polynucleotide(s)-of-interest. As used herein, the term "polynucleotide(s)-of-interest" refers to one or more polynucleotides, e.g., a polynucleotide encoding a polypeptide (i.e., a polypeptide-of-interest), inserted into an expression vector that is desired to be expressed. In preferred embodiments, vectors and/or plasmids of the present invention comprise one or more polynucleotides-of-interest or other polynucleotide sequences that encode a polypeptide whose expression is desired, e.g., a truncated erythropoietin receptor. In certain embodiments, a polynucleotide-of-interest encodes a polypeptide that provides a therapeutic effect in the treatment, prevention, or amelioration of a disease or disorder, which may be referred to as a "therapeutic polypeptide," e.g., a globin gene. See, e.g., SEQ ID NOs: 2-4, 6-9, 11-13, and 15.

The term "globin" is used here to mean all proteins or protein subunits that are capable of covalently or noncovalently binding a heme moiety, and can therefore transport or store oxygen. Subunits of vertebrate and invertebrate hemoglobins, vertebrate and invertebrate myoglobins or mutants thereof are included by the term globin. Examples of globins include α-globin or variant thereof, β-globin or variant thereof, γ-globin or a variant thereof, and δ-globin.

In one embodiment, the polynucleotide-of-interest is a gene that encodes a polypeptide that provides a therapeutic function for the treatment of a hemoglobinopathy, e.g., α-globin, β-globin or β-globin$^{A-T87Q}$. Polynucleotides-of-interest, and polypeptides encoded therefrom, include both polynucleotides that encode wild-type polypeptides, as well as functional variants and fragments thereof. In particular embodiments, a functional variant has at least 80%, at least 90%, at least 95%, or at least 99% identity to a corresponding wild-type reference polynucleotide or polypeptide sequence. In certain embodiments, a functional variant or fragment has at least 50%, at least 60%, at least 70%, at least 80%, or at least 90% of a biological activity of a corresponding wild-type polypeptide. Representative polynucleotides sequences suitable for use in the present invention include, but are not limited to, polynucleotides encoding α-globin, β-globin, β-globin$^{A-T87Q}$, and various truncated erythropoietin receptors, e.g., SEQ ID NOs: 20, 21, 23, 24, 26, 27, 29, 30, 32, 33, 35, and 36.

The polynucleotides of the present invention, regardless of the length of the coding sequence itself, may be combined with other DNA sequences, such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, with the total length preferably being limited by the ease of preparation and use in the intended recombinant DNA protocol.

The term "expression control sequence" refers to a polynucleotide sequence that comprises one or more promoters, enhancers, or other transcriptional control elements or combinations thereof that are capable of directing, increasing, regulating, or controlling the transcription or expression of an operatively linked polynucleotide. In particular embodiments, vectors of the invention comprise one or more expression control sequences that are specific to particular cells, cell types, or cell lineages e.g., target cells; that is, expression of polynucleotides operatively linked to an expression control sequence specific to particular cells, cell types, or cell lineages is expressed in target cells and not in other non-target cells. Each one of the one or more expression control sequences in a vector that are cell specific may express in the same or different cell types depending on the therapy desired. In preferred embodiments, vectors comprise one or more expression control sequences specific to hematopoietic cells, e.g., hematopoietic stem or progenitor cells. In other preferred embodiments, vectors comprise one or more expression control sequences specific to erythroid cells.

The term "promoter" as used herein refers to a recognition site of a polynucleotide (DNA or RNA) to which an RNA polymerase binds. The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

In particular embodiments, a vector of the invention comprises exogenous, endogenous, or heterologous control sequences such as promoters and/or enhancers. An "endogenous" control sequence is one which is naturally linked to a given gene in the genome. An "exogenous" control sequence is one which is placed in juxtaposition to a gene by means of genetic manipulation (i.e., molecular biological techniques) such that transcription of that gene is directed by the linked enhancer/promoter. A "heterologous" control sequence is an exogenous sequence that is from a different species than the cell being genetically manipulated.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer or other expression control sequence) and a second polynucleotide sequence, e.g., a polynucleotide-of-interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively. Illustrative ubiquitous expression control sequences include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPAS), heat shock protein 90 kDa beta, member 1 (HSP90B1), heat shock protein 70 kDa (HSP70), β-kinesin (β-KIN), the human ROSA 26 locus (Irions et al., Nature Biotechnology 25, 1477-1482 (2007)), a Ubiquitin C promoter (UBC), a phosphoglycerate kinase-1 (PGK) promoter, a cytomegalovirus enhancer/chicken β-actin (CAG) promoter, and a β-actin promoter.

In a particular embodiment, it may be desirable to use a cell, cell type, cell lineage or tissue specific expression control sequence to achieve cell type specific, lineage specific, or tissue specific expression of a desired polynucleotide sequence (e.g., to express a particular nucleic acid encoding a polypeptide in only a subset of cell types, cell lineages, or tissues or during specific stages of development). Illustrative examples of cell, cell type, cell lineage or tissue specific expression control sequences include, but are not limited to: an B29 promoter (B cell expression), a runt transcription factor (CBFa2) promoter (stem cell expression), an CD14 promoter (monocytic cell expression), an CD43 promoter (leukocyte and platelet expression), an CD45 promoter (hematopoietic cell expression), an CD68 promoter (macrophage expression), an endoglin promoter (endothelial cell expression), a fms-related tyrosine kinase 1 (FLT1) promoter (endothelial cell expression), an integrin, alpha 2b (ITGA2B) promoter (megakaryocyte expression), an intracellular adhesion molecule 2 (ICAM-2) promoter (endothelial cell expression), an interferon beta (IFN-β) promoter (hematopoietic cell expression), a β-globin LCR (erythroid cell expression), a globin promoter (erythroid cell expression), a β-globin promoter (erythroid cell expression), an α-globin HS40 enhancer (erythroid cell expression), an ankyrin-1 promoter (erythroid cell expression), and a Wiskott-Aldrich syndrome protein (WASP) promoter (hematopoietic cell expression).

In one embodiment, a vector of the present invention comprises one or more cell or tissue specific promoters and/or enhancers selected from the group consisting of: a human β-globin promoter; a human β-globin LCR; and a human α-globin HS40 enhancer and an ankyrin-1 promoter.

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments of the invention provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, Gene, 323:67), the cumate inducible gene switch (WO 2002/088346), tetracycline-dependent regulatory systems, etc.

Conditional expression can also be achieved by using a site specific DNA recombinase. According to certain embodiments of the invention the vector comprises at least one (typically two) site(s) for recombination mediated by a site specific recombinase. As used herein, the terms "recombinase" or "site specific recombinase" include excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Illustrative examples of recombinases suitable for use in particular embodiments of the present invention include, but are not limited to: Cre, Int, IHF, Xis, Flp, Fis, Hin, Gin, ΦC31, Cin, Tn3 resolvase, TndX, XerC, XerD, TnpX, Hjc, Gin, SpCCE1, and ParA.

The vectors may comprise one or more recombination sites for any of a wide variety of site specific recombinases. It is to be understood that the target site for a site specific recombinase is in addition to any site(s) required for integration of a vector, e.g., a retroviral vector or lentiviral vector. As used herein, the terms "recombination sequence," "recombination site," or "site specific recombination site" refer to a particular nucleic acid sequence to which a recombinase recognizes and binds.

For example, one recombination site for Cre recombinase is loxP which is a 34 base pair sequence comprising two 13 base pair inverted repeats (serving as the recombinase binding sites) flanking an 8 base pair core sequence (see FIG. 1 of Sauer, B., *Current Opinion in Biotechnology* 5:521-527 (1994)). Other exemplary loxP sites include, but are not limited to: lox511 (Hoess et al., 1996; Bethke and Sauer, 1997), lox5171 (Lee and Saito, 1998), lox2272 (Lee and Saito, 1998), m2 (Langer et al., 2002), lox71 (Albert et al., 1995), and lox66 (Albert et al., 1995).

Suitable recognition sites for the FLP recombinase include, but are not limited to: FRT (McLeod, et al., 1996), $F_1$, $F_2$, $F_3$ (Schlake and Bode, 1994), $F_4$, $F_5$ (Schlake and Bode, 1994), FRT(LE) (Senecoff et al., 1988), FRT(RE) (Senecoff et al., 1988).

Other examples of recognition sequences are the attB, attP, attL, and attR sequences, which are recognized by the recombinase enzyme λ Integrase, e.g., phi-c31. The φC31 SSR mediates recombination only between the heterotypic sites attB (34 bp in length) and attP (39 bp in length) (Groth et al., 2000). attB and attP, named for the attachment sites for the phage integrase on the bacterial and phage genomes, respectively, both contain imperfect inverted repeats that are likely bound by φC31 homodimers (Groth et al., 2000). The product sites, attL and attR, are effectively inert to further φC31-mediated recombination (Belteki et al., 2003), making the reaction irreversible. For catalyzing insertions, it has been found that attB-bearing DNA inserts into a genomic attP site more readily than an attP site into a genomic attB site (Thyagarajan et al., 2001; Belteki et al., 2003). Thus, typical strategies position by homologous recombination an attP-bearing "docking site" into a defined locus, which is then partnered with an attB-bearing incoming sequence for insertion.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15(12):477-83) and Jackson and Kaminski. 1995. *RNA* 1(10):985-1000. In particular embodiments, the vectors contemplated by the invention, include one or more polynucleotides-of-interest that encode one or more polypeptides. In particular embodiments, to achieve efficient translation of each of the plurality of polypeptides, the polynucleotide sequences can be separated by one or more IRES sequences or polynucleotide sequences encoding self-cleaving polypeptides.

As used herein, the term "Kozak sequence" refers to a short nucleotide sequence that greatly facilitates the initial binding of mRNA to the small subunit of the ribosome and increases translation. The consensus Kozak sequence is (GCC)RCCATGG, where R is a purine (A or G) (Kozak, 1986. *Cell.* 44(2):283-92, and Kozak, 1987. *Nucleic Acids Res.* 15(20):8125-48). In particular embodiments, the vectors contemplated by the invention, comprise polynucleotides that have a consensus Kozak sequence and that encode a desired polypeptide.

In certain embodiments, vectors comprise a selection gene, also termed a selectable marker. Typical selection genes encode proteins that (a) confer resistance to antibiotics or other toxins, e.g., ampicillin, neomycin, hygromycin, methotrexate, Zeocin, Blasticidin, or tetracycline, (b) complement auxotrophic deficiencies, or (c) supply critical nutrients not available from complex media, e.g., the gene encoding D-alanine racemase for Bacilli. Any number of selection systems may be used to recover transformed cell lines. These include, but are not limited to, the herpes simplex virus thymidine kinase (Wigler et al., 1977. *Cell* 11:223-232) and adenine phosphoribosyltransferase (Lowy et al., 1990. *Cell* 22:817-823) genes which can be employed in tk- or aprt-cells, respectively.

In various embodiments, vectors of the invention are used to increase, establish and/or maintain the expression of one or more polypeptides, e.g., globins, EpoRs, in cell. The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

Particular embodiments of the invention also include polypeptide "variants." The recitation polypeptide "variant" refers to polypeptides that are distinguished from a reference polypeptide by the addition, deletion, truncations, and/or substitution of at least one amino acid residue, and that retain a biological activity. In certain embodiments, a polypeptide variant is distinguished from a reference polypeptide by one or more substitutions, which may be conservative or non-conservative, as known in the art.

In certain embodiments, a variant polypeptide includes an amino acid sequence having at least about 50%, 55%, 60%, 65%, 70%, 75%, 80%, 85%, 90%, 91%, 92%, 93%, 94%, 95%, 96%, 97%, 98%, 99% or more sequence identity or similarity to a corresponding sequence of a reference polypeptide. In certain embodiments, the amino acid additions or deletions occur at the C-terminal end and/or the N-terminal end of the reference polypeptide. In certain embodiments, the amino acid deletions include C-terminal truncations of about 1, about 2, about 3, about 4, about 5, about 6, about 7, about 8, about 9, about 10, about 15, about 20, about 25, about 30, about 35, about 40, about 45, 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, or about 175 or more amino acids, including all intervening numbers of amino acids, e.g., 25, 26, 27, 29, 30 . . . 100, 101, 102, 103, 104, 105 . . . 170, 171, 172, 173, 174, etc.

As noted above, polypeptides of the invention may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873,192, Watson, J. D. et al., (*Molecular Biology of the Gene*, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure* (Natl. Biomed. Res. Found., Washington, D.C.).

A "host cell" includes cells transfected, infected, or transduced in vivo, ex vivo, or in vitro with a recombinant vector or a polynucleotide of the invention. Host cells may include packaging cells, producer cells, and cells infected with viral vectors. In particular embodiments, host cells infected with viral vector of the invention are administered to a subject in need of therapy. In certain embodiments, the term "target cell" is used interchangeably with host cell and refers to transfected, infected, or transduced cells of a desired cell type. In preferred embodiments, the target cell is a hematopoietic cell, e.g., a hematopoietic stem or progenitor cell.

Large scale viral particle production is often necessary to achieve a reasonable viral titer. Viral particles are produced by transfecting a transfer vector into a packaging cell line that comprises viral structural and/or accessory genes, e.g., gag, pol, env, tat, rev, vif, vpr, vpu, vpx, or nef genes or other retroviral genes.

As used herein, the term "packaging vector" refers to an expression vector or viral vector that lacks a packaging signal and comprises a polynucleotide encoding one, two, three, four or more viral structural and/or accessory genes. Typically, the packaging vectors are included in a packaging cell, and are introduced into the cell via transfection, transduction or infection. Methods for transfection, transduction or infection are well known by those of skill in the art. A retroviral/lentiviral transfer vector of the present invention can be introduced into a packaging cell line, via transfection, transduction or infection, to generate a producer cell or cell line. The packaging vectors of the present invention can be introduced into human cells or cell lines by standard methods including, e.g., calcium phosphate transfection, lipofection or electroporation. In some embodiments, the packaging vectors are introduced into the cells together with a dominant selectable marker, such as neomycin, hygromycin, puromycin, blasticidin, zeocin, thymidine kinase, DHFR, Gln synthetase or ADA, followed by selection in the presence of the appropriate drug and isolation of clones. A selectable marker gene can be linked physically to genes encoding by the packaging vector, e.g., by IRES or self cleaving viral peptides.

Viral envelope proteins (env) determine the range of host cells which can ultimately be infected and transformed by recombinant retroviruses generated from the cell lines. In the case of lentiviruses, such as HIV-1, HIV-2, SIV, FIV and EIV, the env proteins include gp41 and gp120. Preferably, the viral env proteins expressed by packaging cells of the invention are encoded on a separate vector from the viral gag and pol genes, as has been previously described.

Illustrative examples of retroviral-derived env genes which can be employed in the invention include, but are not limited to: MLV envelopes, 10A1 envelope, BAEV, FeLV-B, RD114, SSAV, Ebola, Sendai, FPV (Fowl plague virus), and influenza virus envelopes. Similarly, genes encoding envelopes from RNA viruses (e.g., RNA virus families of Picornaviridae, Calciviridae, Astroviridae, Togaviridae, Flaviviridae, Coronaviridae, Paramyxoviridae, Rhabdoviridae, Filoviridae, Orthomyxoviridae, Bunyaviridae, Arenaviridae, Reoviridae, Birnaviridae, Retroviridae) as well as from the DNA viruses (families of Hepadnaviridae, Circoviridae, Parvoviridae, Papovaviridae, Adenoviridae, Herpesviridae, Poxyiridae, and Iridoviridae) may be utilized. Representative examples include , FeLV, VEE, HFVW, WDSV, SFV, Rabies, ALV, BIV, BLV, EBV, CAEV, SNV, ChTLV, STLV, MPMV, SMRV, RAV, FuSV, MH2, AEV, AMV, CT10, and EIAV.

In other embodiments, envelope proteins for pseudotyping a virus of present invention include, but are not limited to any of the following virus: Influenza A such as H1N1, H1N2, H3N2 and H5N1 (bird flu), Influenza B, Influenza C virus, Hepatitis A virus, Hepatitis B virus, Hepatitis C virus, Hepatitis D virus, Hepatitis E virus, Rotavirus, any virus of the Norwalk virus group, enteric adenoviruses, parvovirus, Dengue fever virus, Monkey pox, Mononegavirales, Lyssavirus such as rabies virus, Lagos bat virus, Mokola virus, Duvenhage virus, European bat virus 1 & 2 and Australian bat virus, Ephemerovirus, Vesiculovirus, Vesicular Stomatitis Virus (VSV), Herpesviruses such as Herpes simplex virus types 1 and 2, varicella zoster, cytomegalovirus, Epstein-Bar virus (EBV), human herpesviruses (HHV), human herpesvirus type 6 and 8, Human immunodeficiency virus (HIV), papilloma virus, murine gammaherpesvirus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridae such as Crimean-Congo hemorrhagic fever virus, Hantavirus, hemorrhagic fever with renal syndrome causing virus, Rift Valley fever virus, Filoviridae (filovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-CoV), West Nile virus, any encephaliltis causing virus.

In one embodiment, the invention provides packaging cells which produce recombinant retrovirus, e.g., lentivirus, pseudotyped with the VSV-G glycoprotein.

The terms "pseudotype" or "pseudotyping" as used herein, refer to a virus whose viral envelope proteins have been substituted with those of another virus possessing preferable characteristics. For example, HIV can be pseudotyped with vesicular stomatitis virus G-protein (VSV-G) envelope proteins, which allows HIV to infect a wider range of cells because HIV envelope proteins (encoded by the env gene) normally target the virus to CD4+ presenting cells. In a preferred embodiment of the invention, lentiviral envelope proteins are pseudotyped with VSV-G. In one embodiment, the invention provides packaging cells which produce recombinant retrovirus, e.g., lentivirus, pseudotyped with the VSV-G envelope glycoprotein.

As used herein, the term "packaging cell lines" is used in reference to cell lines that do not contain a packaging signal, but do stably or transiently express viral structural proteins and replication enzymes (e.g., gag, pol and env) which are necessary for the correct packaging of viral particles. Any suitable cell line can be employed to prepare packaging cells of the invention. Generally, the cells are mammalian cells. In a particular embodiment, the cells used to produce the packaging cell line are human cells. Suitable cell lines which can be used include, for example, CHO cells, BHK cells, MDCK cells, C3H 10T1/2 cells, FLY cells, Psi-2 cells, BOSC 23 cells, PA317 cells, WEHI cells, COS cells, BSC 1 cells, BSC 40 cells, BMT 10 cells, VERO cells, W138 cells, MRC5 cells, A549 cells, HT1080 cells, 293 cells, 293T cells, B-50 cells, 3T3 cells, NIH3T3 cells, HepG2 cells, Saos-2 cells, Huh7 cells, HeLa cells, W163 cells, 211 cells, and 211A cells. In preferred embodiments, the packaging cells are 293 cells, 293T cells, or A549 cells. In another preferred embodiment, the cells are A549 cells.

As used herein, the term "producer cell line" refers to a cell line which is capable of producing recombinant retroviral particles, comprising a packaging cell line and a transfer vector construct comprising a packaging signal. The production of infectious viral particles and viral stock solutions may be carried out using conventional techniques. Methods of preparing viral stock solutions are known in the art and are illustrated by, e.g., Y. Soneoka et al. (1995) *Nucl. Acids Res.* 23:628-633, and N. R. Landau et al. (1992) *J. Virol.* 66:5110-5113. Infectious virus particles may be collected from the packaging cells using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art.

The delivery of a gene(s) or other polynucleotide sequence using a retroviral or lentiviral vector by means of viral infection rather than by transfection is referred to as "transduction." In one embodiment, retroviral vectors are transduced into a cell through infection and provirus integration. In certain embodiments, a cell, e.g., a target cell, is "transduced" if it comprises a gene or other polynucleotide sequence delivered to the cell by infection using a viral or retroviral vector. In particular embodiments, a transduced cell comprises one or more genes or other polynucleotide sequences delivered by a retroviral or lentiviral vector in its cellular genome.

In particular embodiments, host cells transduced with viral vector of the invention that expresses one or more polypeptides, are administered to a subject to treat and/or prevent a hematopoietic disease, disorder, or condition. Other methods relating to the use of viral vectors in gene therapy, which may be utilized according to certain embodiments of the present invention, can be found in, e.g., Kay, M. A. (1997) *Chest* 111(6 Supp.):1385-142S; Ferry, N. and Heard, J. M. (1998) *Hum. Gene Ther.* 9:1975-81; Shiratory, Y. et al. (1999) *Liver* 19:265-74; Oka, K. et al. (2000) *Curr. Opin. Lipidol.* 11:179-86; Thule, P. M. and Liu, J. M. (2000) *Gene Ther.* 7:1744-52; Yang, N. S. (1992) *Crit. Rev. Biotechnol.* 12:335-56; Alt, M. (1995) *J. Hepatol.* 23:746-58; Brody, S. L. and Crystal, R. G. (1994) *Ann. N.Y. Acad. Sci.* 716:90-101; Strayer, D. S. (1999) *Expert Opin. Investig. Drugs* 8:2159-2172; Smith-Arica, J. R. and Bartlett, J. S. (2001) *Curr. Cardiol. Rep.* 3:43-49; and Lee, H. C. et al. (2000) *Nature* 408:483-8.

By "enhance" or "promote," or "increase" or "expand" refers generally to the ability of a vector of the invention or host cell transduced with a vector of the invention to produce, elicit, or cause a greater physiological response (i.e., downstream effects) in a particular cell type or specific cell lineage compared to the response caused by either vehicle or a control molecule/composition, or in other cell types or specific cell lineages. A measurable physiological response may include an increase in cell expansion, engraftment, viability, homing, and/or self-renewal, among others apparent from the understanding in the art and the description herein. In one embodiment, wherein a hematopoietic stem cell transduced with a vector of the invention gives rise to progenitor cells, the increase comprises an increase in the number of progenitor cells of one lineage, e.g., erythroid lineage, compared to other cell lineages. Increases in hematopoietic stem and/or progenitor cell engraftment, viability, homing, self-renewal and/or in vivo expansion, can be ascertained using methods known in the art, such as gene expression, CFU-C assays, CFU-S assays, CAFC assays, and cell surface protein expression, among others. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle, a control composition, or the response in a particular cell lineage.

By "decrease" or "lower," or "lessen," or "reduce," or "abate" refers generally to the ability of a vector of the invention or host cell transduced with a vector of the invention to produce, elicit, or cause a lesser physiological response (i.e., downstream effects) in a particular cell type or specific cell lineage compared to the response caused by either vehicle or a control molecule/composition, or in other cell types or specific cell lineages. A "decrease" or "reduced" amount is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition, or the response in a particular cell lineage.

By "maintain," or "preserve," or "maintenance," or "no change," or "no substantial change," or "no substantial decrease" refers generally to the ability of a vector of the invention or host cell transduced with a vector of the invention to produce, elicit, or cause a lesser physiological response (i.e., downstream effects) in a cell, as compared to the response caused by either vehicle, a control molecule/composition, or the response in a particular cell lineage. A comparable response is one that is not significantly different or measurable different from the reference response.

The articles "a, " "an, " and "the" are used herein to refer to one or to more than one (i.e. to at least one) of the grammatical object of the article. By way of example, "an element" means one element or more than one element.

The use of the alternative (e.g., "or") should be understood to mean either one, both, or any combination thereof of the alternatives. As used herein, the terms "include" and "comprise" are used synonymously.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

In the following description, certain specific details are set forth in order to provide a thorough understanding of various embodiments of the invention. However, one skilled in the art will understand that the invention may be practiced without these details. In addition, it should be understood that the individual vectors, or groups of vectors, derived from the various combinations of the structures and substituents described herein, are disclosed by the present application to the same extent as if each vector or group of vectors was set forth individually. Thus, selection of particular vector structures or particular substituents is within the scope of the present disclosure.

C. Viral Vectors

Retroviral and lentiviral vectors have been tested and found to be suitable delivery vehicles for the stable introduction of genes of interest into the genome of a broad range of target cells. The present invention contemplates, in part, gene therapy vectors that can be used to deliver one or more genes to a cell, to both increase expression of the polypeptide encoded by the gene in the cell and to increase or expand a particular population or lineage of cells comprising the vector. In this way, the vectors of the invention offer numerous therapeutic, prophylatic, and ameliorative advantages compared to existing vectors that do not simultaneously increase polypeptide expression in a cell and increase specific cell lineages comprising the vector.

The present invention further provides transfer vectors, which may be used to practice methods of the present invention. While the skilled artisan will appreciate that such transfer vectors may be produced using a variety of different viral vectors, in particular embodiments, the transfer vector is a retroviral vector or a lentiviral vector, in part since lentiviral vectors are capable of providing efficient delivery, integration and long term expression of transgenes into non-dividing cells both in vitro and in vivo. A variety of lentiviral vectors are known in the art, see Naldini et al., (1996a, 1996b, and 1998); Zufferey et al., (1997); Dull et al., 1998, U.S. Pat. Nos. 6,013,516; and 5,994,136, any of which may be adapted to produce a transfer vector of the present invention. In general, these vectors are plasmid-based or virus-based, and are configured to carry the essential sequences for transfer of a nucleic acid encoding a therapeutic polypeptide into a host cell.

In illustrative embodiments, the lentiviral vector is an HIV vector. Thus, the vectors may be derived from human immunodeficiency-1 (HIV-1), human immunodeficiency-2 (HIV-2), simian immunodeficiency virus (SIV), feline immunodeficiency virus (FIV), bovine immunodeficiency virus (BIV), Jembrana Disease Virus (JDV), equine infectious anemia virus (EIAV), caprine arthritis encephalitis virus (CAEV) and the like. HIV based vector backbones (i.e., HIV cis-acting sequence elements and HIV gag, pol and rev genes) are generally be preferred in connection with most aspects of the present invention in that HIV-based constructs are the most efficient at transduction of human cells.

Although particular illustrative embodiments include more detailed description of vectors, compositions and methods used to correct hematopoietic disorders, e.g., hemoglobinopathies, the invention should not be considered to be limited by this disclosure. One having skill in the art would readily appreciate that the principles illustrated herein can be applied to gene therapy in other systems, e.g., nervous system, including the eye, central nervous system, and peripheral nervous system; the circulatory system; the muscular system; the skeletal system; organs, including the skin, heart, lungs, pancreas, liver, kidney, intestine, and the like.

In one embodiment, the present invention provides vectors, e.g., lentiviral vectors, that comprise an expression control sequence that directs expression of polynucleotide-of-interest in a particular cell type or cell lineage, and another expression control sequence operably linked to a truncated erythropoietin receptor. Without wishing to be bound to any particular theory, the present invention contemplates, in part, that the expression control sequence operatively linked to a truncated erythropoietin receptor, in the presence of a suitable EpoR agonist, allows for an expansion of or an increase in cells which express the truncated erythropoietin receptor. In addition, the use of a cell type or cell lineage expression control sequence offers safety advantages in restricting polynucleotide expression to a desired stage of cell differentiation in a single lineage; and thus, vectors of the invention alleviate concerns dealing with ectopic expression of polypeptides in undesired cells types.

In one embodiment, the expression control sequence operably linked to the therapeutic gene or polynucleotide-of-interest need not be the same expression control sequence or an expression control sequence that elicits expression in the same cell type or cell lineage as the expression control sequence operably linked to the truncated erythropoietin receptor. In another embodiment, the expression control sequence operably linked to the therapeutic gene or polynucleotide-of-interest elicits expression in the same cell type or cell lineage as a different expression control sequence operably linked to the truncated erythropoietin receptor. In further embodiment, the expression control sequence operably linked to the therapeutic gene or polynucleotide-of-interest elicits expression in the same cell type or cell lineage is the same as the expression control sequence operably linked to the truncated erythropoietin receptor.

In one non-limiting example, ubiquitous expression of the erythropoietin receptor would allow for expanding or increasing the cells in which it is expressed, i.e., all cells. Illustrative ubiquitous expression control sequences that direct ubiquitous expression of the truncated erythropoietin receptor include, but are not limited to: a cytomegalovirus immediate early gene promoter (CMV), an elongation factor 1 alpha promoter (EF1-α), a phosphoglycerate kinase-1 promoter (PGK), a ubiquitin-C promoter (UBQ-C), a cytomegalovirus enhancer/chicken beta-actin promoter (CAG), polyoma enhancer/herpes simplex thymidine kinase promoter (MC1), a beta actin promoter (β-ACT), and a simian virus 40 promoter (SV40).

In another non-limiting example, conditional expression of the erythropoietin receptor would allow for expanding or increasing the cells in which it is conditionally expressed.

In yet another non-limiting example, stem cell specific expression of the truncated erythropoietin receptor would allow for expanding or increasing the stem cells (and all cell lineages derived from the stem cells) in which it is expressed, e.g., hematopoietic stem cells. Illustrative stem cell specific expression control sequences that direct stem cell specific expression of the truncated erythropoietin receptor include, but are not limited to: an embryonic stem cell promoter, a neural stem cell promoter, a mesenchymal stem cell promoter, a liver stem cell promoter, a pancreatic stem cell promoter, a cardiac stem cell promoter, a kidney stem cell promoter, and a hematopoietic stem cell promoter.

In yet another non-limiting example, a cell type or cell lineage specific expression of the truncated erythropoietin receptor would allow for expanding or increasing a particular cell type or cell lineage in which it is expressed, e.g., a target cell type or cell lineage, compared to another cell type or cell lineage, e.g., a non-target cell type or cell lineage. Illustrative cell type or cell lineage specific expression control sequences that direct expression of the truncated erythropoietin receptor include, but are not limited to: a hematopoietic stem cell promoter, a hematopoietic progenitor cell promoter, a myeloid cell promoter, a lymphoid cell promoter, a thrombopoietic lineage promoter, a mast cell promoter, an erythropoietic lineage promoter, a granulopoietic lineage promoter, and a monocytopoietic lineage promoter.

Illustrative target cell lineages include the hematopoietic cell lineage, the myeloid lineage, the lymphoid lineage, the thrombopoietic lineage, the erythropoietic lineage, the granulopoietic lineage promoter, and the monocytopoietic lineage. In preferred embodiments, the target cell lineage is the erythropoietic cell lineage.

Illustrative target cell types include hematopoietic stem cells, hematopoietic progenitor cells, myeloid progenitors, lymphoid progenitors, thrombopoietic progenitors, erythroid progenitors, granulopoietic progenitors, monocytopoietic progenitors, megakaryoblasts, promegakaryocytes, megakaryocytes, thrombocytes/platelets, proerythroblasts, basophilic erythroblasts, polychromatic erythroblasts, orthochromatic erythroblasts, polychromatic erythrocytes, erythrocytes (RBCs), basophilic promyelocytes, basophilic myelocytes, basophilic metamyelocytes, basophils, neutrophilic promyelocytes, neutrophilic myelocytes, neutrophilic metamyelocytes, neutrophils, eosinophilic promyelocytes, eosinophilic myelocytes, macrophages, dendritic cells, lymphoblasts, prolymphocytes, natural killer (NK)-cells, small lymphocytes, T-lymphocytes, B-lymphocytes, plasma cells, and lymphoid dendritic cells. In preferred embodiments, the target cell type is one or more erythroid cells, e.g., proerythroblast, basophilic erythroblast, polychromatic erythroblast, orthochromatic erythroblast, polychromatic erythrocyte, and erythrocyte (RBC).

In particular embodiments, a vector of the invention may be used to increase expression of a polynucleotide, e.g., gene-of-interest in one or more or all hematopoietic cells and amplify or increase the numbers of one or more cell types, e.g., hematopoietic stem cell. In one embodiment, the vector comprises a hematopoietic cell promoter, enhancer, or promoter/enhancer operably linked to a gene of interest and an ubiquitous conditional, or cell type or cell lineage specific promoter, enhancer, or promoter/enhancer operably linked to a truncated erythropoietin receptor (tEpoR). In another embodiment, the vector comprises one or more retroviral LTRs, a hematopoietic cell expression control sequence operably linked to a gene of interest and an ubiquitous, conditional, or cell lineage specific expression control sequence operably linked to a truncated erythropoietin receptor (tEpoR).

Suitable cell type or cell lineage specific expression control sequences include, but are not limited to hematopoietic cell expression control sequences, such as, for example, a hematopoietic stem cell promoter, and a hematopoietic progenitor cell promoter. In embodiments where expression of the gene of interest and/or tEpoR is desired in one or more erythroid cells, a suitable hematopoietic cell expression control sequence can include, but is not limited to, an erythroid cell specific promoter and optionally an erythroid cell specific enhancer, a human β-globin promoter, a human β-globin LCR, or a human α-globin HS40 enhancer and an ankyrin-1 promoter.

The use of a cell type or cell lineage expression control sequence offers safety advantages in restricting polynucleotide expression to this a desired stage of cell differentiation in a single lineage; and thus, vectors of the invention alleviate concerns dealing with ectopic expression of polypeptides in undesired cells types. In one embodiment, the invention provides, a vector comprising one or more LTRs, a first erythroid cell specific expression control sequence operably linked to a gene of interest and a second erythroid cell specific expression control sequence operably linked to a tEpoR. The first and second erythroid cell specific expression control sequences can each be independently selected from the group consisting of: a human β-globin promoter; a human β-globin LCR; and a human α-globin HS40 enhancer and an ankyrin-1 promoter.

In various embodiments, the design of the vector will be made with the goal of treating, preventing, or ameliorating a particular hematopoietic disease, disorder, or condition. For example, the present invention contemplates vectors for gene therapy of hemoglobinopathies that comprise a gene of interest selected from the group consisting of: human α-globin, human β-globin, human δ-globin, and human γ-globin, or biologically variants or fragments thereof. In one embodiment, the globin gene is selected from the group consisting of a wild type human β-globin gene, a deleted human β-globin gene comprising one or more deletions of intron sequences, and a mutated human β-globin gene encoding at least one antisickling amino acid residue.

In a particular embodiment, wherein the condition being treated is a sickle cell hemoglobinopathy, the gene of interest can be an antisickling protein. As used herein, "antisickling protein" refers to a polypeptide that prevents or reverses the pathological events leading to sickling of erythrocytes in sickle cell conditions. In one embodiment of the invention, the transduced cells of the invention are used to deliver antisickling proteins to a subject with a hemoglobinopathic condition. Antisickling proteins also include mutated β-globin genes comprising antisickling amino acid residues.

In a preferred embodiment, one such globin variant is the human βA-globin gene encoding a threonine to glutamine mutation at codon 87 ($\beta^{A-T87Q}$) or a human βA-globin gene. Other antisickling amino acid residues are known in the art and may be useful in the present invention. For example, see U.S. Pat. Nos. 6,051,402; 5,861,488; 6,670,323; 5,864,029; 5,877,288; and Levasseur et al., *Blood* 102:4312-4319 (2003), which are herein incorporated by reference.

In certain embodiments, a vector that comprising an erythroid specific expression control sequence is used to treat, prevent, or ameliorate of a vast number of disorders extending well beyond the hemoglobinopathies. Red blood cell precursors are a useful cell population in which to express polypeptides that can be secreted into the circulation and thus delivered systemically. An example of such in vivo protein delivery is human Factor IX, a clotting factor that is missing in patients with Hemophilia B, see, e.g., A. H. Chang, et al., *Molecular Therapy* (2008), which is herein incorporated by reference.

In one embodiment, cells transduced with vectors of the invention can be used as "factories" for protein secretion, in vitro, ex vivo, or in vivo. For example, a vector comprising an erythroid cell specific expression control sequence can be used for large-scale in vitro production of proteins from erythroid cells differentiated from HSCs or from embryonic stem cells.

Polynucleotides-of-interest that could be expressed in this way include, but are not limited to: adenosine deaminase, the enzymes affected in lysosomal storage diseases, apolipoprotein E, brain derived neurotropihic factor (BDNF), bone morphogenetic protein 2 (BMP-2), bone morphogenetic protein 6 (BMP-6), bone morphogenetic protein 7 (BMP-7), cardiotrophin 1 (CT-1), CD22, CD40, ciliary neurotrophic factor (CNTF), CCL1-CCL28, CXCL1-CXCL17, CXCL1, CXCL2, CX3CL1, vascular endothelial cell growth factor (VEGF), dopamine, erythropoietin, Factor IX, Factor VIII, epidermal growth factor (EGF), estrogen, FAS-ligand, fibroblast growth factor 1 (FGF-1), fibroblast growth factor 2 (FGF-2), fibroblast growth factor 4 (FGF-4), fibroblast growth factor 5 (FGF-5), fibroblast growth factor 6 (FGF-6), fibroblast growth factor 1 (FGF-7), fibroblast growth factor 1 (FGF-10), Flt-3, granulocyte colony-stimulating factor (G-CSF), granulocyte macrophage stimulating factor (GM-CSF), growth hormone, hepatocyte growth factor (HGF), interferon alpha (IFN-a), interferon beta (IFN-b), interferon gamma (IFNg), insulin, glucagon, insulin-like growth factor 1(IGF-1), insulin-like growth factor 2 (IGF-2), interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), interleukin 13 (IL-13), interleukin 15 (IL-15), interleukin 17 (IL-17), interleukin 19 (IL-19), macrophage colony-stimulating factor (M-CSF), monocyte chemotactic protein 1 (MCP-1), macrophage inflammatory protein 3a (MIP-3a), macrophage inflammatory protein 3b (MIP-3b), nerve growth factor (NGF), neurotrophin 3 (NT-3), neurotrophin 4 (NT-4), parathyroid hormone, platelet derived growth factor AA (PDGF-AA), platelet derived growth factor AB (PDGF-AB), platelet derived growth factor BB (PDGF-BB), platelet derived growth factor CC (PDGF-CC), platelet derived growth factor DD (PDGF-DD), RANTES, stem cell factor (SCF), stromal cell derived factor 1 (SDF-1), testosterone, transforming growth factor alpha (TGF-a), transforming growth factor beta (TGF-b), tumor necrosis factor alpha (TNF-a), Wnt1, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, or Wnt16, Sonic hedgehog, Desert hedgehog, and Indian hedgehog.

In various embodiments, vectors of the invention comprise an expression control sequence operably linked to a polynucleotide encoding a truncated erythropoietin receptor.

In particular preferred embodiments, a vector of the invention comprises a tEpoR having a C-terminal truncation that reduces the turnover of the tEpoR compared to an endogenous erythropoietin receptor (EpoR), increases the half-life of the tEpoR compared to an endogenous erythropoietin receptor (EpoR), and/or increases the duration of mitogen activated signaling pathways, e.g., MAPK, JAK/STAT, PI3K, AKT, RAS. Thus, upon binding an EpoR agonist the tEpoR leads to activation of mitogenic pathways to increase cell proliferation or expansion of cells compared to EpoR expressing cells or cells not expressing any EpoR. Without wishing to be bound to any particular theory, it is believed that binding of an EpoR agonist, e.g., erythropoietin (EPO), to an EpoR induces dimerization of two receptor subunits and subsequent activation of the associated Janus kinase (Jak)2 (Witthuhn et al., 1993). This leads to phosphorylation of several tyrosine residues in EpoR and recruitment of SH2-containing proteins, which result in activation of several cascades of signal transduction pathways, notably the Ras/extracellular signal-regulated kinase (Erk)/mitogen-activated protein kinase (MAPK) (Torti et al., 1992) pathway and the phosphatidylinositol 3 kinase/Akt kinase pathway (Damen et al., 1995). Jak2 also phosphorylates signal transducer and activator of transcription (Stat)5 and Stat3 (Kirito et al., 1997), which then translocate to the nucleus to act as transcription factors and mediate EpoR mitogenic effects.

Without wishing to be bound to any particular theory, the present invention contemplates that expression of a truncated erythropoietin receptor in a cell offers a proliferative advantage over a cell expressing full-length erythropoietin receptors or expressing no erythropoietin receptors at all. tEpoR polypeptides are transported to the cell surface more efficiently than the full-length EpoR. Moreover, the tEpoR polypeptides of the invention lack one or more conserved tyrosine (Tyr) phosphorylation sites and/or protein binding sites in the C-terminus. One consequence of a tEpoR is that the tEpoR is still able to activate mitogenic pathways but is unable to efficiently recruit phosphatases that normally rapidly dephosphorylate and down-regulate the expression of EpoR. The result is increased intracellular signaling through the tEpoR compared to the normal EpoR, and increased activation of mitogen activated pathways that increase cell proliferation or expansion.

The amino acid sequences of representative full-length EpoRs are set forth in SEQ ID NOs: 19, 22, 25, 28, 31, and 34. Truncated EpoRs can be made using recombinant techniques known in the art. Particular truncated EpoR are made by inserting a stop codon at or near a C-terminal Tyr residue; thus, removing or mutating the Tyr residue in the process of creating a truncated EpoR.

Illustrative human tEpoR receptors comprise one or more mutations introducing a stop codon at or near, within 1, 2, 3, 4, 5, 6, 7, 8, 9, 10, 11, 12, 13, 14, 15, 16, 17, 18, 19, or 20 amino acids of a C-terminal Tyr residue. Exemplary C-terminal Tyr residues include, Tyr (Y) 344, 402, 430, 432, 444, 461, 465 and 480, as set forth in SEQ ID NO: 22 (note that SEQ ID NO: 22 lacks the first 24 amino acids that constitute the hydrophobic leader sequence of the full-length human EpoR set forth in SEQ ID NO: 19).

Illustrative murine tEpoR receptors comprise one or more mutations introducing a stop codon at or near, within 1, 2, 3, 4, 5, 6, 7, 8, 9, 10, 11, 12, 13, 14, 15, 16, 17, 18, 19, or 20 amino acids of a C-terminal Tyr residue. Exemplary C-terminal Tyr residues include, Tyr (Y) 343, 401, 429, 431, 442, 460, 464 and 479, as set forth in SEQ ID NO: 28 (note that SEQ ID NO: 28 lacks the first 24 amino acids that constitute the hydrophobic leader sequence of the full-length murine EpoR set forth in SEQ ID NO: 25).

Illustrative rat tEpoR receptors comprise one or more mutations introducing a stop codon at or near, within 1, 2, 3, 4, 5, 6, 7, 8, 9, 10, 11, 12, 13, 14, 15, 16, 17, 18, 19, or 20 amino acids of a C-terminal Tyr residue. Exemplary C-terminal Tyr residues include, Tyr (Y) 343, 401, 429, 431, 442, 460, 464 and 479, as set forth in SEQ ID NO: 34 (note that SEQ ID NO: 34 lacks the first 24 amino acids that constitute the hydrophobic leader sequence of the full-length rat EpoR set forth in SEQ ID NO: 31).

Particular examples of biologically active truncated EpoRs include, but are not limited to, C-terminally truncated EpoRs comprising or consisting of amino acids 1 to 335, 1 to 336, 1 to 337, 1 to 338, 1 to 339, 1 to 340, 1 to 341, 1 to 342, 1 to 343, 1 to 344, 1 to 345, 1 to 346, 1 to 347, 1 to 348, 1 to 349, 1 to 350, 1 to 351, 1 to 352, 1 to 353, 1 to 354, 1 to 355, 1 to 356, 1 to 357, 1 to 358, 1 to 359, 1 to 360, 1 to 361, 1 to 362, 1 to 363, 1 to 364, 1 to 365, 1 to 366, 1 to 367, 1 to 368, 1 to 369, 1 to 370, 1 to 371, 1 to 372, 1 to 373, 1 to 374, 1 to 375, 1 to 376, 1 to 377, 1 to 378, 1 to 379, 1 to 380, 1 to 381, 1 to 382, 1 to 383, 1 to 384, 1 to 385, 1 to 386, 1 to 387, 1 to 388, 1 to 389, 1 to 390, 1 to 391, 1 to 392, 1 to 393, 1 to 394, 1 to 395, 1 to 396, 1 to 397, 1 to 398, 1 to 399, 1 to 400, 1 to 401, 1 to 402, 1 to 403, 1 to 404, 1 to 405, 1 to 406, 1 to 407, 1 to 408, 1 to 409, 1 to 410, 1 to 411, 1 to 412, 1 to 413, 1 to 414, 1 to 415, 1 to 416, 1 to 417, 1 to 418, 1 to 419, 1 to 420, 1 to 421, 1 to 422, 1 to 423, 1 to 424, 1 to 425, 1 to 526, 1 to 427, 1 to 428, 1 to 429, 1 to 430, 1 to 431, 1 to 432, 1 to 433, 1 to 434, 1 to 435, 1 to 436, 1 to 437, 1 to 438, 1 to 439, 1 to 440, 1 to 441, 1 to 442, 1 to 443, 1 to 444, 1 to 445, 1 to 446, 1 to 447, 1 to 448, 1 to 449, 1 to 450, 1 to 451, 1 to 452, 1 to 453, 1 to 454, 1 to 455, 1 to 456, 1 to 457, 1 to 458, 1 to 459, 1 to 460, 1 to 461, 1 to 462, 1 to 463, 1 to 464, 1 to 465, 1 to 466, 1 to 467, 1 to 468, 1 to 469, 1 to 470, 1 to 471, 1 to 472, 1 to 473, 1 to 474, 1 to 475, 1 to 476, 1 to 477, 1 to 478, 1 to 479, 1 to 480, 1 to 481, 1 to 482, 1 to 483, 1 to 484, 1 to 485, 1 to 486, 1 to 487, 1 to 488, 1 to 489, 1 to 490, 1 to 491, 1 to 492, 1 to 493, 1 to 494, 1 to 495, 1 to 496, 1 to 497, 1 to 498, 1 to 499, or 1 to 500 of the amino acid sequence set forth in SEQ ID NO: 19, 22, 25, 28, 31, and 34, and variants thereof. In certain embodiments, a tEpoR polypeptide of the invention comprises the minimal active fragment of a full-length EpoR polypeptide capable of cell proliferation or cell expansion, in vitro, ex vivo, or in vivo.

Specific examples of tEpoR polypeptide variants include tEpoR polypeptides, having one or more amino acid additions, deletions, or substitutions, e.g., at C-terminal Tyr residue selected from the groups consisting of: Tyr (Y) 344, 402, 430,432, 444, 461, 465 and 480, as set forth in SEQ ID NO: 22 and Tyr (Y) 343, 401, 429, 431, 442, 460, 464 and 479, as set forth in SEQ ID NOs: 28 or 34.

In a preferred embodiment, vectors of the invention comprise a tEpoR comprising a C-terminal truncation of about 50 to about 60 amino acids, about 80 to about 90 amino acids, or about 85 to about 95 amino acids, or about 55, about 83, or about 91 amino acids.

In one embodiment, a vector of the invention comprises at least one modified or unmodified retroviral LTR, e.g., lentiviral LTR, a β-globin promoter and a β-globin locus control region (LCR) operably linked to a gene of interest, an expression control sequence operably linked to a truncated erythropoietin receptor (tEpoR). Suitable modifications of the LTRs include, but are not limited to: replacement of the 5' LTR is with a heterologous promoter, e.g., cytomegalovirus (CMV) promoter, a Rous Sarcoma Virus (RSV) promoter, a thymidine kinase promoter, or an Simian Virus 40 (SV40) promoter; and one or more modifications, additions, and/or deletions of a 3' LTR as discussed elsewhere herein.

In a particular embodiment, erythroid expression of a polynucleotide is achieved using a human β-globin promoter, a β-globin LCR that comprises one or more of DNAase I hypersensitive sites 2, 3 and 4 from the human β-globin LCR, and/or a human β-globin 3' enhancer element.

In various embodiments, a vector of the invention comprises one or more elements selected from the group consisting of: a Psi packaging sequence (Ψ+), a central polypurine tract/DNA flap (cPPT/FLAP), a retroviral export element, a posttranscriptional regulatory element, an insulator element, a polyadenylation sequence, a selectable marker, and a cell suicide gene, as discussed elsewhere herein.

In one embodiment, a vector comprises a left (5') retroviral LTR, a Psi packaging sequence (Ψ+), central polypurine tract/DNA flap (cPPT/FLAP), a retroviral export element, a β-globin promoter, a β-globin locus control region (LCR), and optionally a 3' β-globin enhancer operably linked to a polynucleotide of interest, an erythroid cell specific expression control sequence operably linked to a truncated erythropoietin receptor (tEpoR), and a right (3') retroviral LTR that comprises one or more insulator elements, or a polyadenylation sequence.

In particular embodiment, a vector of the invention is a lentiviral vector that comprises a left (5') HIV-1 LTR, a Psi packaging sequence (Ψ+), an HIV-1 central polypurine tract/DNA flap (cPPT/FLAP), a rev response element (RRE), a β-globin promoter, a β-globin locus control region (LCR), and optionally a 3' β-globin enhancer operably linked to a polynucleotide of interest, an erythroid cell specific expression control sequence operably linked to a truncated erythropoietin receptor (tEpoR), and a right (3') retroviral LTR that comprises one or more insulator elements, and a rabbit β-globin polyA sequence (rβgpA).

The skilled artisan would appreciate that many other different embodiments can be fashioned from the existing embodiments of the invention, such that the therapeutic transgene or gene of interest is expressed in a target cell type or cell lineage and that the tEpoR is expressed in the same and/or a different target cell type or cell lineage to be expanded.

D. Compositions and Formulations

The present invention further includes pharmaceutical compositions comprising transduced cells produced according to methods described herein and a pharmaceutically acceptable carrier. As used herein "pharmaceutically acceptable carrier" includes any and all solvents, dispersion media, coatings, antibacterial and antifungal agents, isotonic and absorption delaying agents, and the like that are physiologically compatible, including pharmaceutically acceptable cell culture media. In one embodiment, a composition comprising a carrier is suitable for parenteral administration, e.g., intravascular (intravenous or intraarterial), intraperitoneal or intramuscular administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the transduced cells, use thereof in the pharmaceutical compositions of the invention is contemplated.

The compositions of the invention may comprise one or more polypeptides, polynucleotides, vectors comprising same, transduced cells, etc., as described herein, formulated in pharmaceutically-acceptable or physiologically-acceptable solutions for administration to a cell or an animal, either alone, or in combination with one or more other modalities of therapy. It will also be understood that, if desired, the compositions of the invention may be administered in combination with other agents as well, such as, e.g., cytokines, growth factors, hormones, small molecules or various pharmaceutically-active agents. There is virtually no limit to other components that may also be included in the compositions, provided that the additional agents do not adversely affect the ability of the composition to deliver the intended gene therapy.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

In certain circumstances it will be desirable to deliver the compositions disclosed herein parenterally, intravenously, intramuscularly, or even intraperitoneally as described, for example, in U.S. Pat. Nos. 5,543,158; 5,641,515 and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., Remington: The Science and Practice of Pharmacy, 20th Edition. Baltimore, Md.: Lippincott Williams & Wilkins, 2000). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the compositions may be delivered by intranasal sprays, inhalation, and/or other aerosol delivery vehicles. Methods for delivering genes, polynucleotides, and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, optionally mixing with CPP polypeptides, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques. The formulations and compositions of the invention may comprise one or more repressors and/or activators comprised of a combination of any number of polypeptides, polynucleotides, and small molecules, as described herein, formulated in pharmaceutically-acceptable or physiologically-acceptable solutions (e.g., culture medium) for administration to a cell or an animal, either alone, or in combination with one or more other modalities of therapy. It will also be understood that, if desired, the compositions of the invention may be administered in combination with other agents as well, such as, e.g., cells, other proteins or polypeptides or various pharmaceutically-active agents.

In a particular embodiment, a formulation or composition according to the present invention comprises a cell contacted with a combination of any number of polypeptides, polynucleotides, and small molecules, as described herein.

In certain aspects, the present invention provides formulations or compositions suitable for the delivery of viral vector systems (i.e., viral-mediated transduction) including, but not limited to, retroviral (e.g., lentiviral) vectors.

Exemplary formulations for ex vivo delivery may also include the use of various transfection agents known in the art, such as calcium phosphate, electoporation, heat shock and various liposome formulations (i.e., lipid-mediated transfection). Liposomes, as described in greater detail below, are lipid bilayers entrapping a fraction of aqueous fluid. DNA spontaneously associates to the external surface of cationic liposomes (by virtue of its charge) and these liposomes will interact with the cell membrane.

In certain aspects, the present invention provides pharmaceutically acceptable compositions which comprise a therapeutically-effective amount of one or more polynucleotides or polypeptides, as described herein, formulated together with one or more pharmaceutically acceptable carriers (additives) and/or diluents (e.g., pharmaceutically acceptable cell culture medium).

Particular embodiments of the invention may comprise other formulations, such as those that are well known in the pharmaceutical art, and are described, for example, in Remington: The Science and Practice of Pharmacy, 20th Edition. Baltimore, Md.: Lippincott Williams & Wilkins, 2000.

E. Gene Therapy Methods

The retroviral vectors provide improved methods of gene therapy. As used herein, the term "gene therapy" refers to the introduction of a polynucleotide into a cell's genome that restores, corrects, or modifies the gene and/or expression of the gene. In various embodiments, a viral vector of the invention comprises a hematopoietic expression control sequence that expresses a therapeutic transgene encoding a polypeptide that provides curative, preventative, or ameliorative benefits to a subject diagnosed with or that is suspected of having monogenic disease, disorder, or condition or a disease, disorder, or condition of the hematopoietic system. In addition, vectors of the invention comprise another expression control sequence that expresses a truncated erythropoietin receptor in a cell, in order to increase or expand a specific population or lineage of cells, e.g., erythroid cells. The virus can infect and transduce the cell in vivo, ex vivo, or in vitro. In ex vivo and in vitro embodiments, the transduced cells can then be administered to a subject in need of therapy. The present invention contemplates that the vector systems, viral particles, and transduced cells of the invention are be used to treat, prevent, and/or ameliorate a monogenic disease, disorder, or condition or a disease, disorder, or condition of the hematopoietic system in a subject, e.g., a hemoglobinopathy.

As used herein, "hematopoiesis," refers to the formation and development of blood cells from progenitor cells as well as formation of progenitor cells from stem cells. Blood cells include but are not limited to erythrocytes or red blood cells (RBCs), reticulocytes, monocytes, neutrophils, megakaryocytes, eosinophils, basophils, B-cells, macrophages, granulocytes, mast cells, thrombocytes, and leukocytes.

As used herein, the term "hemoglobinopathy" or "hemoglobinopathic condition" includes any disorder involving the presence of an abnormal hemoglobin molecule in the blood. Examples of hemoglobinopathies included, but are not limited to, hemoglobin C disease, hemoglobin sickle cell disease (SCD), sickle cell anemia, and thalassemias. Also included are hemoglobinopathies in which a combination of abnormal hemoglobins are present in the blood (e.g., sickle cell/Hb-C disease).

The term "sickle cell anemia" or "sickle cell disease" is defined herein to include any symptomatic anemic condition which results from sickling of red blood cells. Manifestations of sickle cell disease include: anemia; pain; and/or organ dysfunction, such as renal failure, retinopathy, acute-chest syndrome, ischemia, priapism and stroke. As used herein the term "sickle cell disease" refers to a variety of clinical problems attendant upon sickle cell anemia, especially in those subjects who are homozygotes for the sickle cell substitution in HbS. Among the constitutional manifestations referred to herein by use of the term of sickle cell disease are delay of growth and development, an increased tendency to develop serious infections, particularly due to pneumococcus, marked impairment of splenic function, preventing effective clearance of circulating bacteria, with recurrent infarcts and eventual destruction of splenic tissue. Also included in the term "sickle cell disease" are acute episodes of musculoskeletal pain, which affect primarily the lumbar spine, abdomen, and femoral shaft, and which are similar in mechanism and in severity to the bends. In adults, such attacks commonly manifest as mild or moderate bouts of short duration every few weeks or months interspersed with agonizing attacks lasting 5 to 7 days that strike on average about once a year. Among events known to trigger such crises are acidosis, hypoxia and dehydration, all of which potentiate intracellular polymerization of HbS (J. H. Jandl, Blood: Textbook of Hematology, 2nd Ed., Little, Brown and Company, Boston, 1996, pages 544-545). As used herein, the term "thalassemia" encompasses hereditary anemias that occur due to mutations affecting the synthesis of hemoglobin. Thus, the term includes any symptomatic anemia resulting from thalassemic conditions such as severe or β thalassemia, thalassemia major, thalassemia intermedia, α thalassemias such as hemoglobin H disease.

As used herein, "thalassemia" refers to a hereditary disorder characterized by defective production of hemoglobin. Examples of thalassemias include α and β thalassemia. β thalassemias are caused by a mutation in the beta globin chain, and can occur in a major or minor form. In the major form of β thalassemia, children are normal at birth, but develop anemia during the first year of life. The mild form of β thalassemia produces small red blood cells a thalassemias are caused by deletion of a gene or genes from the globin chain.

α thalassemia typically results from deletions involving the HBA1 and HBA2 genes. Both of these genes encode α-globin, which is a component (subunit) of hemoglobin. There are two copies of the HBA1 gene and two copies of the HBA2 gene in each cellular genome. As a result, there are four alleles that produce α-globin. The different types of α thalassemia result from the loss of some or all of these alleles. Hb Bart syndrome, the most severe form of α thalassemia, results from the loss of all four α-globin alleles. HbH disease is caused by a loss of three of the four α-globin alleles. In these two conditions, a shortage of α-globin prevents cells from making normal hemoglobin. Instead, cells produce abnormal forms of hemoglobin called hemoglobin Bart (Hb Bart) or hemoglobin H (HbH). These abnormal hemoglobin molecules cannot effectively carry oxygen to the body's tissues. The substitution of Hb Bart or HbH for normal hemoglobin causes anemia and the other serious health problems associated with a thalassemia.

In a preferred embodiment, gene therapy methods of the invention are used to treat, prevent, or ameliorate a hemoglobinopathy is selected from the group consisting of: hemoglobin C disease, hemoglobin sickle cell disease (SCD), sickle cell anemia, hereditary anemia, thalassemia, β-thalassemia, thalassemia major, thalassemia intermedia, α-thalassemia, and hemoglobin H disease.

In various embodiments, the retroviral vectors are administered by direct injection to a cell, tissue, or organ of a subject in need of gene therapy, in vivo. In various other embodiments, cells are transduced in vitro or ex vivo with vectors of the invention, and optionally expanded ex vivo. The transduced cells are then administered to a subject in need of gene therapy.

Cells suitable for transduction and administration in the gene therapy methods of the invention include, but are not limited to stem cells, progenitor cells, and differentiated cells. In certain embodiments, the transduced cells are embryonic stem cells, bone marrow stem cells, umbilical cord stem cells, placental stem cells, mesenchymal stem cells, neural stem cells, liver stem cells, pancreatic stem cells, cardiac stem cells, kidney stem cells, hematopoietic stem cells.

In various embodiments, the use of stem cells is preferred because they have the ability to differentiate into the appropriate cell types when administered to a particular biological niche, in vivo. The term "stem cell" refers to a cell which is an undifferentiated cell capable of (1) long term self-renewal, or the ability to generate at least one identical copy of the original cell, (2) differentiation at the single cell level into multiple, and in some instance only one, specialized cell type and (3) of in vivo functional regeneration of tissues. Stem cells are subclassified according to their developmental potential as totipotent, pluripotent, multipotent and oligo/unipotent. "Self-renewal" refers a cell with a unique capacity to produce unaltered daughter cells and to generate specialized cell types (potency). Self-renewal can be achieved in two ways. Asymmetric cell division produces one daughter cell that is identical to the parental cell and one daughter cell that is different from the parental cell and is a progenitor or differentiated cell. Asymmetric cell division does not increase the number of cells. Symmetric cell division produces two identical daughter cells. "Proliferation" or "expansion" of cells refers to symmetrically dividing cells.

As used herein, the term "pluripotent" means the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. As used herein, the term "multipotent" refers to the ability of an adult stem cell to form multiple cell types of one lineage. For example, hematopoietic stem cells are capable of forming all cells of the blood cell lineage, e.g., lymphoid and myeloid cells.

As used herein, the term "progenitor" or "progenitor cells" refers to cells that have the capacity to self-renew and to differentiate into more mature cells. Progenitor cells have a reduced potency compared to pluripotent and multipotent stem cells. Many progenitor cells differentiate along a single lineage, but may also have quite extensive proliferative capacity.

Hematopoietic stem cells (HSCs) give rise to committed hematopoietic progenitor cells (HPCs) that are capable of generating the entire repertoire of mature blood cells over the lifetime of an organism. The term "hematopoietic stem cell" or "HSC" refers to multipotent stem cells that give rise to the all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See Fei, R., et al., U.S. Pat. No. 5,635,387; McGlave, et al., U.S. Pat. No. 5,460,964; Simmons, P., et al., U.S. Pat. No. 5,677,136; Tsukamoto, et al., U.S. Pat. No. 5,750,397; Schwartz, et al., U.S. Pat. No. 5,759,793; DiGuisto, et al., U.S. Pat. No. 5,681,599; Tsukamoto, et al., U.S. Pat. No. 5,716,827). When transplanted into lethally irradiated animals or humans, hematopoietic stem and progenitor cells can repopulate the erythroid, neutrophil-macrophage, megakaryocyte and lymphoid hematopoietic cell pool.

In preferred embodiments, the transduced cells are hematopoietic stem and/or progenitor cells isolated from bone marrow, umbilical cord blood, or peripheral circulation. In particular preferred embodiments, the transduced cells are hematopoietic stem cells isolated from bone marrow, umbilical cord blood, or peripheral circulation.

HSCs may be identified according to certain phenotypic or genotypic markers. For example, HSCs may be identified by their small size, lack of lineage (lin) markers, low staining (side population) with vital dyes such as rhodamine 123 (rhodamineDULL, also called rholo) or Hoechst 33342, and presence of various antigenic markers on their surface, many of which belong to the cluster of differentiation series (e.g., CD34, CD38, CD90, CD133, CD105, CD45, Ter119, and c-kit, the receptor for stem cell factor). HSCs are mainly negative for the markers that are typically used to detect lineage commitment, and, thus, are often referred to as Lin(−) cells.

In one embodiment, human HSCs may be characterized as CD34+, CD59+, Thy1/CD90+, CD38$^{lo/-}$, C-kit/CD117+, and Lin(−). However, not all stem cells are covered by these combinations, as certain HSCs are CD34−/CD38−. Also some studies suggest that earliest stem cells may lack c-kit on the cell surface. For human HSCs, CD133 may represent an early marker, as both CD34+ and CD34− HSCs have been shown to be CD133$^+$. It is known in the art that CD34$^+$ and Lin(−) cells also include hematopoietic progenitor cells.

In another embodiment, the hematopoietic hierarchy is determined by a SLAM code. The SLAM (Signaling lymphocyte activation molecule) family is a group of >10 molecules whose genes are located mostly tandemly in a single locus on chromosome 1 (mouse), all belonging to a subset of immunoglobulin gene superfamily, and originally thought to be involved in T-cell stimulation. This family includes CD48, CD150, CD244, etc., CD150 being the founding member, and, thus, also called slamF1, i.e., SLAM family member 1. The signature SLAM code for the hematopoietic hierarchy is hematopoietic stem cells (HSC)—CD150$^+$CD48$^-$CD244$^-$; multipotent progenitor cells (MPPs)—CD150$^-$CD48$^-$CD244$^+$; lineage-restricted progenitor cells (LRPs)—CD150$^-$CD48$^+$CD244$^+$; common myeloid progenitor (CMP)—lin$^-$SCA-1$^-$c-kit$^+$CD34$^+$CD16/32$^{mid}$; granulocyte-macrophage progenitor (GMP)—lin$^-$SCA-1$^-$c-kit$^+$CD34$^+$CD16/32$^{hi}$; and megakaryocyte-erythroid progenitor (MEP)—lin$^-$SCA-1$^-$c-kit$^+$CD34$^-$CD16/32$^{low}$.

In mice, Irving Weissman's group at Stanford University was the first to isolate mouse hematopoietic stem cells in 1988 and was also the first to work out the markers to distinguish the mouse hematopoietic hierarchy. The markers for the hematopoietic hierarchy is long-term hematopoietic stem cells (LT-HSC)—CD34$^-$, SCA-1$^+$, Thy1.1$^{+/lo}$, C-kit$^+$, lin$^-$, CD135$^-$, Slamf1/CD150$^+$; short-term hematopoietic stem cells (ST-HSC)—CD34$^+$, SCA-1$^+$, Thy1.1$^{+/lo}$, C-kit$^+$, lin$^-$, CD135$^-$, Slamf1/CD150$^+$, Mac-1 (CD11b)$^{lo}$; early multipotent progenitors—(Early MPP)—CD34$^+$, SCA-1$^+$, Thy1.1$^-$, C-kit$^+$, lin$^-$, CD135$^+$, Slamf1/CD150$^-$, Mac-1 (CD11b)$^{lo}$, CD4$^{lo}$; and late multipotent progenitors (Late MPP)—CD34$^+$, SCA-1$^+$, Thy1.1$^-$, C-kit$^+$, lin$^-$, CD135$^{high}$, Slamf1/CD150$^-$, Mac-1 (CD11b)$^{lo}$, CD4$^{lo}$.

In one embodiment, the hematopoietic cells are CD105$^+$ Sca1$^+$ cells.

Cells of the invention can be autologous/autogeneic ("self") or non-autologous ("non-self," e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells of the invention are allogeneic.

A "subject," as used herein, includes any animal that exhibits a symptom of a monogenic disease, disorder, or condition that can be treated with the gene therapy vectors, cell-based therapeutics, and methods disclosed elsewhere herein. In preferred embodiments, a subject includes any animal that exhibits symptoms of a disease, disorder, or condition of the hematopoietic system, e.g., a hemoglobinopathy, that can be treated with the gene therapy vectors, cell-based therapeutics, and methods disclosed elsewhere herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include animals that exhibit aberrant amounts (lower or higher amounts than a "normal" or "healthy" subject) of one or more physiological activities that can be modulated by gene therapy.

As used herein "treatment" or "treating," includes any beneficial or desirable effect on the symptoms or pathology of a disease or pathological condition, and may include even minimal reductions in one or more measurable markers of the disease or condition being treated. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, the term "amount" refers to "an amount effective" or "an effective amount" of a virus or transduced therapeutic cell to achieve a beneficial or desired prophylactic or therapeutic result, including clinical results.

A "prophylactically effective amount" refers to an amount of a virus or transduced therapeutic cell effective to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of a virus or transduced therapeutic cell may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject (e.g., a patient).

In one embodiment, the present invention provides a method of providing a transduced cell to a subject that comprises administering, e.g., parenterally, one or more cells transduced with a vector comprising a cell type or cell lineage specific promoter, enhancer, or promoter/enhancer operably linked to a gene of interest and an ubiquitous promoter, enhancer, or promoter/enhancer or cell type or cell lineage specific promoter, enhancer, or promoter/enhancer operably linked to a tEpoR, or another suitable vector of the invention as discussed elsewhere herein.

In a particular embodiment, a method of treating a hemoglobinopathy in a subject is provided. The method comprises administering a population of cells comprising hematopoietic stem or progenitor cells transduced with a vector comprising a hematopoietic cell specific promoter, enhancer, or promoter/enhancer operably linked to a gene of interest and an ubiquitous promoter, enhancer, or promoter/enhancer or cell type or cell lineage specific promoter, enhancer, or promoter/enhancer operably linked to a tEpoR, or another suitable vector of the invention as discussed elsewhere herein.

In one embodiment, the present invention provides a method of selectively expanding the number erythroid cells in a subject comprising administering a population of cells comprising hematopoietic stem or progenitor cells transduced with a vector comprising a hematopoietic cell specific promoter, enhancer, or promoter/enhancer operably linked to a gene of interest and an ubiquitous promoter, enhancer, or promoter/enhancer or cell type or cell lineage specific promoter, enhancer, or promoter/enhancer operably linked to a tEpoR, or another suitable vector of the invention as discussed elsewhere herein, wherein the number of erythroid progeny cells of the hematopoietic stem cells are expanded in the subject.

In another embodiment, the present invention provides a method of increasing the proportion of red blood cells or erythrocytes compared to white blood cells or leukocytes in a subject. The method comprises administering a population of cells comprising hematopoietic stem or progenitor cells transduced with a vector comprising a hematopoietic cell promoter, enhancer, or promoter/enhancer operably linked to a gene of interest and an ubiquitous promoter, enhancer, or promoter/enhancer or cell type or cell lineage specific promoter, enhancer, or promoter/enhancer operably linked to a tEpoR, or another suitable vector of the invention as discussed elsewhere herein, wherein the proportion of red blood cell progeny cells of the hematopoietic stem cells are increased compared to white blood cell progeny cells of the hematopoietic stem cells in the subject.

In particular embodiments, the subject is not administered EPO, and the efficacy of cell expansion mediated by the truncated EpoR is due to endogenous EPO production in the subject. Without wishing to be bound to any particular theory the present invention contemplates, in part, that particular subjects that suffer from hemoglobinopathies, such as thalassemias, for example, have constitutively high levels of plasma EPO compared to normal subjects, e.g., about 15 fold, about 20 fold, about 30 fold, about 40 fold, or about 50 fold or more. Thus, sufficiently high levels of EPO to increase or expand the number of cells expressing a tEpoR about 5 fold, about 10 fold, about 25 fold, about 50 fold, about 75 fold, about 100 fold, about 150 fold, about 200 fold or about 250 fold or more compared to cells not expressing the tEpoR and/or expressing an endogenous EpoR. In another embodiment, sufficiently high levels of EPO to increase or expand the number of cells expressing a tEpoR at least 5 fold, at least 10 fold, at least 25 fold, at least 50 fold, at least 75 fold, at least 100 fold, at least 150 fold, at least 200 fold or at least 250 fold or more compared to cells not expressing the tEpoR and/or expressing an endogenous EpoR.

In certain embodiments, the subject is also administered an EpoR agonist, e.g., EPO, in advance, concurrently with, and/or following administration of the transduced cells. As used herein, the term "erythropoietin" or "EPO" refers to a glycoprotein produced in the kidney, which is the principal hormone responsible for stimulating red blood cell production (erythrogenesis). EPO stimulates the division and differentiation of committed erythroid progenitors in the bone marrow. Normal plasma erythropoietin levels range from 0.01 to 0.03 Units/mL, and can increase up to 100 to 1,000-fold during hypoxia or anemia. Graber and Krantz, *Ann. Rev. Med.* 29:51 (1978); Eschbach and Adamson, *Kidney Intl.* 28:1 (1985). Recombinant human erythropoietin (rHuEpo or epoietin alpha) is commercially available as EPOGEN® (epoietin alpha, recombinant human erythropoietin) (Amgen Inc., Thousand Oaks, Calif.) and as PROCRIT® (epoietin alpha, recombinant human erythropoietin) (Ortho Biotech Inc., Raritan, N.J.).

In a preferred embodiment, the subject is administered EPO.

In illustrative embodiments, following administration of the transduced cells to the subject, the subject is administered EPO every 1, 2, 3, 4, 5, 6, or 7 days, every week, every other week, every month, every other month, every 1, 2, 3, 4, 5, or 6 months, or once a year, or any intervening frequency of time, for the duration of treatment. In particular illustrative embodiments, the dose of EPO administered to the subject is about 100 to about 50000 units (IU; international units)/week, about 200 to about 40000 IU/week, about 500 to about 30000 IU/week, about 1000 to about 40000 IU/week, about 1000 to about 30000 IU/week, about 1000 to about 20000 IU/week, about 5000 to about 40000 IU/week, about 5000 to about 30000 IU/week, about 5000 to about 20000 IU/week, about 10000 to about 40000 IU/week, about 10000 to about 30000 IU/week, about 10000 to about 20000 IU/week, or any intervening ranges of IU/week, without limitation.

In particular illustrative embodiments, the dose of EPO administered to the subject is at least about 100 units/week, at least about 200 units/week, at least about 500 units/week, at least about 1000 units/week, at least about 5000 units/week, at least about 10000 units/week, at least about 20000 units/week, at least about 30000 units/week, at least about 40000 units/week, at least about 50000 units/week, or any intervening ranges of IU/week, without limitation.

In particular illustrative embodiments, the dose of EPO administered to the subject is about 1 to about 500 IU/kg of body weight/week, about 10 to about 500 IU/kg of body weight/week, about 25 to about 500 IU/kg of body weight/week, about 50 to about 500 IU/kg of body weight/week, about 100 to about 500 IU/kg of body weight/week, about 100 to about 250 IU/kg of body weight/week, about 250 to about 500 IU/kg of body weight/week, or any intervening ranges of IU/kg of body weight/week, without limitation.

In particular illustrative embodiments, the dose of EPO administered to the subject is at least about 1 IU/kg of body weight/week, at least about 10 IU/kg of body weight/week, at least about 25 IU/kg of body weight/week, at least about 50 IU/kg of body weight/week, at least about 75 IU/kg of body weight/week, at least about 100 IU/kg of body weight/week, at least about 200 IU/kg of body weight/week, at least about 250 IU/kg of body weight/week, at least about 300 IU/kg of body weight/week, at least about 350 IU/kg of body weight/week, at least about 400 IU/kg of body weight/week, at least about 500 IU/kg of body weight/week, or any intervening ranges of IU/kg of body weight/week, without limitation.

In various method provided by the invention, expression of the tEpoR in the presence of EPO or another EpoR agonist increases or expands the population of cells expressing the tEpoR compared to cells that do not express the tEpoR and/or express the normal EpoR. As noted elsewhere herein, an expression control sequence that expresses the tEpoR receptor in all cells (ubiquitous or conditional expression), or in a particular cell type or cell lineage will lead to expansion of the tEpoR expressing cells compared to cells that do not express the tEpoR and/or express the normal EpoR.

Illustrative cells expanded using the vectors and methods of the present invention include, but are not limited to: embryonic stem cells, bone marrow stem cells, umbilical cord stem cells, placental stem cells, mesenchymal stem cells, neural stem cells, liver stem cells, pancreatic stem cells, cardiac stem cells, kidney stem cells, hematopoietic stem cells, hematopoietic progenitor cells, myeloid progenitors, lymphoid progenitors, thrombopoietic progenitors, erythroid progenitors, granulopoietic progenitors, monocytopoietic progenitors, megakaryoblasts, promegakaryocytes, megakaryocytes, thrombocytes/platelets, proerythroblasts, basophilic erythroblasts, polychromatic erythroblasts, orthochromatic erythrocytes, polychromatic erythrocytes, erythrocytes (RBCs), basophilic promyelocytes, basophilic myelocytes, basophilic metamyelocytes, basophils, neutrophilic promyelocytes, neutrophilic myelocytes, neutrophilic metamyelocytes, neutrophils, eosinophilic promyelocytes, eosinophilic myelocytes, macrophages, dendritic cells, lymphoblasts, prolymphocytes, natural killer (NK)-cells, small lymphocytes, T-lymphocytes, B-lymphocytes, plasma cells, and lymphoid dendritic cells. In preferred embodiments, the target cell type is one or more erythroid cells, e.g., proerythroblast, basophilic erythroblast, polychromatic erythroblast, orthochromatic erythroblast, polychromatic erythrocyte, and erythrocyte (RBC).

In preferred embodiments, cells expanded using the vectors and methods of the present invention include, but are not limited to: hematopoietic stem or progenitor cells, proerythroblasts, basophilic erythroblasts, polychromatic erythroblasts, orthochromatic erythroblasts, polychromatic erythrocytes, and erythrocytes (RBCs), or any combination thereof.

In one embodiment, following EPO administration, the cells expressing a tEpoR are expanded about 5 fold, about 10 fold, about 25 fold, about 50 fold, about 75 fold, about 100 fold, about 150 fold, about 200 fold or about 250 fold or more compared to cells expressing the tEpoR in the subject before the administration of EPO or compared to cells not expressing the tEpoR and/or expressing an endogenous EpoR.

In another embodiment, following EPO administration, the cells expressing a tEpoR are expanded at least 5 fold, at least 10 fold, at least 25 fold, at least 50 fold, at least 75 fold, at least 100 fold, at least 150 fold, at least 200 fold or at least 250 fold or more compared to cells expressing the tEpoR in the subject before the administration of EPO or compared to cells not expressing the tEpoR and/or expressing an endogenous EpoR.

In a particular embodiment, following EPO administration, the erythroid cells expressing a tEpoR are expanded about 5 fold, about 10 fold, about 25 fold, about 50 fold, about 75 fold, about 100 fold, about 150 fold, about 200 fold or about 250 fold or more compared to erythroid cells expressing the tEpoR in the subject before the administration of EPO or compared to non-erythroid cells comprising the tEpoR vector but that does not express tEpoR.

In another embodiment, following EPO administration, the erythroid cells expressing a tEpoR are expanded at least 5 fold, at least 10 fold, at least 25 fold, at least 50 fold, at least 75 fold, at least 100 fold, at least 150 fold, at least 200 fold or at least 250 fold or more compared to erythroid cells expressing the tEpoR in the subject before the administration of EPO or compared to non-erythroid cells comprising the tEpoR vector but that does not express tEpoR.

Without wishing to be bound to any particular theory, an important advantage provided by the vectors, compositions, and methods of the present invention is the high efficacy of gene therapy that can be achieved by administering populations of cells comprising lower percentages of transduced cells compared to existing methods. This provides important safety advantages associated with reduced chances of deleterious mutation, transformation, or oncogene activation of cellular genes in transduced cells.

The transduced cells may be administered as part of a bone marrow or cord blood transplant in an individual that has or has not undergone bone marrow ablative therapy. In one embodiment, transduced cells of the invention are administered in a bone marrow transplant to an individual that has undergone chemoablative or radioablative bone marrow therapy.

In one embodiment, a dose of transduced cells is delivered to a subject intravenously. In preferred embodiments, transduced hematopoietic stem cells are intravenously administered to a subject.

In particular embodiments, patients receive a dose of transduced cells, e.g., hematopoietic stem cells, of about $1 \times 10^5$ cells/kg, about $5 \times 10^5$ cells/kg, about $1 \times 10^6$ cells/kg, about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, about $1 \times 10'$ cells/kg, about $5 \times 10'$ cells/kg, about $1 \times 10^8$ cells/kg, or more in one single intravenous dose. In certain embodiments, patients receive a dose of transduced cells, e.g., hematopoietic stem cells, of at least $1 \times 10^5$ cells/kg, at least $5 \times 10^5$ cells/kg, at least $1 \times 10^6$ cells/kg, at least $2 \times 10^6$ cells/kg, at least $3 \times 10^6$ cells/kg, at least $4 \times 10^6$ cells/kg, at least $5 \times 10^6$ cells/kg, at least $6 \times 10^6$ cells/kg, at least $7 \times 10^6$ cells/kg, at least $8 \times 10^6$ cells/kg, at least $9 \times 10^6$ cells/kg, at least $1 \times 10^7$ cells/kg, at least $5 \times 10^7$ cells/kg, at least $1 \times 10^8$ cells/kg, or more in one single intravenous dose.

In an additional embodiment, patients receive a dose of transduced cells, e.g., hematopoietic stem cells, of about $1 \times 10^5$ cells/kg to about $1 \times 10^8$ cells/kg, about $1 \times 10^6$ cells/kg to about $1 \times 10^8$ cells/kg, about $1 \times 10^6$ cells/kg to about $9 \times 10^6$ cells/kg, about $2 \times 10^6$ cells/kg to about $8 \times 10^6$ cells/kg, about $2 \times 10^6$ cells/kg to about $8 \times 10^6$ cells/kg, about $2 \times 10^6$ cells/kg to about $5 \times 10^6$ cells/kg, about $3 \times 10^6$ cells/kg to about $5 \times 10^6$ cells/kg, about $3 \times 10^6$ cells/kg to about $4 \times 10^8$ cells/kg, or any intervening dose of cells/kg.

In various embodiments, the methods of the invention provide more robust and safe gene therapy than existing methods and comprise administering a population or dose of cells comprising about 5% transduced cells, about 10% transduced cells, about 15% transduced cells, about 20% transduced cells, about 25% transduced cells, about 30% transduced cells, about 35% transduced cells, about 40% transduced cells, about 45% transduced cells, or about 50% transduced cells, to a subject.

In one preferred embodiment, the invention provides transduced cells, such as a stem cell, e.g., hematopoietic stem cell, with the potential to expand or increase a population of erythroid cells. In particular embodiments, hematopoietic stem cells are transduced with a vector of the invention and administered to an individual in need of therapy for hemoglobinopathy. Hematopoietic stem cells are the origin of erythroid cells and thus, are preferred.

In various embodiments, the vectors, compositions, and methods of the present invention offer improved methods of gene therapy using ex vivo gene therapy and autologous transplantation. In one non-limiting example, the present invention provides a lentiviral vector that encodes human β-globin and a truncated erythropoietin receptor, both under erythroid specific transcriptional control. This truncated receptor confers enhanced sensitivity to erythropoietin and a benign proliferative advantage on cells expressing the tEpoR in human carriers. Transplantation of cells transduced with the vector into subjects having hemoglobinopathies, and either having elevated plasma EPO levels or administered recombinant EPO, results in long-term correction of the disease even at low ratios of transduced/untransduced cells.

The present invention now will be described more fully by the following examples. This invention may, however, be embodied in many different forms and should not be construed as limited to the embodiments set forth herein; rather, these embodiments are provided so that this disclosure will be thorough and complete, and will fully convey the scope of the invention to those skilled in the art.

EXAMPLES

Example 1

Cell Culture, Transduction, and Bone Marrow Cell Transplantation

Hematopoietic stem cells (HSCs), also termed 5-fluorouracil (5-FU) cells in some embodiments, were obtained from bone marrow (BM) cells of male donor mice injected 4 days previously with 150 mg/kg 5-FU (Sigma-Aldrich) and submitted to Lympholyte-M density gradient purification (Cedarlane). In particular embodiments, HSCs were purified from male mouse BM by sorting $CD105^+$ $Sca1^+$ cells with the use of magnetic beads (Miltenyi Biotec). Medullar lymphomyeloid and erythroid cells were purified on the basis of the presence or absence of the CD45 antigen with magnetic beads (Miltenyi Biotec). Purity was checked by cytometry with antibodies against CD45 and Ter119 antigens.

Ecotropic pseudotyped retroviral vectors were generated by transient transfection of BOSC23 cells using Fugene (Roche Diagnostics, Meylan, France). Ecotropic retroviral vector titers were assessed by flow cytometry two days after NIH3T3 cells transduction. Recombinant lentiviral vectors pseudotyped with vesicular stomatitis virus glycoprotein-G were produced. Titers were about $2 \times 10^8$ transducing units per milliliter of viral supernatant.

Before transduction, cells were washed and suspended at a final concentration of $1-2 \times 10^6$ cells/mL in alpha-MEM medium (Invitrogen) containing 15% FCS, 100 ng/mL recombinant mouse stem cell factor, 6.25 ng/mL interleukin-3, and 10 ng/mL interleukin-6 and grown at 37° C. All cytokines were from Peprotech. Recombinant human erythropoietin (rhEpo; 3 U/mL; Roche Pharma) was added in erythroid cell culture.

Transduction of 5-FU cells with gammaretroviral vectors (RV) started 40 hours later. Cells were exposed twice, 24 hours apart, to undiluted retroviral supernatants on Retronectin (Takara)-coated Petri dishes in alpha-MEM medium containing 8 g/mL protamine sulfate (Sigma-Aldrich), decomplemented serum, and cytokines. Two days after transduction, percentages of enhanced green fluorescent protein-(eGFP)-positive cells (24%-32% as determined by flow cytometry and unchanged 4 days later) were set to 10% with mock transduced cells. Four million cells (including $4 \times 10^5$ eGFP-expressing cells) were injected intravenously in lethally irradiated β thalassemic female mice $Hbb^{th-1/th-1}$. In this experiment, MOI was 1 (twice). β thalassemic recipients received 1100 rads (split dose of 550 rads over 3 hours) of total body irradiation.

Cells were transduced with lentiviral vectors 16 hours after cell isolation. 5-FU cells were exposed to vectors on Retronectin-coated Petri dishes in StemPro-34 serum-free medium (Invitrogen) supplemented with protamine sulfate and cytokines. Six hours later, cells were harvested by the use of trypsin-EDTA solution (Cambrex BioScience) and a cell scraper. A total of 500,000-750,000 transduced 5-FU cells were injected intravenously into each β thalassemic female recipient given total body irradiation.

In experiment 1, MOI was 20, and the β thalassemic recipient received 600 rads (single dose).

In experiment 2, 3 groups of mice received cells transduced at MOI of 0.3, 2, or 10, respectively and 1100 rads (split dose of 550 rads over 3 hours). β thalassemic mice that underwent transplantation with cells transduced with the LG and the LG/HA-Y1 mice were called LG- and LG/HA-Y1 mice, respectively.

In a third experiment, after a single irradiation dose of 200 rads, 4 β thalassemic mice were injected with 25,000 $CD105^+$ $Sca1^+$ cells each. Cells were transduced with LG/HA-Y1 at a MOI of 20. For in vitro studies, bone marrow erythroid ($CD45^-$) and lympho/myeloid ($CD45^+$) cells were transduced with LG/HA-Y1 at a MOI of 50. RNA was extracted 2 days later.

Blood Parameters

Blood samples were analyzed for hemoglobin and blood cell counts with the use of an automated cell counter (Cell Dyn 3700; Abbot Diagnostic). Hematocrit values were obtained by the manual centrifugation method. The proportion of soluble hemoglobin versus total hemoglobin was determined by the measurement of hemoglobin with the Drabkin reagent (Sigma-Aldrich) in total hemolysate and in the supernatant of centrifuged (5 minutes at 20,000 g) hemolysate. Erythropoietin concentration was determined by use of the Epo monoclonal enzyme immuno-assay kit (Medac Diagnostika) with human Epo standards. Mouse and human hemoglobins were separated by cation-exchange HPLC. Hemolysates were injected onto a PolyCAT A column (PolyLC Inc). Elution was achieved with a linear gradient of 2 Tris buffers (buffer A: Tris 40 mM, KCN 3 mM adjusted to pH 6.5 with acetic acid; buffer B: Tris 40 mM, KCN 3 mM, NaCl 200 mM adjusted to pH 6.5 with acetic acid) from 7% to 70% buffer B in 15 minutes. Hemoglobins were detected at 418 nm wavelength.

Flow Cytometry eGFP-positive WBCs were detected after RBC lysis and labeling with a biotinylated antibody against CD45.2 (BD Biosciences) and streptavidin-Alexa Fluor 647 (Invitrogen). For the detection of intracellular human β-globin, RBCs were washed, fixed for 30 minutes in 2% formaldehyde, permeabilized for 30 seconds in 50% methanol and 50% acetone, and stained with an FITC-labeled antibody that specifically recognizes human HbA (PerkinElmerWallac). Myeloid and lymphoid BM cells were detected with the biotinylated anti-CD45.2 and either a PE anti-mouse GR1/Mac1, anti-mouse CD3, or anti-mouse B220 (all from eBiosciences) followed by streptavidin-Alexa Fluor 647 labeling. Erythroid progenitor cells were identified by the use of anti-mouse Ter119 and CD71 antigens.

Quantitative PCR and RT-quantitative PCR Analysis

Genomic DNA was extracted with the Nucleospin Blood kit (Macherey Nagel). The fraction of donor male cells among leukocytes (D) and the vector copy number (V) were determined by quantitative PCR, and results were compared with those for serial dilutions of genomic DNA from male and female cells and of genomic DNA from a mouse cell line containing one copy of an integrated vector per haploid genome. Real-time PCRs were performed for 40 cycles with denaturation at 94° C. for 15 seconds and annealing and extension at 60° C. for 1 minute after an activation step of 10 minutes at 95° C. with use of the 7300 ABI Prism Detection system (Applied Biosystems) and a 2× quantitative PCR (qPCR) MasterMix containing ROX (Eurogentec). Primers and probes are described in Table 1.

TABLE 1

Primers and probes used for real-time PCR

| Name | Sequence or Taqman gene expression assay number* | Modification | Conc. |
|---|---|---|---|
| LV-GAGF | 5' GGAGCTAGAACGATTCGCAGT TA 3' | | 720 nM |
| LV-GAGR | 5' GGTTGTAGCTGTCCCAGTATT TGTC 3' | | 720 nM |
| LV-GAGP1 | 5' ACAGCCTTCTGATGTCTCTAA AAGGCCAGG 3' | 5' FAM 3' TAMRA | 140 nM |
| mβ-actinF1 | 5' ACGGCCAGGTCATCACTATTG 3' | | 900 nM |
| mβ-actinR1 | 5' CAAGAAGGAAGGCTGGAAAAG A 3' | | 900 nM |
| mβ-actinP1 | 5' CAACGAGCGGTTCCGATGCCC T 3' | 5' FAM 3' TAMRA | 250 nM |
| SRY | Mm00441712_s1 | 5' FAM 3' NFQ-MGB | 1X |
| EpoR | Mm00833882_m1 | 5' FAM 3' NFQ-MGB | 1X |
| GAPDH | Mm99999915_g1 | 5' FAM 3' NFQ-MGB | 1X |
| 18s | Hs99999901_s1 | 5' FAM 3' NFQ-MGB | 1X |

EpoR indicates erythropoietin receptor; FAM, 6-carboxyfluorescein ester; LV, lentiviral vector; NFQ, nonfluorescent quencher; MGB, minor groove binder; SRY, sex-determining region Y and TAMRA, tetramethyl-6-carboxyrhodamine.
*Applied Biosystems.

Total RNA was extracted with the Purelink micro to midi total RNA purification system (Invitrogen) and cDNA was synthesized with the Superscript III first-strand synthesis super mix (Invitrogen). The mouse (m) EpoR, mGAPDH, and 18s cDNAs were quantified with the use of TaqMan gene expression assays (Table 1). The comparative Ct method ($\Delta\Delta$CT) was used to compare mEpoR production levels between cell types. Control samples from which the reverse transcriptase or the sample had been omitted were included.

Amplification Factor of Modified Erythroid Cells

The effect of tEpoR and β-globin on erythroid cell expansion was calculated on the basis of the comparison between modified WBC and RBC percentages in peripheral blood. The percentage of modified RBCs (% RBC) was determined by flow cytometry with an anti-human HbA antibody. The percentage of modified WBCs (% WBC) was determined from the vector copy numbers per leukocyte (V) and the fraction of donor male cells (D). It was calculated as follows:

the vector copy number per donor leukocyte $V^d = V/D$;
the percentage of modified WBCs among donor cells % $WBC^{+d}$ was determined from $V^d$ according to the Poisson law: % $WBC^{+d} = [1 - \exp(-V^d)] \times 100$; and
the percentage of modified WBCs among all leukocytes % $WBC^+ = \% WBC^{+d} \times D$.

Assuming that modified WBCs have no advantage or disadvantage over unmodified WBCs in vivo, the amplification factor of modified erythroid cells ($F^E$) resulting from the survival benefit provided to modified erythrocytes and the production advantage conferred to modified erythroid cells in the bone marrow was calculated as follows:

$$F^E = (\% RBC^+/\% RBC^-)/(\% WBC^+/\% WBC^-) \quad \text{(eq 1)}$$

As a consequence, (% $RBC^+$/% $RBC^-$) = $F^E$(% $WBC^+$/% $WBC^-$) (eq 2), and the hyperbolic relationship between % $RBC^+$ and % $WBC^+$ is described by the following:

$$\% RBC^+ = \{F^E[(100/(F^E-1)] \times \% WBC^+\}/\{[100/(F^E-1)] + \% WBC^+\} \quad \text{(eq 3)}$$

This mathematical model was derived from Roberts et al., Ann NY Acad Sci. 2005; 1054: 423-428, assumes a steady-state balance between destruction and production of WBCs and RBCs.

To assess that modified leukocyte were not affected by tEpoR, the fractions of in vivo-modified WBC and ex vivo-modified HCs were calculated, divided, and compared between mice undergoing transplantation with LG- and LG/HA-Y1-transduced cells.

Integration Site Analysis

Genomic DNA from vector-infected cells was purified and linkers added for PCR by treatment with phage MuA transposase and synthetic oligonucleotides containing MuA recognition sites. Genomic DNA adjacent to integrated vectors was then amplified by the use of PCR primers complementary to the vector DNA end and the linker. Sequences of PCR products were determined by 454/Roche pyrosequencing, and data were curated and analyzed. The Mu transposition method provides an estimate of abundance, in which the number of independent Mu integration events in vitro that result in isolation of a single Mu site reports the relative abundance. In a few cases, integration sites were found in more than one mouse. These cases could either be because of the growth of transduced cells before transplantation or because of crossover during PCR. In these cases, integration sites were assigned to a single mouse on the basis of relative abundance. Proximity of integration sites to proto-oncogenes was determined by comparison with the allOnco database (Cancer gene data sets. Available at microb230.med.upenn.edu/protocols/cancer-genes.html. Accessed Apr. 5, 2011).

Statistical Analysis

For 2 group comparisons, Student t test or Mann-Whitney rank-sum test were used. For comparison of more than 2 groups, one-way analysis of variance and the Holm-Sidak or the Kruskal-Wallis on ranks methods were used. Linear regression was applied to data with determination of the correlation coefficient ($R^2$) and the P value. All tests were performed with the SigmaPlot Version 10.0 software. $P < 0.05$ was considered significant.

Example 2 tEpoR-Expressing HCs Possess a Proliferative Advantage in β Thalassemic Mice

Background

A β-thalassemia mouse model that has constitutively elevated levels of plasma Epo (20- to 50-fold normal mouse values) was used to examine the expansion of bone marrow cells, transduced with a vector that ubiquitously expresses tEpoR, that were transplanted into syngeneic recipients.

Figure 1C:
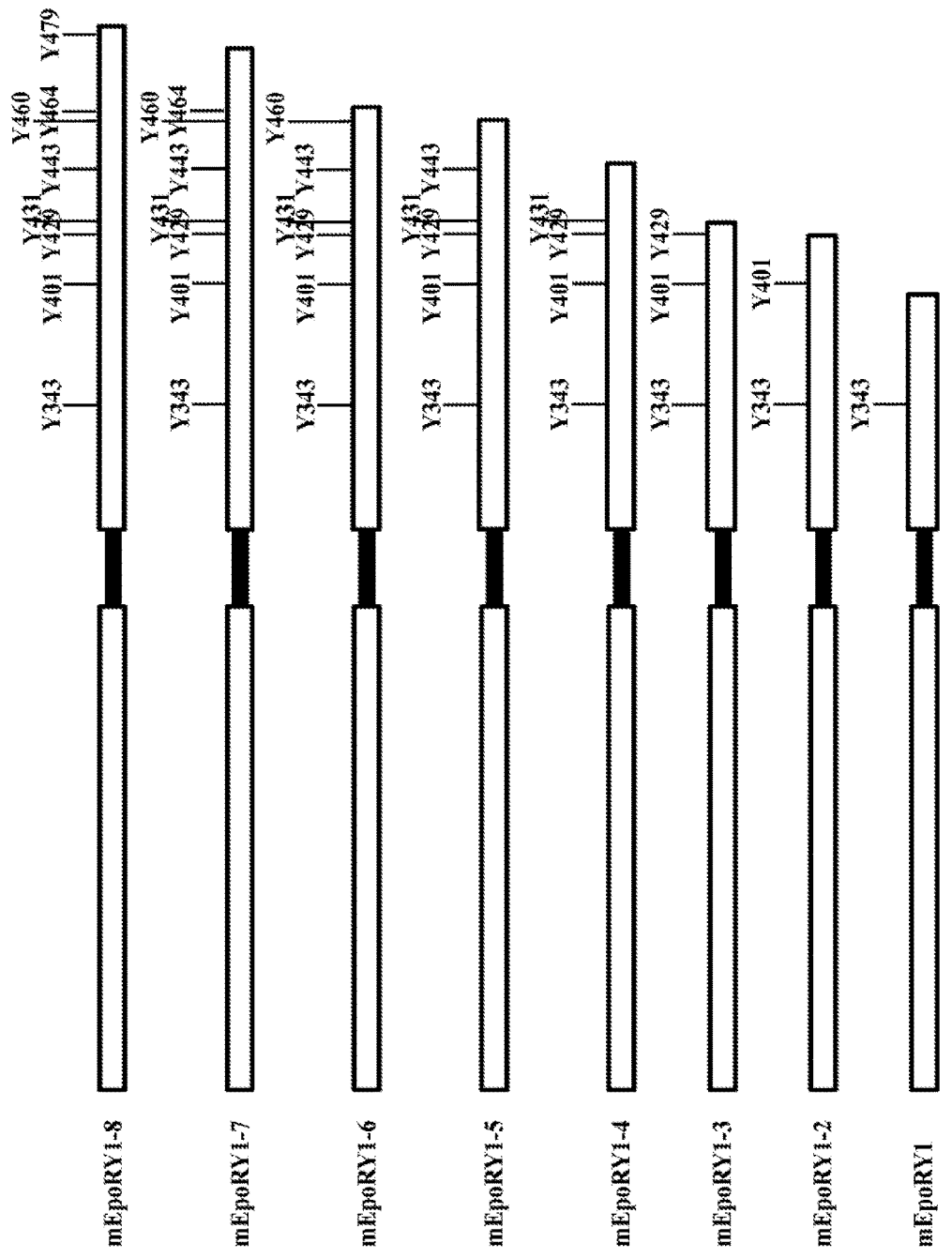
Figure 1D:
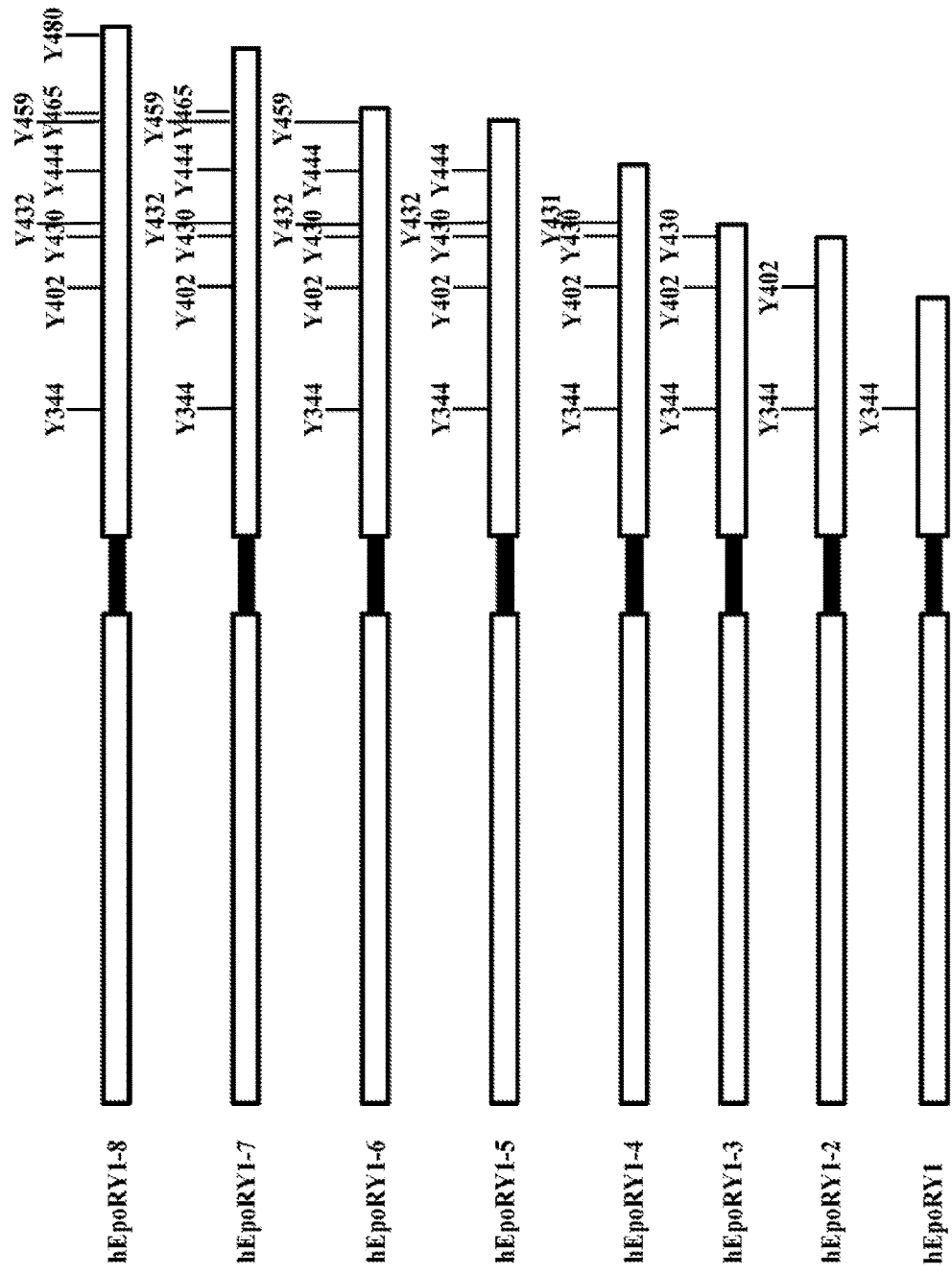

Gammaretroviral vectors (γRVs) expressing the EpoR cDNAs and eGFP ubiquitously were constructed. These γRVs encode the full-length murine EpoR (mEpoRY1-8), either of the 2 truncated receptors (mEpoRY1-2 or mEpoRY1) or eGFP only (FIGS. 1A-1C). All constructs were shown to express efficient Epo receptors in Ba/F3 cells. mEpoRY1-8 was also shown to be functional in UT7-GM cells.

BM cells from β thalassemic donors were transduced with the 4 γRVs described above. Four million cells, including 10% genetically modified cells, were injected into lethally irradiated β thalassemic recipients.

Results

Twenty weeks after transplantation, 5.5% and 3.1% eGFP-positive RBCs and WBCs, respectively, were detected in the blood of mice transplanted with cells modified by the control γRV (FIG. 2A).

Mice receiving γRV/EpoRY1-8-transduced cells showed no significant amplification of their eGFP-positive RBC (2.7%) and WBC (4.1%) populations over those of control mice. Separate analysis of lymphoid and myeloid compartments also did not show specific hematopoietic cell type amplification (FIG. 9 and Table 2).

were not statistically different between the erythroid and the myeloid compartment (Table 3), indicating that tEpoR did not exert a preferential effect in erythroid over myeloid cells.

TABLE 3

| Vector | WBC | LYMPHO | GM |
|---|---|---|---|
| γRV | 0.592 | 0.521 | 0.548 |
| γRV/EpoRY1 | 0.516 | 0.518 | 0.401 |
| γRV/EpoRY1-2 | <0.001 | <0.001 | 0.937 |
| γRV/EpoRY1-8 | 0.132 | 0.132 | 0.132 |

Statistical significance of differences (p values) between the mean or median percentages of GFP positive cells in RBC versus white blood cells (WBC), lymphoid cells (LYMPHO) and myeloid cells (GM).

To determine whether EpoR was expressed at a lower level than truncated receptors, we compared the eGFP mean fluorescence intensities (MFI) in transduced HCs grown in vitro and after transplantation. The MFI of the transduced

TABLE 2

| | Vector | Mean | SD | SE | Median | 25th | 75th | p-value |
|---|---|---|---|---|---|---|---|---|
| WBC | γRV | 3.066 | 2.973 | 1.330 | 1.370 | 0.728 | 5.972 | |
| | γRV/EpoRY1 | 30.836 | 11.958 | 5.348 | 25.430 | 22.712 | 43.335 | 0.001 |
| | γRV/EpoRY1-2 | 17.683 | 6.704 | 2.737 | 15.900 | 13.510 | 19.340 | 0.002 |
| | γRV/EpoRY1-8 | 4.138 | 4.929 | 2.012 | 3.125 | 0.870 | 3.860 | 0.931 |
| LYMPHO | γRV | 2.602 | 2.648 | 1.184 | 1.020 | 0.867 | 4.500 | |
| | γRV/EpoRY1 | 30.888 | 11.813 | 5.348 | 29.670 | 21.153 | 42.650 | 0.008 |
| | γRV/EpoRY1-2 | 15.705 | 5.502 | 2.246 | 14.685 | 11.630 | 18.820 | <0.001 |
| | γRV/EpoRY1-8 | 4.830 | 6.877 | 2.807 | 2.465 | 0.940 | 4.460 | 0.792 |
| GM | γRV | 5.428 | 5.832 | 2.608 | 1.770 | 1.198 | 11.355 | |
| | γRV/EpoRY1 | 57.668 | 39.524 | 17.676 | 77.440 | 22.790 | 86.645 | 0.019 |
| | γRV/EpoRY1-2 | 48.970 | 28.053 | 11.452 | 45.270 | 25.580 | 71.130 | 0.004 |
| | γRV/EpoRY1-8 | 4.503 | 4.672 | 1.907 | 3.290 | .0580 | 7.330 | 0.776 |
| RBC | γRV | 5.502 | 9.291 | 4.155 | 0.820 | 0.253 | 8.855 | |
| | γRV/EpoRY1 | 39.180 | 24.736 | 11.062 | 38.350 | 22.802 | 55.150 | 0.021 |
| | γRV/EpoRY1-2 | 42.972 | 7.625 | 3.113 | 43.960 | 36.850 | 47.690 | <0.001 |
| | γRV/EpoRY1-8 | 2.672 | 5.909 | 2.412 | 0.020 | 0.020 | 1.270 | 0.247 |

Mean, standard deviation (SD), standard error (SE), median value, 25th percentile, 75th percentile and significance of differences (p value) between the mean or median percentages of eGFP positive cells in the control group (RV) versus the other groups of mice in white blood cells (WBC), lymphoid cells (LYMPHO), myeloid cells (GM) and red blood cells (RBC).

Mice receiving γRV/EpoRY1-transduced cells had 39.2% and 30.8% amplification of eGFP-positive RBCs and WBCs, respectively. This represented a 7-fold (P=0.021) and 10-fold (P=0.001) increase of modified RBC and WBC proportions compared with the control group, respectively. In mice receiving γRV/EpoRY1-2, the mean amplification levels of modified RBC and WBC proportions were 8- and 6-fold, respectively.

Thus, the mean percentages of eGFP-positive cells in γRV/EpoRY1 and γRV/EpoRY1-2 mice were significantly different from the mean value observed in the γRV/EpoRY1-8-transduced group.

Myeloid cells were examined to determine whether the proportion of eGFP-positive cells that was greater in RBCs than in WBCs was because of persistence of recipient radioresistant memory lymphoid cells. The median values of the percentages of eGFP-positive cells showed a trend toward greater values in granulo/monocytes than in lymphocytes in γRV/EpoRY1-2 mice (P=0.009) and in γRV/EpoRY1 animals. The percentages of eGFP-positive cells cells before transplantation were equivalent with all vectors (FIG. 10). EpoRY1 and EpoRY1-8 mRNAs, quantified by qRT-PCR in CD45$^+$ cells sorted for eGFP expression 10 days after transduction, were similar. However in mice, there were statistically significant differences of MFI between γRV/EpoRY1 and γRV (P=0.031) and γRV/EpoRY1 and γRV/EpoRY1-8 (P 0.017) in the myeloid compartment. The 4 mice with the greatest MFI in granulocytes had the greatest percentage of modified myeloid cells. No difference was observed between γRV and γRV/EpoRY1-8 mice in any cell types.

Together, these results indicated that the absence of selection with the wild-type EpoR was not because of a lower level of expression of EpoR but that myeloid cells expressing the greatest level of EpoR-Y1 were favored over cells expressing lower levels of truncated EpoR. The blood counts (Table 4) were not statistically different between groups. However, plasma Epo levels were 2.5-fold lower (P=0.005) in the γRV/EpoRY1 and γRV/EpoRY1-2 transplanted mice than in the 2 other groups (FIG. 2B).

TABLE 4

| Vector - γRV/ | | Mean | SD | SE | Range | Max | Min | Median | 25th | 75th |
|---|---|---|---|---|---|---|---|---|---|---|
| Hc (%) | | 29.9 | 1.6 | 0.7 | 4.3 | 32.4 | 28.1 | 29.6 | 29.2 | 30.5 |
| | EpoRY1 | 30.3 | 1.9 | 0.8 | 4.8 | 32.6 | 27.6 | 31.0 | 28.7 | 31.4 |
| | EpoRY1-2 | 31.7 | 2.8 | 1.2 | 7.6 | 34.7 | 27.1 | 31.9 | 30.4 | 34.1 |
| | EpoRY1-8 | 29.0 | 1.4 | 0.6 | 3.1 | 30.2 | 27.1 | 29.7 | 27.3 | 30.1 |
| RBC | | 8.3 | 0.2 | 0.1 | 0.5 | 8.5 | 8.0 | 8.3 | 8.2 | 8.4 |
| ($\times 10^{12}$/L) | EpoRY1 | 8.5 | 1.0 | 0.4 | 2.4 | 9.5 | 7.2 | 8.6 | 7.9 | 9.4 |
| | EpoRY1-2 | 8.5 | 0.8 | 0.3 | 2.3 | 9.5 | 7.2 | 8.5 | 8.1 | 9.2 |
| | EpoRY1-8 | 8.0 | 0.4 | 0.1 | 0.9 | 8.6 | 7.7 | 7.9 | 7.7 | 8.3 |
| Hb (g/dL) | | 9.7 | 0.7 | 0.3 | 2.0 | 10.8 | 8.8 | 9.8 | 9.3 | 10.1 |
| | EpoRY1 | 9.8 | 0.6 | 0.3 | 1.7 | 10.4 | 8.8 | 9.9 | 9.5 | 10.3 |
| | EpoRY1-2 | 10.0 | 0.8 | 0.3 | 2.2 | 10.8 | 8.7 | 10.0 | 9.6 | 10.8 |
| | EpoRY1-8 | 9.7 | 0.4 | 0.2 | 1.0 | 10.3 | 9.3 | 9.7 | 9.3 | 9.9 |
| WBC | | 9.7 | 3.0 | 1.4 | 8.0 | 13.8 | 5.8 | 9.1 | 7.9 | 12.0 |
| ($\times 10^9$/L) | EpoRY1 | 8.1 | 1.6 | 0.7 | 4.4 | 10.4 | 6.0 | 8.4 | 7.0 | 9.1 |
| | EpoRY1-2 | 9.8 | 1.3 | 0.5 | 3.7 | 118. | 8.1 | 9.7 | 9.0 | 10.8 |
| | EpoRY1-8 | 8.0 | 202 | 0.9 | 5.0 | 10.8 | 5.8 | 7.7 | 5.9 | 10.1 |
| neutrophils | | 0.4 | 0.1 | 0.0 | 0.2 | 0.5 | 0.4 | 0.4 | 0.4 | 0.5 |
| ($\times 10^9$/L) | EpoRY1 | 0.5 | 0.2 | 0.1 | 0.3 | 0.6 | 0.3 | 0.5 | 0.3 | 0.6 |
| | EpoRY1-2 | 0.5 | 0.1 | 0.1 | 0.4 | 0.6 | 0.2 | 0.5 | 0.5 | 0.6 |
| | EpoRY1-8 | 0.3 | 0.2 | 0.1 | 0.6 | 0.7 | 0.1 | 0.3 | 0.2 | 0.4 |
| monocytes | | 0.4 | 0.1 | 0.0 | 0.2 | 0.5 | 0.4 | 0.4 | 0.4 | 0.5 |
| ($\times 10^9$/L) | EpoRY1 | 0.5 | 0.2 | 0.1 | 0.3 | 0.6 | 0.3 | 0.5 | 0.3 | 0.6 |
| | EpoRY1-2 | 0.5 | 0.1 | 0.1 | 0.4 | 0.6 | 0.2 | 0.5 | 0.5 | 0.6 |
| | EpoRY1-8 | 0.3 | 0.2 | 0.1 | 0.6 | 0.7 | 0.1 | 0.3 | 0.2 | 0.4 |
| lymphocytes | | 8.2 | 3.1 | 1.4 | 8.5 | 12.6 | 4.2 | 7.7 | 6.4 | 10.2 |
| ($\times 10^9$/L) | EpoRY1 | 6.6 | 1.3 | 0.6 | 3.6 | 8.4 | 4.9 | 6.6 | 5.8 | 7.3 |
| | EpoRY1-2 | 8.2 | 1.3 | 0.5 | 4.1 | 10.4 | 6.3 | 8.0 | 7.7 | 8.5 |
| | EpoRY1-8 | 6.8 | 2.1 | 0.9 | 5.0 | 9.5 | 4.5 | 6.5 | 4.6 | 8.9 |
| eosinophils | | 0.0 | 0.0 | 0.0 | 0.1 | 0.1 | 0.0 | 0.0 | 0.0 | 0.0 |
| ($\times 10^9$/L) | EpoRY1 | 0.0 | 0.0 | 0.0 | 0.0 | 0.0 | 0.0 | 0.0 | 0.0 | 0.0 |
| | EpoRY1-2 | 0.0 | 0.0 | 0.0 | 0.1 | 0.1 | 0.0 | 0.0 | 0.0 | 0.0 |
| | EpoRY1-8 | 0.0 | 0.0 | 0.0 | 0.0 | 0.0 | 0.0 | 0.0 | 0.0 | 0.0 |
| basophils | | 0.3 | 0.1 | 0.0 | 0.2 | 0.4 | 0.2 | 0.3 | 0.2 | 0.4 |
| ($\times 10^9$/L) | EpoRY1 | 0.4 | 0.2 | 0.1 | 0.5 | 0.6 | 0.1 | 0.4 | 0.2 | 0.5 |
| | EpoRY1-2 | 0.4 | 0.1 | 0.0 | 0.3 | 0.6 | 0.3 | 0.4 | 0.3 | 0.5 |
| | EpoRY1-8 | 0.2 | 0.1 | 0.0 | 0.3 | 0.3 | 0.1 | 0.2 | 0.1 | 0.2 |
| MCV (fL) | | 36.2 | 1.3 | 0.6 | 3.2 | 38.3 | 35.1 | 36.0 | 35.4 | 36.6 |
| | EpoRY1 | 35.7 | 3.5 | 1.6 | 7.9 | 40.6 | 32.6 | 34.3 | 32.9 | 38.7 |
| | EpoRY1-2 | 37.5 | 2.0 | 0.8 | 5.8 | 40.8 | 35.0 | 37.5 | 36.1 | 37.9 |
| | EpoRY1-8 | 36.4 | 1.2 | 0.54 | 3.1 | 38.3 | 35.2 | 36.0 | 35.4 | 37.1 |
| MCH (pg) | | 11.8 | 0.7 | 0.3 | 1.8 | 12.7 | 10.9 | 11.9 | 11.2 | 12.1 |
| | EpoRY1 | 11.6 | 0.9 | 0.4 | 1.9 | 12.2 | 10.3 | 12.2 | 10.8 | 12.2 |
| | EpoRY1-2 | 11.8 | 0.4 | 0.2 | 1.2 | 12.5 | 11.3 | 11.7 | 11.4 | 12.1 |
| | EpoRY1-8 | 12.1 | 0.2 | 0.1 | 0.4 | 12.4 | 11.9 | 12.1 | 12.0 | 12.3 |
| MCHC | | 32.5 | 0.9 | 0.4 | 2.0 | 33.2 | 31.1 | 33.1 | 31.7 | 33.1 |
| (g/dL) | EpoRY1 | 32.4 | 2.0 | 0.9 | 5.3 | 35.4 | 30.2 | 31..9 | 31.3 | 33.7 |
| | EpoRY1-2 | 31.5 | 2.0 | 0.8 | 5.4 | 33.1 | 27.7 | 32.1 | 31.5 | 32.6 |
| | EpoRY1-8 | 33.4 | 0.3 | 0.3 | 2.1 | 34.3 | 32.2 | 33.5 | 32.8 | 34.1 |
| Platelets | | 954.7 | 395.9 | 177.1 | 1001.5 | 1485.0 | 483.5 | 845.0 | 679.6 | 1282.5 |
| ($\times 10^9$/L) | EpoRY1 | 717.5 | 190.3 | 85.1 | 517.5 | 955.0 | 437.5 | 705.0 | 619.4 | 846.3 |
| | EpoRY1-2 | 761.2 | 273.6 | 111.7 | 753.0 | 1200.0 | 447.0 | 730.0 | 550.0 | 910.0 |
| | EpoRY1-8 | 914.0 | 340.7 | 139.1 | 866.0 | 1250.0 | 384.0 | 962.5 | 675.0 | 1250.0 |
| Epo | | 74.0 | 26.0 | 11.6 | 70.5 | 113.8 | 43.3 | 68.9 | 58.5 | 88.8 |
| (mU/mL) | EpoRY1 | 30.2 | 19.3 | 8.6 | 45.5 | 57.8 | 12.3 | 20.4 | 16.5 | 46..5 |
| | EpoRY1-2 | 29.6 | 7.2 | 2.9 | 19.0 | 41.0 | 22.0 | 27.8 | 23.8 | 35.1 |
| | EpoRY1-8 | 86.3 | 59.2 | 24.2 | 169.3 | 197.7 | 28.4 | 66.5 | 58.6 | 100.5 |

Mean, standard deviation (SD), standard error (SE), range, maximal, minimal and median values, 25th percentile, 75th percentile of the hematocrit values (Hc), red blood cell counts (RBC), hemoglobin concentrations (Hb), white blood cell counts (WBC) and specific cell subsets, mean corpuscular volumes (MCV), mean corpuscular hemoglobin contents (MCH), mean corpuscular hemoglobin concentrations (MCHC), platelet counts and plasma erythropoietin levels (Epo) in four groups of mice transplanted twenty weeks earlier.

Example 3

A Chimeric HS40/Ankyrin Promoter is Erythroid Specific within the β-Globin/LCR Lentiviral Vector Background A lentiviral vector was designed to express tEpoR in a erythroid-cell specific manner to restrict cell expansion to the RBC compartment. The possible effects of transcriptional interference within the compact lentiviral provirus containing both the human β-globin gene driven the erythroid specific β-globin promoter/LCR enhancer and the tEpoR cDNA expression cassettes were assessed. To express tEpoR, the human β-globin HS40 enhancer was linked to the Ankyrin-1 promoter (Moreau-Gaudry et al., Blood, 2001; 98(9):2664-2672) referred to as HA.

To assess the level of erythroid specificity, eGFP was first introduced in the globin/LCR lentiviral vector LG (FIG. 1B), yielding the LG/HA-eGFP vector. The lentiviral vector HPV570 was used as a control vector that expresses eGFP ubiquitously. BM cells from normal C57BL/6J-CD45.2 mice were transduced with these vectors and injected in congenic C57BL/6JCD45.1 mice.

Results

Figure 3:
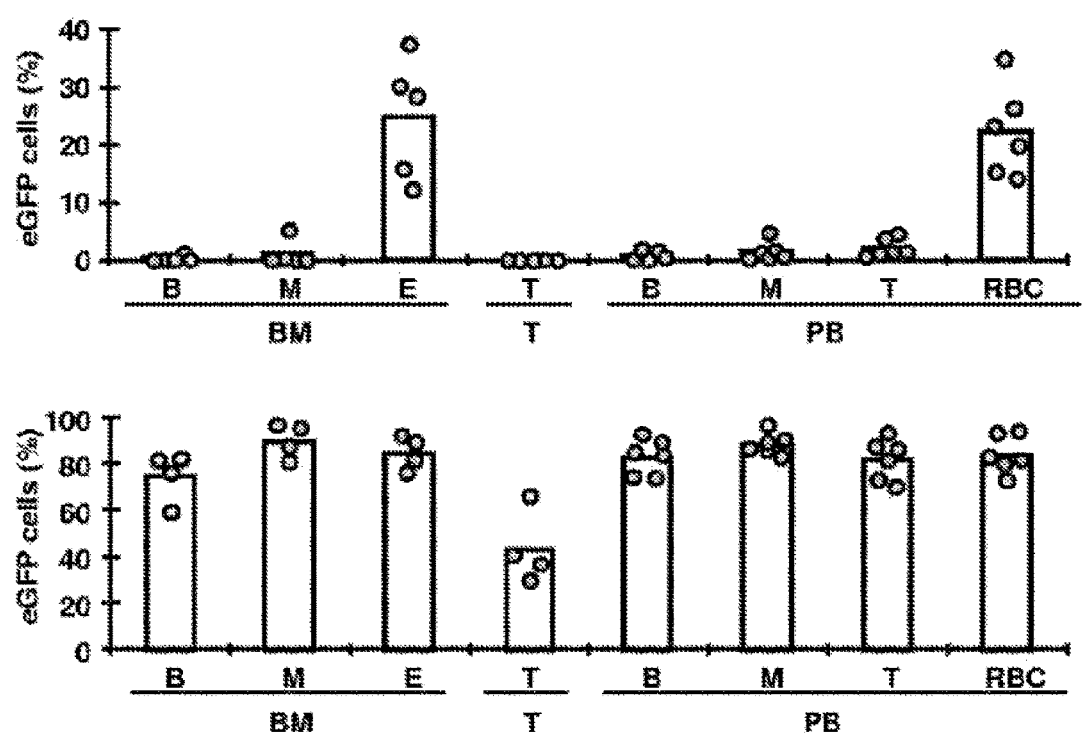
FIG. 3 shows strict erythroid specific expression of eGFP conferred by the HA promoter within the LG vector. Mean percentages and individual values of eGFP-positive cells in BM (B lymphoid [B], myeloid [M], and erythroid [E]), thymus (T lymphoid [T]), and peripheral blood (B, M, T, and RBCs) of normal mice transplanted with (top) LG/HA-eGFP or (bottom) HPV570 (EF1α-eGFP) transduced cells. For leukocytes, donor cells were identified by CD45.2 antigen expression.

The HA promoter in the context of the LG vector shows a high degree of erythroid specificity without interference from the β-globin/LCR cassette. Analysis of cells grown in vitro revealed 0.14 and 1.50 provirus copies per cell for LG/HA-eGFP and HPV570, respectively. Donor chimerism in circulating WBCs, 5 months after transplantation, were similar (approximately 90% CD45.2-positive WBCs). At the same time point, the percentages of eGFP-positive peripheral subsets of WBCs (myeloid, T-lymphoid, and B-lymphoid) and eGFP-positive RBCs were determined by flow cytometry. At 6 months after transplantation, cells from BM and thymus were analyzed by flow cytometry with the same antibodies as well as with antibodies for the erythroid lineage. The percentages of eGFP-positive myeloid, lymphoid, and erythroid cells were equivalent in mice that underwent transplantation with HPV570-modified cells, whereas the percentages of eGFP-positive erythroblasts and RBCs were much greater than the percentages of myeloid and lymphoid eGFP cells in mice that underwent transplantation with LG/HA-eGFP-modified cells (FIG. 3).

Erythroid specific expression was maintained when eGFP was replaced by tEpoR. tEpoR expression in modified erythroid and nonerythroid cells was compared. BM cells from a non-β thalassemic mouse were purified on the basis of the presence or absence of the pan-leukocyte CD45 antigen and then transduced with the LG/HA-EpoRY1 vector. Two days later, RNA was extracted and analyzed by RT-qPCR. Expression of tEpoRY1 in transduced erythroid CD45$^-$ (>99% Ter119$^+$) cells was more than 100-fold greater than in transduced CD45$^+$ (<1% Ter119$^+$) cells (147- and 109-fold when normalized to GAPDH and ribosomal 18s RNAs, respectively). Endogenous EpoR mRNA was undetectable by this method in nontransduced CD45$^+$ or CD45$^-$ cells, indicating that the 100-fold increase of EpoR mRNA observed in erythroid versus nonerythroid cells was from transgenic EpoR and resulted from the specificity of the Ankyrin promoter.

Example 4

Erythroid Specific tEpoR and β-Globin Coexpression and Selective Expansion of Erythroid Cells in Transplanted β Thalassemic Mice Background In view of the substantially similar effects of the γRV/EpoRY1 and γRV/EpoRY1-2 vectors (FIGS. 1A-1D), EpoRY1 were for subsequent mouse transplant experiments with the LG vectors.

The percentages of RBCs and WBCs in β thalassemic mice transplanted with syngeneic β thalassemic marrow cells transduced with either the LG or the LG/HA-Y1 vector were compared. Blood cell counts, percentage of RBC-expressing human Hb, level of human β-globin expression, degree of donor chimerism, and vector copy numbers were determined 40 or 35 weeks after transplantation.
Results The relationship between the percentages of RBCs versus WBCs is shown (FIG. 4A-B). Values were compared with 4 theoretical curves (derived from equations 2 and 3 described in the section "Amplification factor of modified erythroid cells" in Example 1), where the theoretical expansion of modified RBCs ($F^E$) would be 1-, 10-, 50-, or 200-fold greater than the expansion of modified WBCs. For most of the LG/HA-EpoRY1 mice, RBCs$_+$ were expanded 50- and 200-fold over WBCs$^+$, whereas RBCs$_+$ of LG mice only expanded only between 1- and 10-fold over WBCs$^+$. The median erythroid amplification factor $F^E$ for LG/HA-EpoRY1 and LG mice were 97.2 (range, 8.2-729.7) and 5.0 (range, 0.5-14.4), respectively (FIG. 4C).

The apparent advantage for tEpoR modified erythroid cells was determined to be specific to erythroid cells and not a disadvantage conferred to modified WBCs. Further, it was determined that tEpoR modified WBCs had no advantage over unmodified WBCs cells. The fraction of WBCs$^+$ among donor WBCs was determined and compared with the fraction of transduced bulk HCs before transplantation (10 days after transduction, without addition of recombinant human Epo; FIG. 4D). The median ratio of the fractions were equivalent (P=0.21) and close to 1, indicating that there was neither disadvantage nor benefit to modified WBCs over unmodified donor WBCs cells in vivo. Copy numbers were also measured in HCs grown with Epo and were similar to those determined in cells grown without Epo, indicating that Epo did not confer a proliferation advantage to transduced cells in vitro.

Example 5

Correction of the β Thalassemic Phenotype Correlates to the Proportion of Circulating RBCs that Express the Therapeutic Human β-Globin Background The LG/HA-EpoRY1 vector corrects the β-thalassemia disease phenotype. The β-thalassemia disease phenotype was assessed for a given proportion of circulating RBCs in both LG and LG/HA-EpoRY1 mice (i.e., mice administered LG or LG/HA-EpoRY1 transduced marrow cells). Hematologic parameters, Hb concentrations, as well as RBC and reticulocyte counts of LG and LG/HA-EpoRY1 mice as a function of RBC were recorded. It was previously shown that correction of the β-thalassemia phenotype was evident with the LG vector provided that the percentage of RBC$^+$ was >40%.

Results

Figure 5A:
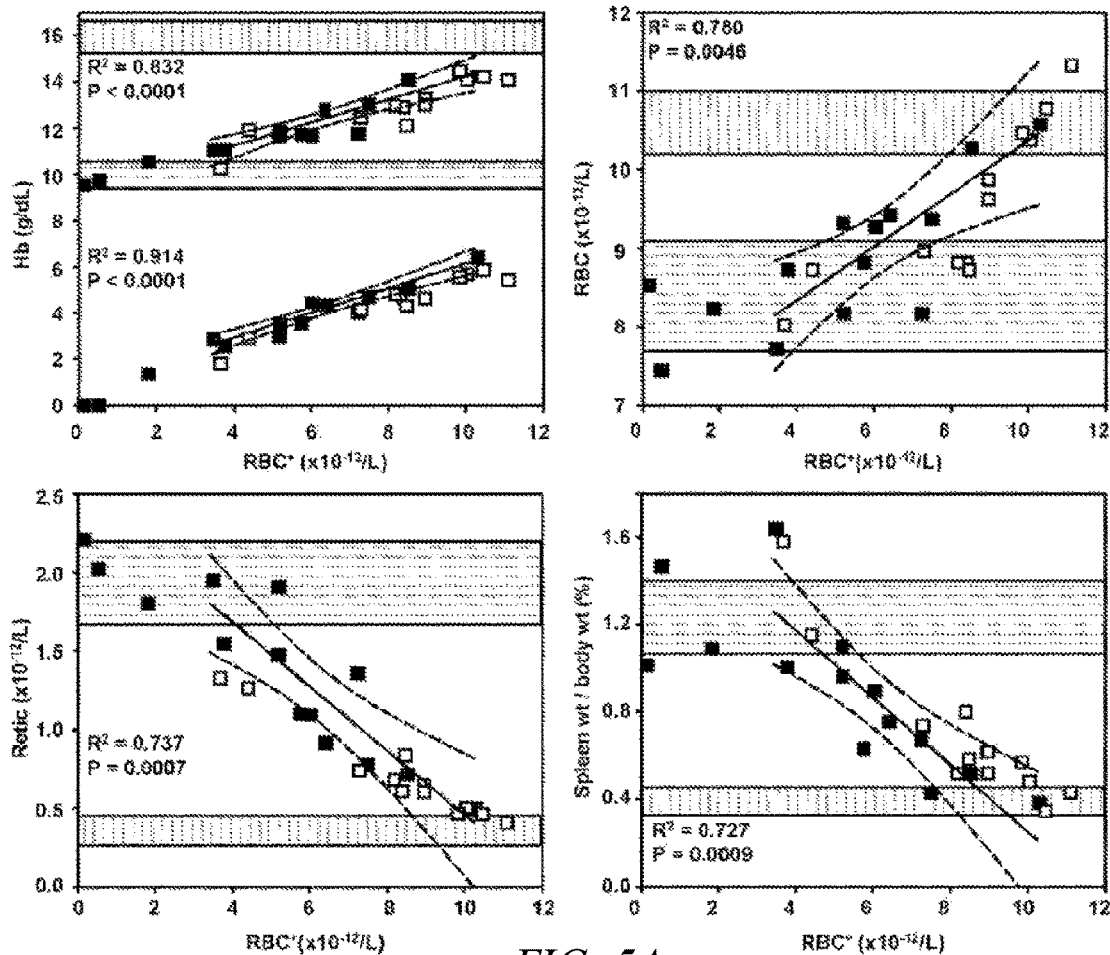
FIGS. 5A-5B show that correction of anemia and dyserythropoiesis depends, in part, on the level of modified RBC, independently of the presence of tEpoR in the vectors. Mice transplanted with LG/HA-EpoRY1 (□) or LG (■) transduced marrow cells.

Linear regressions were applied to the data obtained from LG mice with a threshold in excess of 40% RBCs$^+$, in all but 3 mice. Significant correlations (FIGS. 5A and 5B) between the level of RBC$^+$ and normalization of (1) concentration of total Hb, (2) concentration of human β-globin$^{AT87Q}$, (3) RBC counts, (4) reticulocyte counts, and (5) spleen weight were found within the group of mice receiving LG transduced marrow cells (FIG. 5A).

Linear regressions were applied to the data obtained from LG/HA-EpoRY1 mice with a threshold in excess of 40% RBCs$^+$.

Most of the hematologic values measured in LG/HA-EpoRY1 mice undergoing transplantation fell within the 95% confidence band for the fitted regression lines corresponding to all the measured parameters.

The percentages of erythroid cells were then measured within the spleens of 5 LG, 5 LG/HA-EpoRY1, and 3 mock-transplanted mice.

Figure 5B:
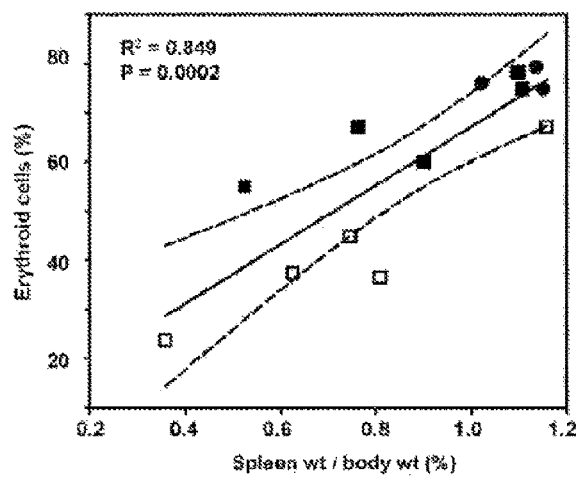

The decrease in spleen size was associated with a decrease in the percentage of spleen erythroid cells in both groups of mice, consistent with decreased dyserythropoiesis and improved efficiency of terminal erythroid cell differentiation (FIG. 5B). Together, these data indicated that the correction of the β thalassemic phenotype correlated to the proportion of circulating RBCs that expressed the therapeutic human β-globin in similar proportion for both LG and LG/HA-EpoRY1 groups of mice, with an accessory benefit provided by tEpoR expression.

Example 6

Figure 6A:
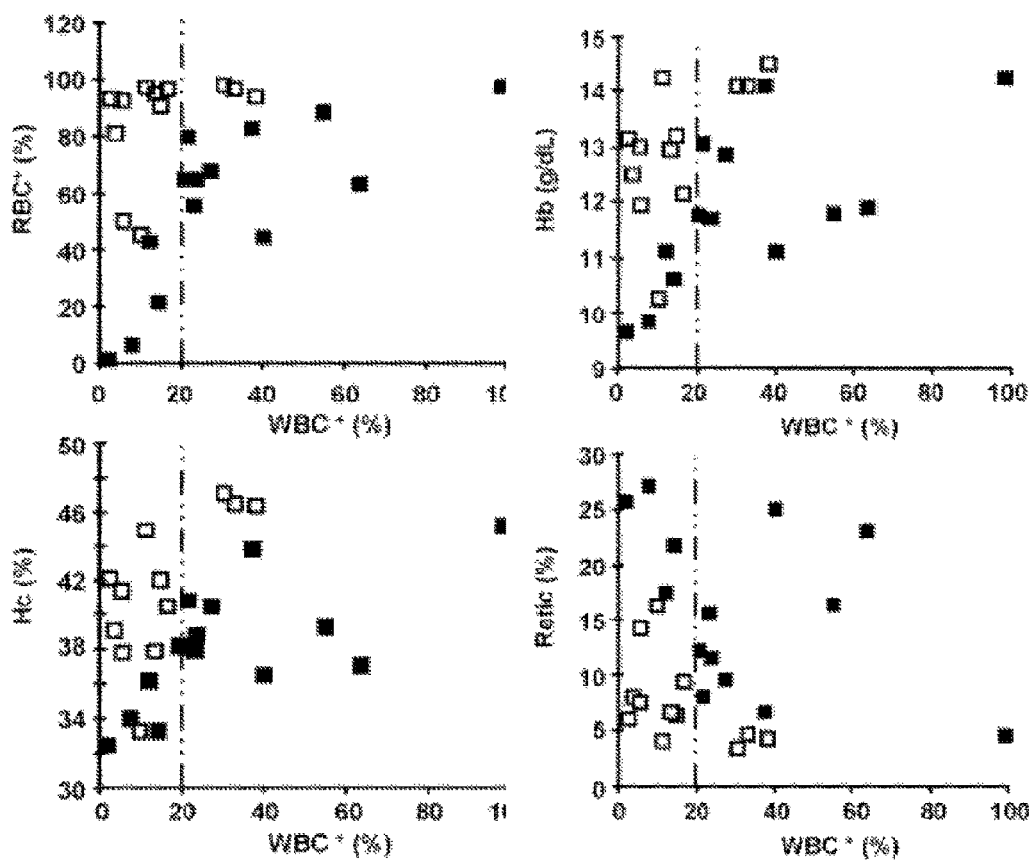
FIGS. 6A-6B show that anemia is corrected at lower levels of modified WBCs when tEpoR is coexpressed with the therapeutic globin gene. Mice transplanted with LG/HA-EpoRY1 (□) or LG (■) transduced marrow cells.

RBC Expansion is Lineage-Restricted and Therapeutic After Minimal Lentiviral Transfer and Secondary Transplantation Background The coexpression of the therapeutic $\beta$-globin$^{AT87Q}$ and tEpoR induces RBC expansion in the context of elevated Epo plasma concentrations in $\beta$-thalassemia and results in an increased degree of phenotypic correction with a lower proportion of WBCs$^+$ in LG/HA-EpoRY1 versus LG mice. At <20% WBCs$^+$, virtually all LG/HA-EpoRY1 mice had a corrected phenotype (FIG. 6A). With 8.3% LG/HA-EpoRY1 WBCs$^+$, 81.6% of the RBCs originated from modified erythroid progenitors, whereas 10.4% LG WBCs$^+$ produced no more than 27% RBCs (FIG. 6B).

Figure 6B:
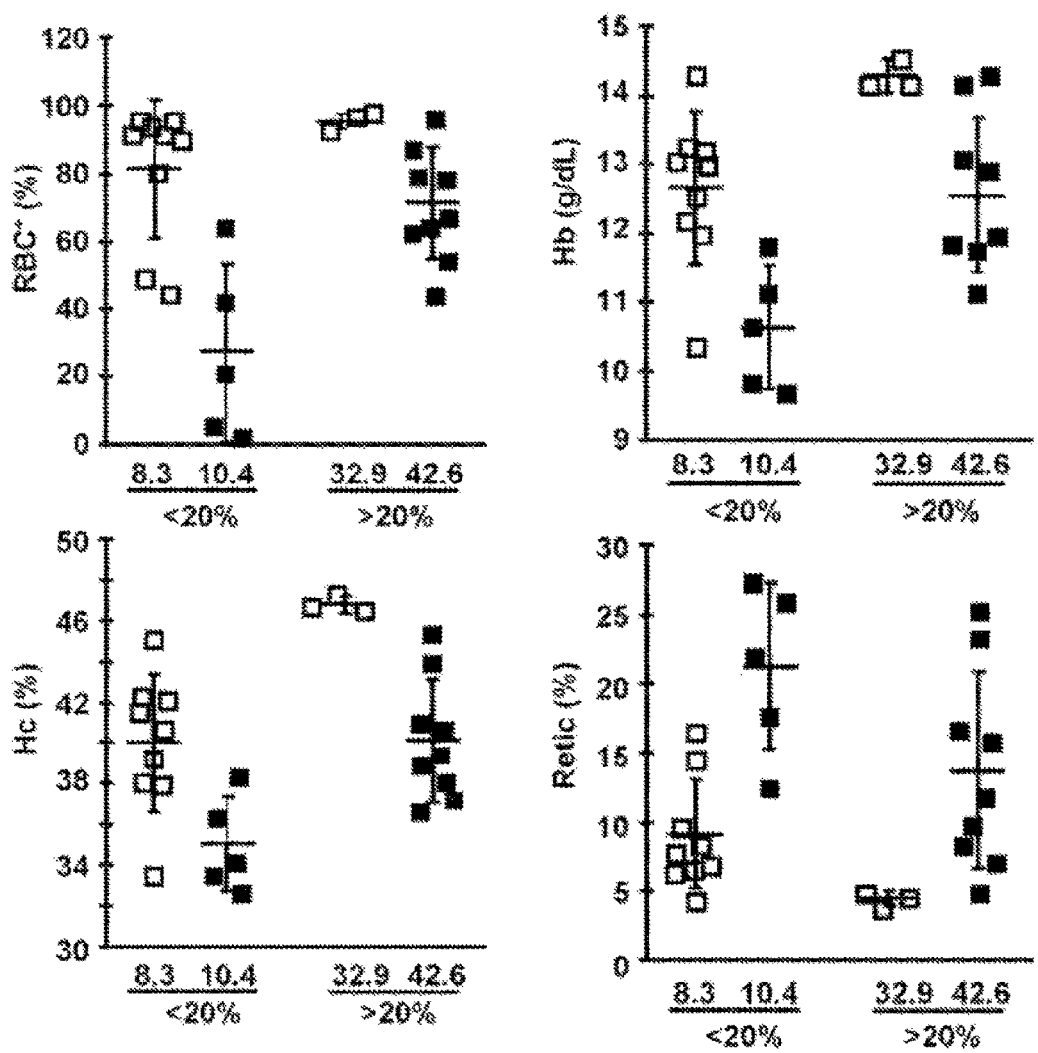

Consequently, with a mean WBC$^+$ proportion of 8.3%, the mean hematocrit value (40.1%) and hemoglobin concentration (12.7 g/dL) of LG/HA-EpoRY1 mice were much greater than in LG mice having an equivalent percentage (10.4%) of WBC$^+$ (FIG. 6B). Similar correction was obtained in LG mice (mean hematocrit value, 40.2%; hemoglobin concentration, 12.5 g/dL) but required a greater proportion of WBCs$^+$ (42.6%). The 4 mice of the LG/HA-EpoRY1 group with the lowest proportion of WBC$^+$ (3.3%±1.4%) had a mean human $\beta$-globin$^{AT87Q}$ level of 33.1%±5.6% distributed in 78.4%±20.1% RBCs, whereas among the 4 LG mice with the lowest proportion of modified WBCs (0.9%, 6.8%, 11.2%, and 13.3%), only the two mice having the highest proportion of WBCs$^+$ expressed detectable human ($\beta$-globin$^{AT87Q}$ (23.8% and 12.2%), and the percentages of modified RBCs were 1.0%, 6.0%, 42.3%, and 21.3%, respectively.

Secondary BM transplants were performed with HCs of primary transplanted mice 40 weeks after primary transplantation to assess whether repopulating HSC were depleted and to further decrease the proportion of modified HCs in a long-term study. Eleven lethally irradiated female mice received 5 million bone marrow cells from 3 primary mice undergoing mock transplantation, 4 LG primary recipients, and 4 LG/HA-EpoRY1 primary female mice. HCs of LG and LG/HA-EpoRY1 mice were diluted with cells from one of the mice transplanted with mock transduced cells to decrease the proportion of WBC$^+$ in the secondary animals that underwent transplantation (Table 5).

Results

The data showing increased amplification of erythroid cells modified with the LG/HA-EpoRY1 compared to the LG vector after secondary transplants is summarized in Table 5. Data are given for each secondary transplanted mouse with LG (group 2) and LG/HA-EpoRY1 (group 3)-modified cells 10 weeks after secondary transplantation. At 10 weeks after transplantation, the amplification factor F$^E$ ranged from 0 to 12 and 48 to 2374 for LG and LG/HA-Y1 mice, respectively. In LG and LG/HA-EpoRY1 groups indeed, the mean theoretical percentage of WBC was similar to the mean measured percentages of WBC.

TABLE 5

| Group | Primary | Dilution | WBC$^+$ (theo) | WBC$^+$ | RBC$^+$ | F$^E$ |
|---|---|---|---|---|---|---|
| 2 | 30.8 | 5 | 6.2 | 2.1 | 9.5 | 5 |
| 2 | 24.7 | 7 | 3.5 | 1.0 | 7.7 | 8 |
| 2 | 31.6 | 10 | 3.2 | 8.8 | 54.0 | 12 |
| 2 | 9.4 | 4 | 2.4 | 3.5 | 0.0 | 0 |
| Mean | | | 3.8 | 3.9 | | |
| SD | | | 1.7 | 3.5 | | |
| 3 | 1.8 | 1 | 1.7 | 0.1 | 70.4 | 2374 |
| 3 | 3.1 | 1 | 3.1 | 1.2 | 55.2 | 102 |
| 3 | 25.2 | 4 | 5.7 | 9.8 | 88.2 | 69 |
| 3 | 24.8 | 2 | 11.7 | 16.0 | 90.1 | 48 |
| Mean | | | 5.6 | 6.8 | | |
| SD | | | 4.4 | 7.5 | | |

Dilution indicates dilution factor with cells from a mouse transplanted with mock-transduced cells; F$^E$, amplification factor of modified erythroid cells vs. modified leukocytes; primary, the percentage of modified nucleated cells in BM of primary donors; RBC, percentage of RBCs containing human hemoglobin; WBC(theo), theoretical percentage of modified WBCs assuming 100% reconstitution with donor cells; WBC, percentage of modified WBCs in secondary transplants assuming 100% reconstitution with donor cells and deduced from copy numbers.

The vector copy numbers in WBCs were not statistically different between LG and LG/HA-Y1 mice (Table 6). However, the mean percentage of RBCs expressing human $\beta$-globin$^{AT87Q}$ and the blood concentration of $\beta$-globin$^{AT87Q}$ were greater in the presence of the LG/HA-EpoRY1 vector (26.1% human $\beta$-globin$^{AT87Q}$ distributed in 75.9% of erythrocytes) than with the LG vector (5.9% human $\beta$-globin$^{AT87Q}$ distributed in 17.8% erythrocytes). Calculations indicated that the difference was because of the expansion of the RBC$^+$ population in the case of the LG/HA-EpoRY1 vector, because the intracorpuscular RBC content in hybrid hemoglobin (made of human $\beta$-globin$^{AT87Q}$ and mouse $\beta$-globin) was similar for both LG/HA-EpoRY1 and the LG mouse groups (4.8 and 4.6 pg, respectively). Surprisingly, highly efficient correction of the anemia and other parameters was observed in $\beta$ thalassemic mice transplanted with LG/HA-EpoRY1 but not LG vectors (Table 6). Furthermore, it was equally unexpected that the secondary transplant experiments resulted in cell expansion that remained restricted to the erythroid lineage, even after extensive HC division.

TABLE 6

| Grp | Copy/WBC$^+$ Mean | SD | RBC$^+$ Mean | SD | h$\beta$-globin Mean | SD | Hb Mean | SD | Hc Mean | SD | RTC Mean | SD |
|---|---|---|---|---|---|---|---|---|---|---|---|---|
| 1 | 0.00 | 0.00 | 0.00 | 0.00 | 0.0 | 0.0 | 11.1 | 0.2 | 34.4 | 1.1 | 22.0 | 2.8 |
| 2 | 0.04 | 0.04 | 17.8 | 24.5 | 5.9 | 7.2 | 11.4 | .09 | 35.4 | 2.2 | 17.8 | 4.6 |
| 3 | 0.07 | 0.08 | 75.9 | 16.4 | 26.1 | 5.6 | 14.1 | 1.5 | 44.0 | 5.2 | 6.9 | 5.1 |
| P | 2.79 | | .001 | | <.001 | | .011 | | .011 | | .004 | |
| S$_{1-2}$ | | | N | | N | | N | | N | | N | |
| S$_{1-3}$ | | | Y | | Y | | Y | | Y | | Y | |

TABLE 6-continued

| $S_{2-3}$ | | Y | | Y | | Y | | Y | | Y | |
|---|---|---|---|---|---|---|---|---|---|---|---|
| | RBC | | MCV | | MCH | | MChuH | | sol Hb | | WBC |
| Grp | Mean | SD | Mean | SD | Mean | SD | Mean | SD | Mean | SD | Mean | SD |
| 1 | 9.3 | 0.2 | 37.0 | 1.8 | 11.9 | 0.4 | 0.0 | 0.0 | 9.2 | 0.4 | 7.4 | 1.1 |
| 2 | 9.4 | 0.2 | 37.6 | 1.8 | 12.1 | 0.8 | 4.6 | 0.9 | 9.9 | 1.1 | 8.6 | 2.7 |
| 3 | 10.1 | 1.0 | 43.4 | 1.5 | 139. | 0.4 | 4.8 | 0.5 | 13.2 | 1.9 | 8.4 | 1.0 |
| P | .207 | | .001 | | .003 | | .009 | | .008 | | .694 | |
| $S_{1-2}$ | | | N | | N | | Y | | Y | | | |
| $S_{1-3}$ | | | Y | | Y | | Y | | Y | | | |
| $S_{2-3}$ | | | Y | | Y | | N | | N | | | |

Mean hematological parameters and SDs in groups of secondary transplanted recipients with mock (1)-, LG (2)-, and LG/HA-Y1 (3)-modified cells 10 weeks after secondary transplantation. Copy indicates peripheral blood copy number per cell; RBC, RBC containing human hemoglobin (%); hu -glo, human β-globin (%); Hb, hemoglobin (g/dL); Hc, hematocrit value (%); RTC, reticulocytes (%); RBC, red blood cells (1012/L); MCV, mean corpuscular volume (fL); MCH, mean corpuscular hemoglobin (pg); MChuH, mean corpuscular human hemoglobin in modified RBC (pg); sol Hb, soluble hemoglobin (g/dL); WBC, white blood cells (109/L). Multiple and pairwise comparisons are made by the use of one-way analysis of variance and the Holm-Sidak method, respectively. When an overall significance level <.05 (P value) is obtained, statistical significance is given as yes (Y) or no (N) between groups 1 and 2 (S1-2), 1 and 3 (S1-3), and 2 and 3 (S2-3).

Example 7

Erythroid Cell Expansion is Self-Controlled

Background

The various hematopoietic lineages were analyzed by flow cytometry with lineage specific antibodies in the peripheral blood and BM of β thalassemic mice that underwent transplantation with cells transduced with LG and LG/HA-EpoRY1 vectors.

Results

The mean percentages of T-lymphoid, B-lymphoid, and myeloid cells among CD45.2-positive cells were not statistically different between LG and LG/HA-EpoRY1 mice that underwent transplantation (FIG. 7A). The plasma Epo concentration and the number of $RBC^+$ were inversely correlated, independently of the presence or absence of tEpoR (FIG. 7B), indicating that the presence of tEpoR did not impair the control of modified erythroid cell production by plasma Epo.

No correlation was observed between the percentage of $RBC^+$ and WBC or platelets (not shown) counts, nor was a significant difference observed in WBC (P=0.125) and platelet (P=0.254) counts between the two groups of mice (FIG. 7C). Histologic sections of spleen, liver, lung, kidney, heart, BM, and thymus of mice were analyzed 10 months after transplantation. No neoplastic cell infiltration was observed.

To investigate possible effects of vector integration on cell proliferation, insertion site analysis was performed on cells from four β thalassemic mice that underwent transplantation five months earlier with cells transduced by the LG/HA-EpoRY1 vector. Mice underwent transplantation with a relatively low number of HSCs after conditioning with low-dose irradiation (200 rads) to maximize the pressure for cell proliferation and thereby maximize the chances of detecting effects of insertional activation of genes promoting cell proliferation or survival. At 5 months after transplantation, the lymphomyeloid (CD45$^+$) and erythroid (CD45$^-$) cells of each mouse were sorted, genomic DNA was extracted, and integration site sequences were determined.

Integration sites were analyzed with the use of Mu-mediated transposition in vitro. Because the purified Mu transposase protein has minimal target sequence specificity, recovery of integration sites is much less biased than with standard methods involving genomic DNA cleavage with restriction enzymes. An added advantage is that the number of independent Mu transposition events associated with each integration site provides an estimate of the proportion of that cell clone in the original sample.

A total of 2510 sequence reads were generated with 454/Roche pyrosequencing. Sites were recovered from a total of 1070 independent Mu transposition events, including 47 unique integration sites, paralleling the low number of cells inoculated initially. Comparison of the integration site distributions in the lymphoidmyeloid and erythroid cell samples showed various degrees of commonality between lineages among the mice (FIG. 11), possibly as a result of stochastic effects of sampling low numbers.

Analysis of the insertional events indicated that use of the LG/Ha-EpoRY1 vector is a safe therapeutic modality and that growth of the modified erythroid cells was not due to integration near genes involved in cell growth or proliferation promoted outgrowth of particular cell clones. No interactions between EpoR signaling and insertional activation of proto-oncogenes, resulting in clonal expansion were observed. There were no examples of an enrichment of integration sites near a single gene associated with cell growth. In addition, the distribution of the most abundant cell clones (marked by integration sites) relative to a list of cancer-related genes (the allOnco database) was analyzed and no association between clonal abundance and proximity to cancer-related genes was found (FIG. 8A-B).

The proportion of integration sites within 50 kb of an oncogene in LG/HA-EpoRY1 cells was compared to the proportion of insertion site (IS) identified in murine HCs modified by the LG vector, before and 9 months after transplantation in β thalassemic mice, and described in a previous study (Ronen et al, *Mol Ther*, published online Mar. 8, 2011). No statistically significant differences between sets were found by the Fisher exact test for proximity to cancer-related genes (FIG. 8C).

Further. No biases in integration relative to other types of genomic features could be detected when sites from the LG/HA-EpoRY1-treated cells were compared with sites from the LG transduced cells. No form of genomic annotation showed strong differences in insertion site between the 2 vectors.

Thus, these data do not support the idea that integration near genes involved in cell growth or proliferation promoted outgrowth of particular cell clones.

The various embodiments described above can be combined to provide further embodiments. All of the U.S. patents, U.S. patent application publications, U.S.

patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A vector comprising:
   a) a left (5') retroviral LTR;
   b) a first hematopoietic cell expression control sequence that comprises a first erythroid cell specific promoter, operably linked to a globin gene;
   c) a second hematopoietic cell expression control sequence that comprises a second erythroid cell specific promoter operably linked to a truncated erythropoietin receptor (tEpoR), wherein the tEpoR comprises a C-terminal truncation that reduces the turnover of the tEpoR compared to an endogenous erythropoietin receptor (EpoR) or that increases the half-life of the tEpoR compared to an endogenous erythropoietin receptor (EpoR); and
   d) a right (3') retroviral LTR.

2. The vector of claim 1, wherein the first hematopoietic cell expression control sequence is selected from the group consisting of: a human β-globin promoter; a human β-globin LCR; and a human α-globin HS40 enhancer and an ankyrin-1 promoter.

3. The vector of claim 1, wherein the second hematopoietic cell expression control sequence is selected from the group consisting of: a human β-globin promoter; a human β-globin LCR; and a human α-globin HS40 enhancer and an ankyrin-1 promoter.

4. The vector of claim 1, wherein the first hematopoietic cell expression control sequence comprises a human β-globin promoter and a human β-globin LCR.

5. The vector of claim 1, wherein the second hematopoietic cell expression control sequence comprises a human α-globin HS40 enhancer and an ankyrin-1 promoter.

6. The vector of claim 1, wherein the first hematopoietic cell expression control sequence comprises a human β-globin promoter and a human β-globin LCR and the second hematopoietic cell expression control sequence comprises a human α-globin HS40 enhancer and an ankyrin-1 promoter.

7. The vector of claim 1, wherein the globin gene is selected from the group consisting of: human β-globin, human δ-globin, and human γ-globin.

8. The vector of claim 1, wherein the globin gene is selected from the group consisting of: a human $β^A$-globin gene encoding a threonine to glutamine mutation at codon 87 ($β^{AT87Q}$) or a human $β^A$-globin gene.

9. The vector of claim 1, wherein the tEpoR comprises (a) a C-terminal truncation of 80 to 90 amino acids; (b) a C-terminal truncation of 85 to 95 amino acids; or (c) a C-terminal truncation of about 83, or about 91 amino acids.

10. The vector of claim 1, wherein: (a) the vector is a lentivirus vector; (b) the 5' LTR or 3' LTR is a lentivirus LTR; (c) the 5' LTR and 3' LTR are lentivirus LTRs; (d) the promoter of the 5' LTR is replaced with a heterologous promoter; (e) the 3' LTR comprises one or more modifications; (f) the 3' LTR comprises one or more deletions; or (g) the 3' LTR is a self-inactivating (SIN) LTR.

11. The vector of claim 1, further comprising one or more of a Psi packaging sequence ($ψ^+$), a central polypurine tract/DNA flap (cPPT/FLAP), a retroviral export element, a posttranscriptional regulatory element, an insulator element, a polyadenylation sequence, a selectable marker, and a cell suicide gene.

12. A composition comprising a pharmaceutically acceptable carrier and the vector of claim 1.

13. A human cell comprising the vector of claim 1.

14. The cell of claim 13, wherein: (a) the cell is selected from the group consisting of: an embryonic stem cell, an adult stem cell, an adult progenitor cell, and a differentiated adult cell; (b) the cell is a hematopoietic stem cell or a hematopoietic progenitor cell; (c) the cell is a hematopoietic stem cell or a hematopoietic progenitor cell and the source of the stem or progenitor cell is bone marrow, cord blood, placental blood, or peripheral blood; or (d) the cell is transduced with the vector.

15. A composition comprising a pharmaceutically acceptable carrier and the cell of claim 13.

16. A composition comprising a pharmaceutically acceptable carrier and the cell of claim 14.

* * * * *

SEQUENCE LISTING

```
<160> NUMBER OF SEQ ID NOS: 38

<210> SEQ ID NO 1
<211> LENGTH: 576
<212> TYPE: DNA
<213> ORGANISM: Homo sapiens

<400> SEQUENCE: 1
actcttctgg tccccacaga ctcagagaga acccaccatg gtgctgtctc ctgccgacaa      60
gaccaacgtc aaggccgcct ggggtaaggt cggcgcgcac gctggcgagt atggtgcgga     120
ggccctggag aggatgttcc tgtccttccc caccaccaag acctacttcc cgcacttcga     180
cctgagccac ggctctgccc aggttaaggg ccacggcaag aaggtggccg acgcgctgac     240
caacgccgtg gcgcacgtgg acgacatgcc caacgcgctg tccgccctga cgacctgca     300 cgcgcacaag cttcgggtgg acccggtcaa cttcaagctc ctaagccact gcctgctggt     360
gaccctggcc gcccacctcc ccgccgagtt caccctgcg gtgcacgcct ccctggacaa     420
gttcctggct tctgtgagca ccgtgctgac ctccaaatac cgttaagctg gagcctcggt     480
ggccatgctt cttgcccctt gggcctcccc ccagcccctc ctcccttcc tgcacccgta     540 ccccgtggt ctttgaataa agtctgagtg ggcggc                               576

<210> SEQ ID NO 2
<211> LENGTH: 142
<212> TYPE: PRT
<213> ORGANISM: Homo sapiens

<400> SEQUENCE: 2

Met Val Leu Ser Pro Ala Asp Lys Thr Asn Val Lys Ala Ala Trp Gly
1               5                   10                  15

Lys Val Gly Ala His Ala Gly Glu Tyr Gly Ala Glu Ala Leu Glu Arg
                20                  25                  30

Met Phe Leu Ser Phe Pro Thr Thr Lys Thr Tyr Phe Pro His Phe Asp
            35                  40                  45

Leu Ser His Gly Ser Ala Gln Val Lys Gly His Gly Lys Lys Val Ala
        50                  55                  60

Asp Ala Leu Thr Asn Ala Val Ala His Val Asp Asp Met Pro Asn Ala
65                  70                  75                  80

Leu Ser Ala Leu Ser Asp Leu His Ala His Lys Leu Arg Val Asp Pro
                85                  90                  95

Val Asn Phe Lys Leu Leu Ser His Cys Leu Leu Val Thr Leu Ala Ala
                100                 105                 110

His Leu Pro Ala Glu Phe Thr Pro Ala Val His Ala Ser Leu Asp Lys
            115                 120                 125

Phe Leu Ala Ser Val Ser Thr Val Leu Thr Ser Lys Tyr Arg
        130                 135                 140

<210> SEQ ID NO 3
```

<211> LENGTH: 142
<212> TYPE: PRT
<213> ORGANISM: Mus musculus

<400> SEQUENCE: 3

```
Met Val Leu Ser Gly Glu Asp Lys Ser Asn Ile Lys Ala Ala Trp Gly
1               5                   10                  15
Lys Ile Gly Gly His Gly Ala Glu Tyr Gly Ala Glu Ala Leu Glu Arg
                20                  25                  30
Met Phe Ala Ser Phe Pro Thr Thr Lys Thr Tyr Phe Pro His Phe Asp
            35                  40                  45
Val Ser His Gly Ser Ala Gln Val Lys Gly His Gly Lys Lys Val Ala
        50                  55                  60
Asp Ala Leu Ala Asn Ala Ala Gly His Leu Asp Asp Leu Pro Gly Ala
65                  70                  75                  80
Leu Ser Ala Leu Ser Asp Leu His Ala His Lys Leu Arg Val Asp Pro
                85                  90                  95
Val Asn Phe Lys Leu Leu Ser His Cys Leu Leu Val Thr Leu Ala Ser
                100                 105                 110
His His Pro Ala Asp Phe Thr Pro Ala Val His Ala Ser Leu Asp Lys
            115                 120                 125
Phe Leu Ala Ser Val Ser Thr Val Leu Thr Ser Lys Tyr Arg
        130                 135                 140
```

<210> SEQ ID NO 4
<211> LENGTH: 142
<212> TYPE: PRT
<213> ORGANISM: Rattus norvegicus

<400> SEQUENCE: 4

```
Met Val Leu Ser Ala Asp Asp Lys Thr Asn Ile Lys Asn Cys Trp Gly
1               5                   10                  15
Lys Ile Gly Gly His Gly Gly Glu Tyr Gly Glu Glu Ala Leu Gln Arg
                20                  25                  30
Met Phe Ala Ala Phe Pro Thr Thr Lys Thr Tyr Phe Ser His Ile Asp
            35                  40                  45
Val Ser Pro Gly Ser Ala Gln Val Lys Ala His Gly Lys Lys Val Ala
        50                  55                  60
Asp Ala Leu Ala Lys Ala Ala Asp His Val Glu Asp Leu Pro Gly Ala
65                  70                  75                  80
Leu Ser Thr Leu Ser Asp Leu His Ala His Lys Leu Arg Val Asp Pro
                85                  90                  95
Val Asn Phe Lys Phe Leu Ser His Cys Leu Leu Val Thr Leu Ala Cys
                100                 105                 110
His His Pro Gly Asp Phe Thr Pro Ala Met His Ala Ser Leu Asp Lys
            115                 120                 125
Phe Leu Ala Ser Val Ser Thr Val Leu Thr Ser Lys Tyr Arg
        130                 135                 140
```

<210> SEQ ID NO 5
<211> LENGTH: 626
<212> TYPE: DNA
<213> ORGANISM: Homo sapiens

<400> SEQUENCE: 5

```
acatttgctt ctgacacaac tgtgttcact agcaacctca aacagacacc atggtgcatc    60
tgactcctga ggagaagtct gccgttactg ccctgtgggg caaggtgaac gtggatgaag   120
```

-continued

```
ttggtggtga ggccctgggc aggctgctgg tggtctaccc ttggacccag aggttctttg      180
agtcctttgg ggatctgtcc actcctgatg ctgttatggg caaccctaag gtgaaggctc      240
atggcaagaa agtgctcggt gcctttagtg atggcctggc tcacctggac aacctcaagg      300
gcacctttgc cacactgagt gagctgcact gtgacaagct gcacgtggat cctgagaact      360
tcaggctcct gggcaacgtg ctggtctgtg tgctggccca tcactttggc aaagaattca      420
ccccaccagt gcaggctgcc tatcagaaag tggtggctgg tgtggctaat gccctggccc      480
acaagtatca ctaagctcgc tttcttgctg tccaatttct attaaaggtt cctttgttcc      540
ctaagtccaa ctactaaact ggggatatt atgaagggcc ttgagcatct ggattctgcc      600
taataaaaaa catttatttt cattgc                                           626
```

<210> SEQ ID NO 6
<211> LENGTH: 147
<212> TYPE: PRT
<213> ORGANISM: Homo sapiens

<400> SEQUENCE: 6

```
Met Val His Leu Thr Pro Glu Glu Lys Ser Ala Val Thr Ala Leu Trp
1               5                   10                  15

Gly Lys Val Asn Val Asp Glu Val Gly Gly Glu Ala Leu Gly Arg Leu
            20                  25                  30

Leu Val Val Tyr Pro Trp Thr Gln Arg Phe Phe Glu Ser Phe Gly Asp
        35                  40                  45

Leu Ser Thr Pro Asp Ala Val Met Gly Asn Pro Lys Val Lys Ala His
    50                  55                  60

Gly Lys Lys Val Leu Gly Ala Phe Ser Asp Gly Leu Ala His Leu Asp
65                  70                  75                  80

Asn Leu Lys Gly Thr Phe Ala Thr Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala His
    130                 135                 140

Lys Tyr His
145
```

<210> SEQ ID NO 7
<211> LENGTH: 147
<212> TYPE: PRT
<213> ORGANISM: Homo sapiens

<400> SEQUENCE: 7

```
Met Val His Leu Thr Pro Glu Glu Lys Ser Ala Val Thr Ala Leu Trp
1               5                   10                  15

Gly Lys Val Asn Val Asp Glu Val Gly Gly Glu Ala Leu Gly Arg Leu
            20                  25                  30

Leu Val Val Tyr Pro Trp Thr Gln Arg Phe Phe Glu Ser Phe Gly Asp
        35                  40                  45

Leu Ser Thr Pro Asp Ala Val Met Gly Asn Pro Lys Val Lys Ala His
    50                  55                  60

Gly Lys Lys Val Leu Gly Ala Phe Ser Asp Gly Leu Ala His Leu Asp
65                  70                  75                  80
```

```
Asn Leu Lys Gly Thr Phe Ala Gln Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala His
    130                 135                 140

Lys Tyr His
145

<210> SEQ ID NO 8
<211> LENGTH: 147
<212> TYPE: PRT
<213> ORGANISM: Mus musculus

<400> SEQUENCE: 8

Met Val His Leu Thr Asp Ala Glu Lys Ala Ala Val Ser Gly Leu Trp
1               5                   10                  15

Gly Lys Val Asn Ala Asp Glu Val Gly Gly Glu Ala Leu Gly Arg Leu
            20                  25                  30

Leu Val Val Tyr Pro Trp Thr Gln Arg Tyr Phe Asp Ser Phe Gly Asp
        35                  40                  45

Leu Ser Ser Ala Ser Ala Ile Met Gly Asn Ala Lys Val Lys Ala His
    50                  55                  60

Gly Lys Lys Val Ile Thr Ala Phe Asn Asp Gly Leu Asn His Leu Asp
65                  70                  75                  80

Ser Leu Lys Gly Thr Phe Ala Ser Leu Ser Glu Leu His Cys Asp Lys
                85                  90                  95

Leu His Val Asp Pro Glu Asn Phe Arg Leu Leu Gly Asn Met Ile Val
            100                 105                 110

Ile Val Leu Gly His His Leu Gly Lys Asp Phe Thr Pro Ala Ala Gln
        115                 120                 125

Ala Ala Phe Gln Lys Val Val Ala Gly Val Ala Ala Ala Leu Ala His
    130                 135                 140

Lys Tyr His
145

<210> SEQ ID NO 9
<211> LENGTH: 147
<212> TYPE: PRT
<213> ORGANISM: Rattus norvegicus

<400> SEQUENCE: 9

Met Val His Leu Thr Asp Ala Glu Lys Ala Ala Val Asn Gly Leu Trp
1               5                   10                  15

Gly Lys Val Asn Pro Asp Asp Val Gly Gly Glu Ala Leu Gly Arg Leu
            20                  25                  30

Leu Val Val Tyr Pro Trp Thr Gln Arg Tyr Phe Asp Ser Phe Gly Asp
        35                  40                  45

Leu Ser Ser Ala Ser Ala Ile Met Gly Asn Pro Lys Val Lys Ala His
    50                  55                  60

Gly Lys Lys Val Ile Asn Ala Phe Asn Asp Gly Leu Lys His Leu Asp
65                  70                  75                  80

Asn Leu Lys Gly Thr Phe Ala His Leu Ser Glu Leu His Cys Asp Lys
                85                  90                  95
```

```
Leu His Val Asp Pro Glu Asn Phe Arg Leu Leu Gly Asn Met Ile Val
            100                 105                 110

Ile Val Leu Gly His His Leu Gly Lys Glu Phe Thr Pro Cys Ala Gln
        115                 120                 125

Ala Ala Phe Gln Lys Val Val Ala Gly Val Ala Ser Ala Leu Ala His
    130                 135                 140

Lys Tyr His
145

<210> SEQ ID NO 10
<211> LENGTH: 583
<212> TYPE: DNA
<213> ORGANISM: Homo sapiens

<400> SEQUENCE: 10
acactcgctt ctggaacgtc tgaggttatc aataagctcc tagtccagac gccatgggtc      60
atttcacaga ggaggacaag gctactatca caagcctgtg gggcaaggtg aatgtggaag    120
atgctggagg agaaaccctg gaaggctcc tggttgtcta cccatggacc cagaggttct     180
ttgacagctt tggcaacctg tcctctgcct ctgccatcat gggcaacccc aaagtcaagg    240
cacatggcaa gaaggtgctg acttccttgg agatgccat aaagcacctg gatgatctca     300
agggcacctt tgcccagctg agtgaactgc actgtgacaa gctgcatgtg atcctgaga    360 acttcaagct cctgggaaat gtgctggtga ccgttttggc aatccatttc ggcaaagaat    420 tcaccctga ggtgcaggct tcctggcaga gatggtgac tggagtggcc agtgccctgt     480
cctccagata ccactgagct cactgcccat gatgcagagc tttcaaggat aggctttatt    540
ctgcaagcaa tcaaataata aatctattct gctaagagat cac                      583

<210> SEQ ID NO 11
<211> LENGTH: 147
<212> TYPE: PRT
<213> ORGANISM: Homo sapiens

<400> SEQUENCE: 11

Met Gly His Phe Thr Glu Glu Asp Lys Ala Thr Ile Thr Ser Leu Trp
1               5                   10                  15

Gly Lys Val Asn Val Glu Asp Ala Gly Gly Glu Thr Leu Gly Arg Leu
            20                  25                  30

Leu Val Val Tyr Pro Trp Thr Gln Arg Phe Phe Asp Ser Phe Gly Asn
        35                  40                  45

Leu Ser Ser Ala Ser Ala Ile Met Gly Asn Pro Lys Val Lys Ala His
    50                  55                  60

Gly Lys Lys Val Leu Thr Ser Leu Gly Asp Ala Ile Lys His Leu Asp
65                  70                  75                  80

Asp Leu Lys Gly Thr Phe Ala Gln Leu Ser Glu Leu His Cys Asp Lys
                85                  90                  95

Leu His Val Asp Pro Glu Asn Phe Lys Leu Leu Gly Asn Val Leu Val
            100                 105                 110

Thr Val Leu Ala Ile His Phe Gly Lys Glu Phe Thr Pro Glu Val Gln
        115                 120                 125

Ala Ser Trp Gln Lys Met Val Thr Gly Val Ala Ser Ala Leu Ser Ser
    130                 135                 140

Arg Tyr His
145
```

<210> SEQ ID NO 12
<211> LENGTH: 147
<212> TYPE: PRT
<213> ORGANISM: Mus musculus

<400> SEQUENCE: 12

```
Met Val His Phe Thr Ala Glu Glu Lys Ala Ala Ile Thr Ser Ile Trp
1               5                   10                  15

Asp Lys Val Asp Leu Glu Lys Val Gly Gly Glu Thr Leu Gly Arg Leu
            20                  25                  30

Leu Ile Val Tyr Pro Trp Thr Gln Arg Phe Phe Asp Lys Phe Gly Asn
        35                  40                  45

Leu Ser Ser Ala Leu Ala Ile Met Gly Asn Pro Arg Ile Arg Ala His
    50                  55                  60

Gly Lys Lys Val Leu Thr Ser Leu Gly Leu Gly Val Lys Asn Met Asp
65                  70                  75                  80

Asn Leu Lys Glu Thr Phe Ala His Leu Ser Glu Leu His Cys Asp Lys
                85                  90                  95

Leu His Val Asp Pro Glu Asn Phe Lys Leu Leu Gly Asn Met Leu Val
            100                 105                 110

Ile Val Leu Ser Thr His Phe Ala Lys Glu Phe Thr Pro Glu Val Gln
        115                 120                 125

Ala Ala Trp Gln Lys Leu Val Ile Gly Val Ala Asn Ala Leu Ser His
    130                 135                 140

Lys Tyr His
145
```

<210> SEQ ID NO 13
<211> LENGTH: 147
<212> TYPE: PRT
<213> ORGANISM: Rattus norvegicus

<400> SEQUENCE: 13

```
Met Val His Phe Thr Ala Glu Glu Lys Ala Ala Ile Ile Ser Ile Trp
1               5                   10                  15

Glu Lys Val Asp Leu Glu Lys Ile Gly Gly Glu Thr Leu Gly Arg Leu
            20                  25                  30

Leu Ile Val Tyr Pro Trp Thr Gln Arg Phe Phe Asp Lys Phe Gly Asn
        35                  40                  45

Leu Ser Ser Ala Leu Ala Ile Met Gly Asn Pro Arg Ile Arg Ala His
    50                  55                  60

Gly Lys Lys Val Leu Thr Ser Leu Gly Ser Ala Val Glu Asn Met Asp
65                  70                  75                  80

Asn Leu Lys Glu Thr Phe Ala His Leu Ser Glu Leu His Cys Asp Lys
                85                  90                  95

Leu His Val Asp Pro Gln Asn Phe Lys Leu Leu Gly Asn Met Leu Val
            100                 105                 110

Ile Val Leu Ser Thr His Phe Ala Lys Glu Phe Thr Pro Glu Val Gln
        115                 120                 125

Ala Ala Trp Gln Lys Leu Val Met Gly Val Ala Asn Ala Leu Ser His
    130                 135                 140

Lys Tyr His
145
```

<210> SEQ ID NO 14
<211> LENGTH: 774

<212> TYPE: DNA
<213> ORGANISM: Homo sapiens

<400> SEQUENCE: 14

```
agggcaagtt aagggaatag tggaatgaag gttcattttt cattctcaca aactaatgaa      60
accctgctta tcttaaacca acctgctcac tggagcaggg aggacaggac cagcataaaa     120
ggcagggcag agtcgactgt tgcttacact ttcttctgac ataacagtgt tcactagcaa     180
cctcaaacag acaccatggt gcatctgact cctgaggaga agactgctgt caatgccctg     240
tggggcaaag tgaacgtgga tgcagttggt ggtgaggccc tgggcagatt actggtggtc     300
taccttgga cccagaggtt ctttgagtcc tttggggatc tgtcctctcc tgatgctgtt     360
atgggcaacc ctaaggtgaa ggctcatggc aagaaggtgc taggtgcctt tagtgatggc     420
ctggctcacc tggacaacct caagggcact ttttctcagc tgagtgagct gcactgtgac     480
aagctgcacg tggatcctga gaacttcagg ctcttgggca atgtgctggt gtgtgtgctg     540
gcccgcaact tggcaagga attcaccccca caaatgcagg ctgcctatca gaaggtggtg     600
gctggtgtgg ctaatgccct ggctcacaag taccattgag atcctggact gtttcctgat     660
aaccataaga agaccctatt tccctagatt ctattttctg aacttgggaa cacaatgcct     720
acttcaaggg tatggcttct gcctaataaa gaatgttcag ctcaacttcc tgat          774
```

<210> SEQ ID NO 15
<211> LENGTH: 147
<212> TYPE: PRT
<213> ORGANISM: Homo sapiens

<400> SEQUENCE: 15

```
Met Val His Leu Thr Pro Glu Glu Lys Thr Ala Val Asn Ala Leu Trp
1               5                   10                  15

Gly Lys Val Asn Val Asp Ala Val Gly Gly Glu Ala Leu Gly Arg Leu
            20                  25                  30

Leu Val Val Tyr Pro Trp Thr Gln Arg Phe Phe Glu Ser Phe Gly Asp
        35                  40                  45

Leu Ser Ser Pro Asp Ala Val Met Gly Asn Pro Lys Val Lys Ala His
    50                  55                  60

Gly Lys Lys Val Leu Gly Ala Phe Ser Asp Gly Leu Ala His Leu Asp
65                  70                  75                  80

Asn Leu Lys Gly Thr Phe Ser Gln Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala Arg Asn Phe Gly Lys Glu Phe Thr Pro Gln Met Gln
        115                 120                 125

Ala Ala Tyr Gln Lys Val Val Ala Gly Val Ala Asn Ala Leu Ala His
    130                 135                 140

Lys Tyr His
145
```

<210> SEQ ID NO 16
<211> LENGTH: 2459
<212> TYPE: DNA
<213> ORGANISM: Homo sapiens

<400> SEQUENCE: 16

```
cttagaggcg cctggtcggg aagggcctgg tcagctgcgt ccggcggagg cagctgctga      60
```

```
cccagctgtg gactgtgccg ggggcggggg acggaggggc aggagccctg ggctccccgt      120
ggcgggggct gtatcatgga ccacctcggg gcgtccctct ggcccaggt cggctccctt       180 tgtctcctgc tcgctggggc cgcctgggcg ccccgccta acctcccgga ccccaagttc       240
gagagcaaag cggccttgct ggcggccgg gggcccgaag agcttctgtg cttcaccgag        300
cggttggagg acttggtgtg tttctgggag gaagcggcga gcgctggggt gggcccgggc      360
aactacagct tctcctacca gctcgaggat gagccatgga agctgtgtcg cctgcaccag      420
gctcccacgg ctcgtggtgc ggtgcgcttc tggtgttcgc tgcctacagc cgacacgtcg      480
agcttcgtgc ccctagagtt gcgcgtcaca gcagcctccg gcgctccgcg atatcaccgt      540
gtcatccaca tcaatgaagt agtgctccta gacgccccg tggggctggt ggcgcggttg       600
gctgacgaga gcggccacgt agtgttcgc tggctcccgc cgcctgagac acccatgacg       660
tctcacatcc gctacgaggt ggacgtctcg gccggcaacg gcgcagggag cgtacagagg      720
gtggagatcc tggagggccg caccgagtgt gtgctgagca acctgcgggg ccggacgcgc      780
tacaccttcg ccgtccgcgc gcgtatggct gagccgagct tcgcggcttt ctggagcgcc      840
tggtcggagc ctgtgtcgct gctgacgcct agcgacctgg accccctcat cctgacgctc      900
tccctcatcc tcgtggtcat cctggtgctg ctgaccgtgc tcgcgctgct ctcccaccgc      960
cgggctctga agcagaagat ctggcctggc atcccgagcc cagagagcga gtttgaaggc     1020
ctcttcacca cccacaaggg taacttccag ctgtggctgt accagaatga tggctgcctg     1080
tggtggagcc cctgcacccc cttcacggag gacccacctg cttccctgga agtcctctca     1140
gagcgctgct gggggacgat gcaggcagtg gagccgggga cagatgatga gggccccctg     1200
ctggagccag tgggcagtga gcatgcccag gatacctatc tggtgctgga caaatggttg     1260
ctgccccgga acccgcccag tgaggacctc ccagggcctg gtggcagtgt ggacatagtg     1320
gccatggatg aaggctcaga agcatcctcc tgctcatctg ctttggcctc gaagcccagc     1380
ccagagggag cctctgctgc cagctttgag tacactatcc tggacccag ctcccagctc      1440 ttgcgtccat ggacactgtg ccctgagctg ccccctaccc cacccaccct aaagtacctg     1500
taccttgtgg tatctgactc tggcatctca actgactaca gctcagggga ctcccaggga     1560
gcccaagggg gcttatccga tggcccctac tccaacccct tatgagaacag ccttatccca     1620 gccgctgagc ctctgccccc cagctatgtg gcttgctctt aggacaccag gctgcagatg     1680
atcagggatc caatatgact cagagaacca gtgcagactc aagacttatg gaacagggat     1740
ggcgaggcct ctctcaggag caggggcatt gctgattttg tctgcccaat ccatcctgct     1800
caggaaacca caaccttgca gtattttaa atatgtatag tttttttttg tatctatata      1860
tatatataca catatgtatg taagttttc taccatgatt tctacaaaca cccttaagt       1920 cccatcttcc cctgggcata ggccatagg atagaagtta aagttcttga gcttattcag      1980
aagctggatc tgcaatctga atgctactca aacataaca aaatagtatg ttaaacagct      2040
cttaaatctt actggcttac cacattaaat gatttctctc tcctaactca gctcaaatgg     2100
gcagccatcc atgggatgag tcagaggttc agactcttcc agtctgtagc tctaccttct     2160
cttagggtac ttagatggat cccctgttct acaaactgcc agtcagcaag ggaagaaaaa     2220
gggcagcaat gaccctcaat gggccatttg agggatctgg cctggaaatg gcttcctct      2280 cttcttctca cacctcactg gctggaaaca gtcacatgac cccagtcaca tgaaaggcca     2340
ggaaacttag tttagctgta cacccaggaa gggcaaagct gtttaagggc cactagctag     2400
tctctgccac taataataat aaagtaatt ctgaatcagg caaaaaaaaa aaaaaaaa       2459
```

<210> SEQ ID NO 17
<211> LENGTH: 1829
<212> TYPE: DNA
<213> ORGANISM: Mus musculus

<400> SEQUENCE: 17

| | | | | | |
|---|---|---|---|---|---|
| agaagctcct | ggtcagctgt | gtccggcagc | tgctgctgac | ccagctgtgg | actagggga    60 |
| aggggaaaga | ggaaagggaa | ggagaggtgg | ggggacgaa  | acaggggcgc | tggagccctg  120 |
| agcttcctga | agctagggct | gcatcatgga | caaactcagg | gtgcccctct | ggcctcgggt  180 |
| aggcccctc  | tgtctcctac | ttgctggggc | agcctgggca | ccttcaccca | gcctcccgga  240 |
| ccccaagttt | gagagcaaag | cggccctgct | ggcatcccgg | ggctccgaag | aacttctgtg  300 |
| cttcacccaa | cgcttggaag | acttggtgtg | tttctgggag | gaagcggcga | gctccgggat  360 |
| ggacttcaac | tacagcttct | cataccagct | cgagggtgag | tcacgaaagt | catgtagcct  420 |
| gcaccaggct | cccaccgtcc | gcggctccgt | gcgtttctgg | tgttcactgc | aacagcgga   480 |
| cacatcgagt | tttgtgccgc | tggagctgca | ggtgacggag | gcgtccggtt | ctcctcgcta  540 |
| tcaccgcatc | atccatatca | atgaagtagt | gctcctggac | gccccgcgg  | ggctgctggc  600 |
| gcgccgggca | gaagagggca | gccacgtggt | gctgcgctgg | ctgccacctc | ctggagcacc  660 |
| tatgaccacc | cacatccgat | atgaagtgga | cgtgtcggca | ggcaaccggg | caggagggac  720 |
| acaaagggtg | gaggtcctgg | aaggccgcac | tgagtgtgtt | ctgagcaacc | tgcggggcgg  780 |
| gacgcgctac | accttcgctg | ttcgagcgcg | catggccgag | ccgagcttca | gcggattctg  840 |
| gagtgcctgg | tctgagcccg | cgtcactact | gaccgctagc | gacctggacc | ctctcatctt  900 |
| gacgctgtct | ctcattctgg | tcctcatctc | gctgttgctg | acggttctgg | ccctgctgtc  960 |
| ccaccgccgg | actctgcagc | agaagatctg | gcctggcatc | ccaagcccag | agagcgagtt 1020 |
| tgagggtctc | ttcaccaccc | acaagggtaa | cttccagctg | tggctgctgc | agcgtgatgg 1080 |
| ttgtctgtgg | tggagcccgg | gcagctcctt | ccctgaggat | ccacctgccc | acctagaggt 1140 |
| cctctcagag | ccacgctggg | cagtgactca | ggctggggac | ccaggggcag | atgatgaggg 1200 |
| gccctactg  | gagccggtgg | gcagtgagca | tgccaggac  | acctacttgg | tattggataa 1260 |
| gtggttgctg | ccccggaccc | catgcagtga | gaacctctca | gggcctgggg | gcagtgtgga 1320 |
| ccctgtgact | atggatgaag | cttcagaaac | atcttcctgc | ccgtctgact | tggcctcaaa 1380 |
| gcccaggcca | gagggcacct | caccttccag | ctttgagtac | accatcctgg | accccagctc 1440 |
| tcagctcctg | tgccctcggg | cactgcctcc | gagctacct  | cccactccac | ctcacttgaa 1500 |
| gtacctatac | cttgtggtgt | ccgattctgg | catctcaaca | gattacagtt | cgggggggctc 1560 |
| tcagggagtc | cacggggact | catctgatgg | ccctactcc  | cacccctatg | agaacagcct 1620 |
| tgtcccagac | tcagagcctc | tgcatcccgg | ctatgtggcc | tgctcctagg | actccagcct 1680 |
| acaacgtctt | gaacggatt  | ggtgaagcca | tacttaaagt | cagagctgac | cttggccctc 1740 |
| tgagcaggaa | gagacagcct | tgcaatgtta | agattaagag | ttatctgtct | gtatatagaa 1800 |
| atatatat   | atatcgattt | ttctacctt  | | | 1829 |

<210> SEQ ID NO 18
<211> LENGTH: 1794
<212> TYPE: DNA
<213> ORGANISM: Rattus norvegicus

<400> SEQUENCE: 18

```
ggagaaagag gaaagggaag gggaggtggg gggcaaaaga ggggggctgg agccctgagc    60
ttcctgaagc tggggctaca tcatggacca actcagggtg gcccgctggc ctcgggttag   120 cccctgtgt ctcctacttg ctggggcagc ctgggcatcc tcacccagcc tcccggaccc   180
caagtttgag agcaaagccg ccctgctggc atcccggggc tccgaagaac ttctatgctt   240
cacccagcgc ttggaagact tggtgtgttt ctgggaggaa gcggcgaact ccgggatggg   300
cttcaactac agcttctctt accagctcga aggtgaatca agaaagtcat gtcgcctgca   360
ccaggcgccc accgtccgcg ctccatgcg tttctggtgt tcactgccga ccgcggacac   420
gtcgagtttt gtgccactgg agctgcaggt gaccgaggcc tccggatctc ctcgctacca   480
ccgcatcatc catatcaatg aagtagtgct cctggacgcc ccgcggggc tgctggcgcg   540 ccgagcagaa gagggcagcc acgtggtgct gcggtggctg ccacctcccg gggctcctat   600
gaccacccac atccgctacg aggtggacgt gtcagcagga accggggctg gggggacaca   660
aagggtggag gtcctggaag gccgcactga gtgtgtcctg agcaacctgc ggggcgggac   720
gcgctacacc ttcgctgttc gagcacgcat ggccgagcca gcttcagcg gattctggag   780 cgcctggtct gagcccgcgt cgctactgac tgctagcgac ttggacccctc tcatcttgac   840 gctgtctctc attctcgtcc tcatctcact gttgctgact gtgctggccc tgctgtccca   900
ccgccgggct ctgcggcaga gatctggcc tggcatccca agcccagaga atgagtttga   960
gggtctcttc accacccaca agggtaactt ccagctatgg ctgttgcaac gcgatggctg  1020
tctgtggtgg agcccaagta gccccttccc tgaggatcca cctgcccacc tagaggtcct  1080
ctcagagcga cactggggag tgactcaggc tggggatgca ggggcagagg acaaggggcc  1140
cttactggag ccagtgggca gtgagcgggc ccaggacacc tacctggtat tggatgaatg  1200
gttgctaccc cggtgcccat gcagtgagaa cctctctggg cctggggaca gtgtagaccc  1260
tgcgactatg gatgaaggtt cagaaacatc ttcctgcccc tctgacttgg cttcaaagcc  1320
caggccagag ggcacctcgc cttccagctt tgagtacacc atcctggacc ccagctctaa  1380
gctcctgtgc cctcgggcac tgcctcctga gctaccccc actccacctc acctgaagta  1440
cctgtacctt gtggtgtccg attccggcat ctcaacagat tacagctcag ggggctccca  1500
gggagtccac ggggactcat ctgacggccc ctactccac ccctatgaga atagccttgt  1560
tccagacaca gagcctctgc ggcccagcta cgtggcctgc tcctaggact ccagcctaca  1620
gcctgtagtt cctaaaccta caacttcttg aagaggatgg ctgaggccat atttaaagcc  1680
ctggccctct gcccaggaag tgacagcctt gcaatgttaa gatggatagt tatgtctgta  1740
tatagaaata tatatatatt gatttttcaa aaaaaaaaa aaaaaaaaa aaaa           1794
```

<210> SEQ ID NO 19
<211> LENGTH: 508
<212> TYPE: PRT
<213> ORGANISM: Homo sapiens

<400> SEQUENCE: 19

```
Met Asp His Leu Gly Ala Ser Leu Trp Pro Gln Val Gly Ser Leu Cys
1               5                   10                  15

Leu Leu Leu Ala Gly Ala Ala Trp Ala Pro Pro Asn Leu Pro Asp
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
    50                  55                  60
```

```
Glu Glu Ala Ala Ser Ala Gly Val Gly Pro Gly Asn Tyr Ser Phe Ser
 65                  70                  75                  80

Tyr Gln Leu Glu Asp Glu Pro Trp Lys Leu Cys Arg Leu His Gln Ala
                 85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
    130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Glu Thr Pro Met Thr Ser
                165                 170                 175

His Ile Arg Tyr Glu Val Asp Val Ser Ala Gly Asn Gly Ala Gly Ser
                180                 185                 190

Val Gln Arg Val Glu Ile Leu Glu Gly Arg Thr Glu Cys Val Leu Ser
            195                 200                 205

Asn Leu Arg Gly Arg Thr Arg Tyr Thr Phe Ala Val Arg Ala Arg Met
210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
                260                 265                 270

Ser His Arg Arg Ala Leu Lys Gln Lys Ile Trp Pro Gly Ile Pro Ser
            275                 280                 285

Pro Glu Ser Glu Phe Glu Gly Leu Phe Thr Thr His Lys Gly Asn Phe
        290                 295                 300

Gln Leu Trp Leu Tyr Gln Asn Asp Gly Cys Leu Trp Trp Ser Pro Cys
305                 310                 315                 320

Thr Pro Phe Thr Glu Asp Pro Pro Ala Ser Leu Glu Val Leu Ser Glu
                325                 330                 335

Arg Cys Trp Gly Thr Met Gln Ala Val Glu Pro Gly Thr Asp Asp Glu
                340                 345                 350

Gly Pro Leu Leu Glu Pro Val Gly Ser Glu His Ala Gln Asp Thr Tyr
            355                 360                 365

Leu Val Leu Asp Lys Trp Leu Leu Pro Arg Asn Pro Pro Ser Glu Asp
        370                 375                 380

Leu Pro Gly Pro Gly Gly Ser Val Asp Ile Val Ala Met Asp Glu Gly
385                 390                 395                 400

Ser Glu Ala Ser Ser Cys Ser Ser Ala Leu Ala Ser Lys Pro Ser Pro
                405                 410                 415

Glu Gly Ala Ser Ala Ala Ser Phe Glu Tyr Thr Ile Leu Asp Pro Ser
            420                 425                 430

Ser Gln Leu Leu Arg Pro Trp Thr Leu Cys Pro Glu Leu Pro Pro Thr
        435                 440                 445

Pro Pro His Leu Lys Tyr Leu Tyr Leu Val Val Ser Asp Ser Gly Ile
    450                 455                 460

Ser Thr Asp Tyr Ser Ser Gly Asp Ser Gln Gly Ala Gln Gly Gly Leu
465                 470                 475                 480
```

Ser Asp Gly Pro Tyr Ser Asn Pro Tyr Glu Asn Ser Leu Ile Pro Ala
            485                 490                 495

Ala Glu Pro Leu Pro Pro Ser Tyr Val Ala Cys Ser
            500                 505

<210> SEQ ID NO 20
<211> LENGTH: 453
<212> TYPE: PRT
<213> ORGANISM: Homo sapiens

<400> SEQUENCE: 20

Met Asp His Leu Gly Ala Ser Leu Trp Pro Gln Val Gly Ser Leu Cys
1               5                   10                  15

Leu Leu Leu Ala Gly Ala Ala Trp Ala Pro Pro Asn Leu Pro Asp
            20                  25                  30

Pro Lys Phe Glu Ser Lys Ala Ala Leu Ala Ala Arg Gly Pro Glu
        35                  40                  45

Glu Leu Leu Cys Phe Thr Glu Arg Leu Glu Asp Leu Val Cys Phe Trp
50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
            260                 265                 270

Ser His Arg Arg Ala Leu Lys Gln Lys Ile Trp Pro Gly Ile Pro Ser
        275                 280                 285

Pro Glu Ser Glu Phe Glu Gly Leu Phe Thr Thr His Lys Gly Asn Phe
290                 295                 300

Gln Leu Trp Leu Tyr Gln Asn Asp Gly Cys Leu Trp Trp Ser Pro Cys
305                 310                 315                 320

Thr Pro Phe Thr Glu Asp Pro Pro Ala Ser Leu Glu Val Leu Ser Glu
                325                 330                 335

Arg Cys Trp Gly Thr Met Gln Ala Val Glu Pro Gly Thr Asp Asp Glu
            340                 345                 350

Gly Pro Leu Leu Glu Pro Val Gly Ser Glu His Ala Gln Asp Thr Tyr
            355                 360                 365

Leu Val Leu Asp Lys Trp Leu Leu Pro Arg Asn Pro Pro Ser Glu Asp
370                 375                 380

Leu Pro Gly Pro Gly Ser Val Asp Ile Val Ala Met Asp Glu Gly
385                 390                 395                 400

Ser Glu Ala Ser Ser Cys Ser Ser Ala Leu Ala Ser Lys Pro Ser Pro
                405                 410                 415

Glu Gly Ala Ser Ala Ala Ser Phe Glu Tyr Thr Ile Leu Asp Pro Ser
            420                 425                 430

Ser Gln Leu Leu Arg Pro Trp Thr Leu Cys Pro Glu Leu Pro Pro Thr
        435                 440                 445

Pro Pro His Leu Lys
    450

<210> SEQ ID NO 21
<211> LENGTH: 425
<212> TYPE: PRT
<213> ORGANISM: Homo sapiens

<400> SEQUENCE: 21

Met Asp His Leu Gly Ala Ser Leu Trp Pro Gln Val Gly Ser Leu Cys
1               5                   10                  15

Leu Leu Leu Ala Gly Ala Ala Trp Ala Pro Pro Asn Leu Pro Asp
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
    50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
    130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
    210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu

```
                260                 265                 270
Ser His Arg Arg Ala Leu Lys Gln Lys Ile Trp Pro Gly Ile Pro Ser
        275                 280                 285

Pro Glu Ser Glu Phe Glu Gly Leu Phe Thr Thr His Lys Gly Asn Phe
        290                 295                 300

Gln Leu Trp Leu Tyr Gln Asn Asp Gly Cys Leu Trp Trp Ser Pro Cys
305                 310                 315                 320

Thr Pro Phe Thr Glu Asp Pro Pro Ala Ser Leu Glu Val Leu Ser Glu
                325                 330                 335

Arg Cys Trp Gly Thr Met Gln Ala Val Glu Pro Gly Thr Asp Asp Glu
                340                 345                 350

Gly Pro Leu Leu Glu Pro Val Gly Ser Glu His Ala Gln Asp Thr Tyr
                355                 360                 365

Leu Val Leu Asp Lys Trp Leu Leu Pro Arg Asn Pro Pro Ser Glu Asp
                370                 375                 380

Leu Pro Gly Pro Gly Gly Ser Val Asp Ile Val Ala Met Asp Glu Gly
385                 390                 395                 400

Ser Glu Ala Ser Ser Cys Ser Ser Ala Leu Ala Ser Lys Pro Ser Pro
                405                 410                 415

Glu Gly Ala Ser Ala Ala Ser Phe Glu
                420                 425

<210> SEQ ID NO 22
<211> LENGTH: 484
<212> TYPE: PRT
<213> ORGANISM: Homo sapiens

<400> SEQUENCE: 22

Ala Pro Pro Pro Asn Leu Pro Asp Pro Lys Phe Glu Ser Lys Ala Ala
1               5                   10                  15

Leu Leu Ala Ala Arg Gly Pro Glu Glu Leu Leu Cys Phe Thr Glu Arg
                20                  25                  30

Leu Glu Asp Leu Val Cys Phe Trp Glu Glu Ala Ala Ser Ala Gly Val
                35                  40                  45

Gly Pro Gly Asn Tyr Ser Phe Ser Tyr Gln Leu Glu Asp Glu Pro Trp
        50                  55                  60

Lys Leu Cys Arg Leu His Gln Ala Pro Thr Ala Arg Gly Ala Val Arg
65                  70                  75                  80

Phe Trp Cys Ser Leu Pro Thr Ala Asp Thr Ser Ser Phe Val Pro Leu
                85                  90                  95

Glu Leu Arg Val Thr Ala Ala Ser Gly Ala Pro Arg Tyr His Arg Val
                100                 105                 110

Ile His Ile Asn Glu Val Val Leu Leu Asp Ala Pro Val Gly Leu Val
                115                 120                 125

Ala Arg Leu Ala Asp Glu Ser Gly His Val Val Leu Arg Trp Leu Pro
                130                 135                 140

Pro Pro Glu Thr Pro Met Thr Ser His Ile Arg Tyr Glu Val Asp Val
145                 150                 155                 160

Ser Ala Gly Asn Gly Ala Gly Ser Val Gln Arg Val Glu Ile Leu Glu
                165                 170                 175

Gly Arg Thr Glu Cys Val Leu Ser Asn Leu Arg Gly Arg Thr Arg Tyr
                180                 185                 190

Thr Phe Ala Val Arg Ala Arg Met Ala Glu Pro Ser Phe Gly Gly Phe
                195                 200                 205
```

```
Trp Ser Ala Trp Ser Glu Pro Val Ser Leu Leu Thr Pro Ser Asp Leu
    210                 215                 220
Asp Pro Leu Ile Leu Thr Leu Ser Leu Ile Leu Val Val Ile Leu Val
225                 230                 235                 240
Leu Leu Thr Val Leu Ala Leu Leu Ser His Arg Arg Ala Leu Lys Gln
            245                 250                 255
Lys Ile Trp Pro Gly Ile Pro Ser Pro Glu Ser Glu Phe Glu Gly Leu
            260                 265                 270
Phe Thr Thr His Lys Gly Asn Phe Gln Leu Trp Leu Tyr Gln Asn Asp
            275                 280                 285
Gly Cys Leu Trp Trp Ser Pro Cys Thr Pro Phe Thr Glu Asp Pro Pro
290                 295                 300
Ala Ser Leu Glu Val Leu Ser Glu Arg Cys Trp Gly Thr Met Gln Ala
305                 310                 315                 320
Val Glu Pro Gly Thr Asp Asp Glu Gly Pro Leu Leu Glu Pro Val Gly
                325                 330                 335
Ser Glu His Ala Gln Asp Thr Tyr Leu Val Leu Asp Lys Trp Leu Leu
            340                 345                 350
Pro Arg Asn Pro Pro Ser Glu Asp Leu Pro Gly Pro Gly Gly Ser Val
            355                 360                 365
Asp Ile Val Ala Met Asp Glu Gly Ser Glu Ala Ser Ser Cys Ser Ser
370                 375                 380
Ala Leu Ala Ser Lys Pro Ser Pro Glu Gly Ala Ser Ala Ala Ser Phe
385                 390                 395                 400
Glu Tyr Thr Ile Leu Asp Pro Ser Ser Gln Leu Leu Arg Pro Trp Thr
                405                 410                 415
Leu Cys Pro Glu Leu Pro Pro Thr Pro Pro His Leu Lys Tyr Leu Tyr
                420                 425                 430
Leu Val Val Ser Asp Ser Gly Ile Ser Thr Asp Tyr Ser Ser Gly Asp
            435                 440                 445
Ser Gln Gly Ala Gln Gly Gly Leu Ser Asp Gly Pro Tyr Ser Asn Pro
            450                 455                 460
Tyr Glu Asn Ser Leu Ile Pro Ala Ala Glu Pro Leu Pro Pro Ser Tyr
465                 470                 475                 480
Val Ala Cys Ser

<210> SEQ ID NO 23
<211> LENGTH: 429
<212> TYPE: PRT
<213> ORGANISM: Homo sapiens

<400> SEQUENCE: 23

Ala Pro Pro Pro Asn Leu Pro Asp Pro Lys Phe Glu Ser Lys Ala Ala
1               5                   10                  15
Leu Leu Ala Ala Arg Gly Pro Glu Glu Leu Leu Cys Phe Thr Glu Arg
            20                  25                  30
Leu Glu Asp Leu Val Cys Phe Trp Glu Glu Ala Ala Ser Ala Gly Val
        35                  40                  45
Gly Pro Gly Asn Tyr Ser Phe Ser Tyr Gln Leu Glu Asp Glu Pro Trp
    50                  55                  60
Lys Leu Cys Arg Leu His Gln Ala Pro Thr Ala Arg Gly Ala Val Arg
65                  70                  75                  80
Phe Trp Cys Ser Leu Pro Thr Ala Asp Thr Ser Ser Phe Val Pro Leu
                85                  90                  95
```

```
Glu Leu Arg Val Thr Ala Ala Ser Gly Ala Pro Arg Tyr His Arg Val
                100                 105                 110

Ile His Ile Asn Glu Val Val Leu Leu Asp Ala Pro Val Gly Leu Val
            115                 120                 125

Ala Arg Leu Ala Asp Glu Ser Gly His Val Val Leu Arg Trp Leu Pro
        130                 135                 140

Pro Pro Glu Thr Pro Met Thr Ser His Ile Arg Tyr Glu Val Asp Val
145                 150                 155                 160

Ser Ala Gly Asn Gly Ala Gly Ser Val Gln Arg Val Glu Ile Leu Glu
                165                 170                 175

Gly Arg Thr Glu Cys Val Leu Ser Asn Leu Arg Gly Arg Thr Arg Tyr
            180                 185                 190

Thr Phe Ala Val Arg Ala Arg Met Ala Glu Pro Ser Phe Gly Gly Phe
        195                 200                 205

Trp Ser Ala Trp Ser Glu Pro Val Ser Leu Leu Thr Pro Ser Asp Leu
    210                 215                 220

Asp Pro Leu Ile Leu Thr Leu Ser Leu Ile Leu Val Val Ile Leu Val
225                 230                 235                 240

Leu Leu Thr Val Leu Ala Leu Leu Ser His Arg Arg Ala Leu Lys Gln
                245                 250                 255

Lys Ile Trp Pro Gly Ile Pro Ser Pro Glu Ser Glu Phe Glu Gly Leu
            260                 265                 270

Phe Thr Thr His Lys Gly Asn Phe Gln Leu Trp Leu Tyr Gln Asn Asp
        275                 280                 285

Gly Cys Leu Trp Trp Ser Pro Cys Thr Pro Phe Thr Glu Asp Pro Pro
    290                 295                 300

Ala Ser Leu Glu Val Leu Ser Glu Arg Cys Trp Gly Thr Met Gln Ala
305                 310                 315                 320

Val Glu Pro Gly Thr Asp Asp Glu Gly Pro Leu Leu Glu Pro Val Gly
                325                 330                 335

Ser Glu His Ala Gln Asp Thr Tyr Leu Val Leu Asp Lys Trp Leu Leu
            340                 345                 350

Pro Arg Asn Pro Pro Ser Glu Asp Leu Pro Gly Pro Gly Gly Ser Val
        355                 360                 365

Asp Ile Val Ala Met Asp Glu Gly Ser Glu Ala Ser Ser Cys Ser Ser
    370                 375                 380

Ala Leu Ala Ser Lys Pro Ser Pro Glu Gly Ala Ser Ala Ala Ser Phe
385                 390                 395                 400

Glu Tyr Thr Ile Leu Asp Pro Ser Ser Gln Leu Leu Arg Pro Trp Thr
                405                 410                 415

Leu Cys Pro Glu Leu Pro Pro Thr Pro Pro His Leu Lys
            420                 425

<210> SEQ ID NO 24
<211> LENGTH: 401
<212> TYPE: PRT
<213> ORGANISM: Homo sapiens

<400> SEQUENCE: 24

Ala Pro Pro Pro Asn Leu Pro Asp Pro Lys Phe Glu Ser Lys Ala Ala
1               5                   10                  15

Leu Leu Ala Ala Arg Gly Pro Glu Glu Leu Leu Cys Phe Thr Glu Arg
            20                  25                  30

Leu Glu Asp Leu Val Cys Phe Trp Glu Glu Ala Ala Ser Ala Gly Val
        35                  40                  45
```

Gly Pro Gly Asn Tyr Ser Phe Ser Tyr Gln Leu Glu Asp Glu Pro Trp
 50                  55                  60

Lys Leu Cys Arg Leu His Gln Ala Pro Thr Ala Arg Gly Ala Val Arg
 65                  70                  75                  80

Phe Trp Cys Ser Leu Pro Thr Ala Asp Thr Ser Ser Phe Val Pro Leu
                 85                  90                  95

Glu Leu Arg Val Thr Ala Ala Ser Gly Ala Pro Arg Tyr His Arg Val
            100                 105                 110

Ile His Ile Asn Glu Val Val Leu Leu Asp Ala Pro Val Gly Leu Val
        115                 120                 125

Ala Arg Leu Ala Asp Glu Ser Gly His Val Val Leu Arg Trp Leu Pro
130                 135                 140

Pro Pro Glu Thr Pro Met Thr Ser His Ile Arg Tyr Glu Val Asp Val
145                 150                 155                 160

Ser Ala Gly Asn Gly Ala Gly Ser Val Gln Arg Val Glu Ile Leu Glu
                165                 170                 175

Gly Arg Thr Glu Cys Val Leu Ser Asn Leu Arg Gly Arg Thr Arg Tyr
            180                 185                 190

Thr Phe Ala Val Arg Ala Arg Met Ala Glu Pro Ser Phe Gly Gly Phe
        195                 200                 205

Trp Ser Ala Trp Ser Glu Pro Val Ser Leu Leu Thr Pro Ser Asp Leu
210                 215                 220

Asp Pro Leu Ile Leu Thr Leu Ser Leu Ile Leu Val Ile Leu Val
225                 230                 235                 240

Leu Leu Thr Val Leu Ala Leu Leu Ser His Arg Arg Ala Leu Lys Gln
                245                 250                 255

Lys Ile Trp Pro Gly Ile Pro Ser Pro Glu Ser Glu Phe Glu Gly Leu
            260                 265                 270

Phe Thr Thr His Lys Gly Asn Phe Gln Leu Trp Leu Tyr Gln Asn Asp
        275                 280                 285

Gly Cys Leu Trp Trp Ser Pro Cys Thr Pro Phe Thr Glu Asp Pro Pro
290                 295                 300

Ala Ser Leu Glu Val Leu Ser Glu Arg Cys Trp Gly Thr Met Gln Ala
305                 310                 315                 320

Val Glu Pro Gly Thr Asp Asp Glu Gly Pro Leu Leu Glu Pro Val Gly
                325                 330                 335

Ser Glu His Ala Gln Asp Thr Tyr Leu Val Leu Asp Lys Trp Leu Leu
            340                 345                 350

Pro Arg Asn Pro Pro Ser Glu Asp Leu Pro Gly Pro Gly Gly Ser Val
        355                 360                 365

Asp Ile Val Ala Met Asp Glu Gly Ser Glu Ala Ser Ser Cys Ser Ser
370                 375                 380

Ala Leu Ala Ser Lys Pro Ser Pro Glu Gly Ala Ser Ala Ala Ser Phe
385                 390                 395                 400

Glu

<210> SEQ ID NO 25
<211> LENGTH: 507
<212> TYPE: PRT
<213> ORGANISM: Mus musculus

<400> SEQUENCE: 25

Met Asp Lys Leu Arg Val Pro Leu Trp Pro Arg Val Gly Pro Leu Cys
 1               5                  10                  15

```
Leu Leu Leu Ala Gly Ala Ala Trp Ala Pro Ser Pro Ser Leu Pro Asp
            20                  25                  30

Pro Lys Phe Glu Ser Lys Ala Ala Leu Leu Ala Ser Arg Gly Ser Glu
        35                  40                  45

Glu Leu Leu Cys Phe Thr Gln Arg Leu Glu Asp Leu Val Cys Phe Trp
50                  55                  60

Glu Glu Ala Ala Ser Ser Gly Met Asp Phe Asn Tyr Ser Phe Ser Tyr
65                  70                  75                  80

Gln Leu Glu Gly Glu Ser Arg Lys Ser Cys Ser Leu His Gln Ala Pro
                85                  90                  95

Thr Val Arg Gly Ser Val Arg Phe Trp Cys Ser Leu Pro Thr Ala Asp
            100                 105                 110

Thr Ser Ser Phe Val Pro Leu Glu Leu Gln Val Thr Glu Ala Ser Gly
        115                 120                 125

Ser Pro Arg Tyr His Arg Ile Ile His Ile Asn Glu Val Val Leu Leu
130                 135                 140

Asp Ala Pro Ala Gly Leu Leu Ala Arg Arg Ala Glu Glu Gly Ser His
145                 150                 155                 160

Val Val Leu Arg Trp Leu Pro Pro Gly Ala Pro Met Thr Thr His
                165                 170                 175

Ile Arg Tyr Glu Val Asp Val Ser Ala Gly Asn Arg Ala Gly Gly Thr
            180                 185                 190

Gln Arg Val Glu Val Leu Glu Gly Arg Thr Glu Cys Val Leu Ser Asn
        195                 200                 205

Leu Arg Gly Gly Thr Arg Tyr Thr Phe Ala Val Arg Ala Arg Met Ala
210                 215                 220

Glu Pro Ser Phe Ser Gly Phe Trp Ser Ala Trp Ser Glu Pro Ala Ser
225                 230                 235                 240

Leu Leu Thr Ala Ser Asp Leu Asp Pro Leu Ile Leu Thr Leu Ser Leu
                245                 250                 255

Ile Leu Val Leu Ile Ser Leu Leu Thr Val Leu Ala Leu Leu Ser
            260                 265                 270

His Arg Arg Thr Leu Gln Gln Lys Ile Trp Pro Gly Ile Pro Ser Pro
        275                 280                 285

Glu Ser Glu Phe Glu Gly Leu Phe Thr Thr His Lys Gly Asn Phe Gln
290                 295                 300

Leu Trp Leu Leu Gln Arg Asp Gly Cys Leu Trp Trp Ser Pro Gly Ser
305                 310                 315                 320

Ser Phe Pro Glu Asp Pro Pro Ala His Leu Glu Val Leu Ser Glu Pro
                325                 330                 335

Arg Trp Ala Val Thr Gln Ala Gly Asp Pro Gly Ala Asp Asp Glu Gly
            340                 345                 350

Pro Leu Leu Glu Pro Val Gly Ser Glu His Ala Gln Asp Thr Tyr Leu
        355                 360                 365

Val Leu Asp Lys Trp Leu Leu Pro Arg Thr Pro Cys Ser Glu Asn Leu
370                 375                 380

Ser Gly Pro Gly Gly Ser Val Asp Pro Val Thr Met Asp Glu Ala Ser
385                 390                 395                 400

Glu Thr Ser Ser Cys Pro Ser Asp Leu Ala Ser Lys Pro Arg Pro Glu
                405                 410                 415

Gly Thr Ser Pro Ser Ser Phe Glu Tyr Thr Ile Leu Asp Pro Ser Ser
            420                 425                 430
```

```
Gln Leu Leu Cys Pro Arg Ala Leu Pro Pro Glu Leu Pro Pro Thr Pro
            435                 440                 445

Pro His Leu Lys Tyr Leu Tyr Leu Val Val Ser Asp Ser Gly Ile Ser
    450                 455                 460

Thr Asp Tyr Ser Ser Gly Gly Ser Gln Gly Val His Gly Asp Ser Ser
465                 470                 475                 480

Asp Gly Pro Tyr Ser His Pro Tyr Glu Asn Ser Leu Val Pro Asp Ser
                485                 490                 495

Glu Pro Leu His Pro Gly Tyr Val Ala Cys Ser
                500                 505

<210> SEQ ID NO 26
<211> LENGTH: 452
<212> TYPE: PRT
<213> ORGANISM: Mus musculus

<400> SEQUENCE: 26

Met Asp Lys Leu Arg Val Pro Leu Trp Pro Arg Val Gly Pro Leu Cys
1               5                   10                  15

Leu Leu Leu Ala Gly Ala Ala Trp Ala Pro Ser Pro Ser Leu Pro Asp
            20                  25                  30

Pro Lys Phe Glu Ser Lys Ala Ala Leu Leu Ala Ser Arg Gly Ser Glu
        35                  40                  45

Glu Leu Leu Cys Phe Thr Gln Arg Leu Glu Asp Leu Val Cys Phe Trp
    50                  55                  60

Glu Glu Ala Ala Ser Ser Gly Met Asp Phe Asn Tyr Ser Phe Ser Tyr
65                  70                  75                  80

Gln Leu Glu Gly Glu Ser Arg Lys Ser Cys Ser Leu His Gln Ala Pro
                85                  90                  95

Thr Val Arg Gly Ser Val Arg Phe Trp Cys Ser Leu Pro Thr Ala Asp
            100                 105                 110

Thr Ser Ser Phe Val Pro Leu Glu Leu Gln Val Thr Glu Ala Ser Gly
        115                 120                 125

Ser Pro Arg Tyr His Arg Ile Ile His Ile Asn Glu Val Val Leu Leu
    130                 135                 140

Asp Ala Pro Ala Gly Leu Leu Ala Arg Arg Ala Glu Glu Gly Ser His
145                 150                 155                 160

Val Val Leu Arg Trp Leu Pro Pro Pro Gly Ala Pro Met Thr Thr His
                165                 170                 175

Ile Arg Tyr Glu Val Asp Val Ser Ala Gly Asn Arg Ala Gly Gly Thr
            180                 185                 190

Gln Arg Val Glu Val Leu Glu Gly Arg Thr Glu Cys Val Leu Ser Asn
        195                 200                 205

Leu Arg Gly Gly Thr Arg Tyr Thr Phe Ala Val Arg Ala Arg Met Ala
    210                 215                 220

Glu Pro Ser Phe Ser Gly Phe Trp Ser Ala Trp Ser Glu Pro Ala Ser
225                 230                 235                 240

Leu Leu Thr Ala Ser Asp Leu Asp Pro Leu Ile Leu Thr Leu Ser Leu
                245                 250                 255

Ile Leu Val Leu Ile Ser Leu Leu Leu Thr Val Leu Ala Leu Leu Ser
            260                 265                 270

His Arg Arg Thr Leu Gln Gln Lys Ile Trp Pro Gly Ile Pro Ser Pro
        275                 280                 285

Glu Ser Glu Phe Glu Gly Leu Phe Thr Thr His Lys Gly Asn Phe Gln
    290                 295                 300
```

```
Leu Trp Leu Leu Gln Arg Asp Gly Cys Leu Trp Trp Ser Pro Gly Ser
305                 310                 315                 320

Ser Phe Pro Glu Asp Pro Pro Ala His Leu Glu Val Leu Ser Glu Pro
                325                 330                 335

Arg Trp Ala Val Thr Gln Ala Gly Asp Pro Gly Ala Asp Asp Glu Gly
            340                 345                 350

Pro Leu Leu Glu Pro Val Gly Ser Glu His Ala Gln Asp Thr Tyr Leu
        355                 360                 365

Val Leu Asp Lys Trp Leu Leu Pro Arg Thr Pro Cys Ser Glu Asn Leu
370                 375                 380

Ser Gly Pro Gly Gly Ser Val Asp Pro Val Thr Met Asp Glu Ala Ser
385                 390                 395                 400

Glu Thr Ser Ser Cys Pro Ser Asp Leu Ala Ser Lys Pro Arg Pro Glu
                405                 410                 415

Gly Thr Ser Pro Ser Ser Phe Glu Tyr Thr Ile Leu Asp Pro Ser Ser
                420                 425                 430

Gln Leu Cys Pro Arg Ala Leu Pro Pro Glu Leu Pro Pro Thr Pro
        435                 440                 445

Pro His Leu Lys
    450

<210> SEQ ID NO 27
<211> LENGTH: 424
<212> TYPE: PRT
<213> ORGANISM: Mus musculus

<400> SEQUENCE: 27

Met Asp Lys Leu Arg Val Pro Leu Trp Pro Arg Val Gly Pro Leu Cys
1               5                   10                  15

Leu Leu Leu Ala Gly Ala Ala Trp Ala Pro Ser Pro Ser Leu Pro Asp
            20                  25                  30

Pro Lys Phe Glu Ser Lys Ala Ala Leu Leu Ala Ser Arg Gly Ser Glu
        35                  40                  45

Glu Leu Leu Cys Phe Thr Gln Arg Leu Glu Asp Leu Val Cys Phe Trp
50                  55                  60

Glu Glu Ala Ala Ser Ser Gly Met Asp Phe Asn Tyr Ser Phe Ser Tyr
65                  70                  75                  80

Gln Leu Glu Gly Glu Ser Arg Lys Ser Cys Ser Leu His Gln Ala Pro
                85                  90                  95

Thr Val Arg Gly Ser Val Arg Phe Trp Cys Ser Leu Pro Thr Ala Asp
            100                 105                 110

Thr Ser Ser Phe Val Pro Leu Glu Leu Gln Val Thr Glu Ala Ser Gly
        115                 120                 125

Ser Pro Arg Tyr His Arg Ile Ile His Ile Asn Glu Val Val Leu Leu
130                 135                 140

Asp Ala Pro Ala Gly Leu Leu Ala Arg Arg Ala Glu Glu Gly Ser His
145                 150                 155                 160

Val Val Leu Arg Trp Leu Pro Pro Pro Gly Ala Pro Met Thr Thr His
                165                 170                 175

Ile Arg Tyr Glu Val Asp Val Ser Ala Gly Asn Arg Ala Gly Gly Thr
            180                 185                 190

Gln Arg Val Glu Val Leu Glu Gly Arg Thr Glu Cys Val Leu Ser Asn
        195                 200                 205

Leu Arg Gly Gly Thr Arg Tyr Thr Phe Ala Val Arg Ala Arg Met Ala
```

```
                210                 215                 220
Glu Pro Ser Phe Ser Gly Phe Trp Ser Ala Trp Ser Glu Pro Ala Ser
225                 230                 235                 240

Leu Leu Thr Ala Ser Asp Leu Asp Pro Leu Ile Leu Thr Leu Ser Leu
                245                 250                 255

Ile Leu Val Leu Ile Ser Leu Leu Thr Val Leu Ala Leu Leu Ser
                260                 265                 270

His Arg Arg Thr Leu Gln Gln Lys Ile Trp Pro Gly Ile Pro Ser Pro
                275                 280                 285

Glu Ser Glu Phe Glu Gly Leu Phe Thr Thr His Lys Gly Asn Phe Gln
                290                 295                 300

Leu Trp Leu Leu Gln Arg Asp Gly Cys Leu Trp Trp Ser Pro Gly Ser
305                 310                 315                 320

Ser Phe Pro Glu Asp Pro Pro Ala His Leu Glu Val Leu Ser Glu Pro
                325                 330                 335

Arg Trp Ala Val Thr Gln Ala Gly Asp Pro Gly Ala Asp Asp Glu Gly
                340                 345                 350

Pro Leu Leu Glu Pro Val Gly Ser Glu His Ala Gln Asp Thr Tyr Leu
                355                 360                 365

Val Leu Asp Lys Trp Leu Leu Pro Arg Thr Pro Cys Ser Glu Asn Leu
                370                 375                 380

Ser Gly Pro Gly Gly Ser Val Asp Pro Val Thr Met Asp Glu Ala Ser
385                 390                 395                 400

Glu Thr Ser Ser Cys Pro Ser Asp Leu Ala Ser Lys Pro Arg Pro Glu
                405                 410                 415

Gly Thr Ser Pro Ser Ser Phe Glu
                420

<210> SEQ ID NO 28
<211> LENGTH: 483
<212> TYPE: PRT
<213> ORGANISM: Mus musculus

<400> SEQUENCE: 28

Ala Pro Ser Pro Ser Leu Pro Asp Pro Lys Phe Glu Ser Lys Ala Ala
1               5                   10                  15

Leu Leu Ala Ser Arg Gly Ser Glu Glu Leu Leu Cys Phe Thr Gln Arg
                20                  25                  30

Leu Glu Asp Leu Val Cys Phe Trp Glu Glu Ala Ala Ser Ser Gly Met
            35                  40                  45

Asp Phe Asn Tyr Ser Phe Ser Tyr Gln Leu Glu Gly Glu Ser Arg Lys
        50                  55                  60

Ser Cys Ser Leu His Gln Ala Pro Thr Val Arg Gly Ser Val Arg Phe
65                  70                  75                  80

Trp Cys Ser Leu Pro Thr Ala Asp Thr Ser Ser Phe Val Pro Leu Glu
                85                  90                  95

Leu Gln Val Thr Glu Ala Ser Gly Ser Pro Arg Tyr His Arg Ile Ile
                100                 105                 110

His Ile Asn Glu Val Val Leu Leu Asp Ala Pro Ala Gly Leu Leu Ala
            115                 120                 125

Arg Arg Ala Glu Glu Gly Ser His Val Val Leu Arg Trp Leu Pro Pro
130                 135                 140

Pro Gly Ala Pro Met Thr Thr His Ile Arg Tyr Glu Val Asp Val Ser
145                 150                 155                 160
```

Ala Gly Asn Arg Ala Gly Gly Thr Gln Arg Val Glu Val Leu Glu Gly
            165                 170                 175

Arg Thr Glu Cys Val Leu Ser Asn Leu Arg Gly Gly Thr Arg Tyr Thr
        180                 185                 190

Phe Ala Val Arg Ala Arg Met Ala Glu Pro Ser Phe Ser Gly Phe Trp
        195                 200                 205

Ser Ala Trp Ser Glu Pro Ala Ser Leu Leu Thr Ala Ser Asp Leu Asp
        210                 215                 220

Pro Leu Ile Leu Thr Leu Ser Leu Ile Leu Val Leu Ile Ser Leu Leu
225                 230                 235                 240

Leu Thr Val Leu Ala Leu Leu Ser His Arg Arg Thr Leu Gln Gln Lys
                245                 250                 255

Ile Trp Pro Gly Ile Pro Ser Pro Glu Ser Glu Phe Glu Gly Leu Phe
                260                 265                 270

Thr Thr His Lys Gly Asn Phe Gln Leu Trp Leu Leu Gln Arg Asp Gly
            275                 280                 285

Cys Leu Trp Trp Ser Pro Gly Ser Ser Phe Pro Glu Asp Pro Pro Ala
        290                 295                 300

His Leu Glu Val Leu Ser Glu Pro Arg Trp Ala Val Thr Gln Ala Gly
305                 310                 315                 320

Asp Pro Gly Ala Asp Asp Glu Gly Pro Leu Leu Glu Pro Val Gly Ser
                325                 330                 335

Glu His Ala Gln Asp Thr Tyr Leu Val Leu Asp Lys Trp Leu Leu Pro
                340                 345                 350

Arg Thr Pro Cys Ser Glu Asn Leu Ser Gly Pro Gly Gly Ser Val Asp
            355                 360                 365

Pro Val Thr Met Asp Glu Ala Ser Glu Thr Ser Ser Cys Pro Ser Asp
        370                 375                 380

Leu Ala Ser Lys Pro Arg Pro Glu Gly Thr Ser Pro Ser Ser Phe Glu
385                 390                 395                 400

Tyr Thr Ile Leu Asp Pro Ser Ser Gln Leu Leu Cys Pro Arg Ala Leu
                405                 410                 415

Pro Pro Glu Leu Pro Pro Thr Pro Pro His Leu Lys Tyr Leu Tyr Leu
                420                 425                 430

Val Val Ser Asp Ser Gly Ile Ser Thr Asp Tyr Ser Ser Gly Gly Ser
            435                 440                 445

Gln Gly Val His Gly Asp Ser Ser Asp Gly Pro Tyr Ser His Pro Tyr
        450                 455                 460

Glu Asn Ser Leu Val Pro Asp Ser Glu Pro Leu His Pro Gly Tyr Val
465                 470                 475                 480

Ala Cys Ser

<210> SEQ ID NO 29
<211> LENGTH: 428
<212> TYPE: PRT
<213> ORGANISM: Mus musculus

<400> SEQUENCE: 29

Ala Pro Ser Pro Ser Leu Pro Asp Pro Lys Phe Glu Ser Lys Ala Ala
1               5                   10                  15

Leu Leu Ala Ser Arg Gly Ser Glu Glu Leu Leu Cys Phe Thr Gln Arg
            20                  25                  30

Leu Glu Asp Leu Val Cys Phe Trp Glu Glu Ala Ala Ser Ser Gly Met
        35                  40                  45

```
Asp Phe Asn Tyr Ser Phe Ser Tyr Gln Leu Glu Gly Glu Ser Arg Lys
 50                  55                  60
Ser Cys Ser Leu His Gln Ala Pro Thr Val Arg Gly Ser Val Arg Phe
 65                  70                  75                  80
Trp Cys Ser Leu Pro Thr Ala Asp Thr Ser Ser Phe Val Pro Leu Glu
                 85                  90                  95
Leu Gln Val Thr Glu Ala Ser Gly Ser Pro Arg Tyr His Arg Ile Ile
            100                 105                 110
His Ile Asn Glu Val Val Leu Leu Asp Ala Pro Ala Gly Leu Leu Ala
        115                 120                 125
Arg Arg Ala Glu Glu Gly Ser His Val Val Leu Arg Trp Leu Pro Pro
130                 135                 140
Pro Gly Ala Pro Met Thr Thr His Ile Arg Tyr Glu Val Asp Val Ser
145                 150                 155                 160
Ala Gly Asn Arg Ala Gly Gly Thr Gln Arg Val Glu Val Leu Glu Gly
                165                 170                 175
Arg Thr Glu Cys Val Leu Ser Asn Leu Arg Gly Gly Thr Arg Tyr Thr
            180                 185                 190
Phe Ala Val Arg Ala Arg Met Ala Glu Pro Ser Phe Ser Gly Phe Trp
        195                 200                 205
Ser Ala Trp Ser Glu Pro Ala Ser Leu Leu Thr Ala Ser Asp Leu Asp
210                 215                 220
Pro Leu Ile Leu Thr Leu Ser Leu Ile Leu Val Leu Ile Ser Leu Leu
225                 230                 235                 240
Leu Thr Val Leu Ala Leu Leu Ser His Arg Arg Thr Leu Gln Gln Lys
                245                 250                 255
Ile Trp Pro Gly Ile Pro Ser Pro Glu Ser Glu Phe Glu Gly Leu Phe
            260                 265                 270
Thr Thr His Lys Gly Asn Phe Gln Leu Trp Leu Leu Gln Arg Asp Gly
        275                 280                 285
Cys Leu Trp Trp Ser Pro Gly Ser Ser Phe Pro Glu Asp Pro Pro Ala
290                 295                 300
His Leu Glu Val Leu Ser Glu Pro Arg Trp Ala Val Thr Gln Ala Gly
305                 310                 315                 320
Asp Pro Gly Ala Asp Asp Glu Gly Pro Leu Leu Glu Pro Val Gly Ser
                325                 330                 335
Glu His Ala Gln Asp Thr Tyr Leu Val Leu Asp Lys Trp Leu Leu Pro
            340                 345                 350
Arg Thr Pro Cys Ser Glu Asn Leu Ser Gly Pro Gly Gly Ser Val Asp
        355                 360                 365
Pro Val Thr Met Asp Glu Ala Ser Glu Thr Ser Ser Cys Pro Ser Asp
370                 375                 380
Leu Ala Ser Lys Pro Arg Pro Glu Gly Thr Ser Pro Ser Ser Phe Glu
385                 390                 395                 400
Tyr Thr Ile Leu Asp Pro Ser Ser Gln Leu Leu Cys Pro Arg Ala Leu
                405                 410                 415
Pro Pro Glu Leu Pro Pro Thr Pro Pro His Leu Lys
            420                 425
```

<210> SEQ ID NO 30
<211> LENGTH: 400
<212> TYPE: PRT
<213> ORGANISM: Mus musculus

<400> SEQUENCE: 30

Ala Pro Ser Pro Ser Leu Pro Asp Pro Lys Phe Glu Ser Lys Ala Ala
1               5                   10                  15

Leu Leu Ala Ser Arg Gly Ser Glu Glu Leu Leu Cys Phe Thr Gln Arg
            20                  25                  30

Leu Glu Asp Leu Val Cys Phe Trp Glu Ala Ala Ser Ser Gly Met
        35                  40                  45

Asp Phe Asn Tyr Ser Phe Ser Tyr Gln Leu Glu Gly Glu Ser Arg Lys
        50                  55                  60

Ser Cys Ser Leu His Gln Ala Pro Thr Val Arg Gly Ser Val Arg Phe
65                  70                  75                  80

Trp Cys Ser Leu Pro Thr Ala Asp Thr Ser Phe Val Pro Leu Glu
                85                  90                  95

Leu Gln Val Thr Glu Ala Ser Gly Ser Pro Arg Tyr His Arg Ile Ile
            100                 105                 110

His Ile Asn Glu Val Val Leu Leu Asp Ala Pro Ala Gly Leu Leu Ala
            115                 120                 125

Arg Arg Ala Glu Glu Gly Ser His Val Val Leu Arg Trp Leu Pro Pro
            130                 135                 140

Pro Gly Ala Pro Met Thr Thr His Ile Arg Tyr Glu Val Asp Val Ser
145                 150                 155                 160

Ala Gly Asn Arg Ala Gly Gly Thr Gln Arg Val Glu Val Leu Glu Gly
                165                 170                 175

Arg Thr Glu Cys Val Leu Ser Asn Leu Arg Gly Gly Thr Arg Tyr Thr
            180                 185                 190

Phe Ala Val Arg Ala Arg Met Ala Glu Pro Ser Phe Ser Gly Phe Trp
            195                 200                 205

Ser Ala Trp Ser Glu Pro Ala Ser Leu Leu Thr Ala Ser Asp Leu Asp
210                 215                 220

Pro Leu Ile Leu Thr Leu Ser Leu Ile Leu Val Leu Ile Ser Leu Leu
225                 230                 235                 240

Leu Thr Val Leu Ala Leu Leu Ser His Arg Arg Thr Leu Gln Gln Lys
            245                 250                 255

Ile Trp Pro Gly Ile Pro Ser Pro Glu Ser Glu Phe Glu Gly Leu Phe
            260                 265                 270

Thr Thr His Lys Gly Asn Phe Gln Leu Trp Leu Leu Gln Arg Asp Gly
        275                 280                 285

Cys Leu Trp Trp Ser Pro Gly Ser Ser Phe Pro Glu Asp Pro Pro Ala
        290                 295                 300

His Leu Glu Val Leu Ser Glu Pro Arg Trp Ala Val Thr Gln Ala Gly
305                 310                 315                 320

Asp Pro Gly Ala Asp Asp Glu Gly Pro Leu Leu Glu Pro Val Gly Ser
                325                 330                 335

Glu His Ala Gln Asp Thr Tyr Leu Val Leu Asp Lys Trp Leu Leu Pro
            340                 345                 350

Arg Thr Pro Cys Ser Glu Asn Leu Ser Gly Pro Gly Gly Ser Val Asp
            355                 360                 365

Pro Val Thr Met Asp Glu Ala Ser Glu Thr Ser Ser Cys Pro Ser Asp
370                 375                 380

Leu Ala Ser Lys Pro Arg Pro Glu Gly Thr Ser Pro Ser Ser Phe Glu
385                 390                 395                 400

<210> SEQ ID NO 31
<211> LENGTH: 507

<212> TYPE: PRT
<213> ORGANISM: Rattus norvegicus

<400> SEQUENCE: 31

```
Met Asp Gln Leu Arg Val Ala Arg Trp Pro Arg Val Ser Pro Leu Cys
1               5                   10                  15
Leu Leu Leu Ala Gly Ala Ala Trp Ala Ser Ser Pro Ser Leu Pro Asp
                20                  25                  30
Pro Lys Phe Glu Ser Lys Ala Ala Leu Leu Ala Ser Arg Gly Ser Glu
            35                  40                  45
Glu Leu Leu Cys Phe Thr Gln Arg Leu Glu Asp Leu Val Cys Phe Trp
        50                  55                  60
Glu Glu Ala Ala Asn Ser Gly Met Gly Phe Asn Tyr Ser Phe Ser Tyr
65                  70                  75                  80
Gln Leu Glu Gly Glu Ser Arg Lys Ser Cys Arg Leu His Gln Ala Pro
                85                  90                  95
Thr Val Arg Gly Ser Met Arg Phe Trp Cys Ser Leu Pro Thr Ala Asp
            100                 105                 110
Thr Ser Ser Phe Val Pro Leu Glu Leu Gln Val Thr Glu Ala Ser Gly
        115                 120                 125
Ser Pro Arg Tyr His Arg Ile Ile His Ile Asn Glu Val Val Leu Leu
130                 135                 140
Asp Ala Pro Ala Gly Leu Leu Ala Arg Arg Ala Glu Glu Gly Ser His
145                 150                 155                 160
Val Val Leu Arg Trp Leu Pro Pro Gly Ala Pro Met Thr Thr His
                165                 170                 175
Ile Arg Tyr Glu Val Asp Val Ser Ala Gly Asn Arg Ala Gly Gly Thr
            180                 185                 190
Gln Arg Val Glu Val Leu Glu Gly Arg Thr Glu Cys Val Leu Ser Asn
        195                 200                 205
Leu Arg Gly Gly Thr Arg Tyr Thr Phe Ala Val Arg Ala Arg Met Ala
210                 215                 220
Glu Pro Ser Phe Ser Gly Phe Trp Ser Ala Trp Ser Glu Pro Ala Ser
225                 230                 235                 240
Leu Leu Thr Ala Ser Asp Leu Asp Pro Leu Ile Leu Thr Leu Ser Leu
                245                 250                 255
Ile Leu Val Leu Ile Ser Leu Leu Leu Thr Val Leu Ala Leu Leu Ser
            260                 265                 270
His Arg Arg Ala Leu Arg Gln Lys Ile Trp Pro Gly Ile Pro Ser Pro
        275                 280                 285
Glu Asn Glu Phe Glu Gly Leu Phe Thr Thr His Lys Gly Asn Phe Gln
290                 295                 300
Leu Trp Leu Leu Gln Arg Asp Gly Cys Leu Trp Trp Ser Pro Ser Ser
305                 310                 315                 320
Pro Phe Pro Glu Asp Pro Pro Ala His Leu Glu Val Leu Ser Glu Arg
                325                 330                 335
His Trp Gly Val Thr Gln Ala Gly Asp Ala Gly Ala Glu Asp Lys Gly
            340                 345                 350
Pro Leu Leu Glu Pro Val Gly Ser Glu Arg Ala Gln Asp Thr Tyr Leu
        355                 360                 365
Val Leu Asp Glu Trp Leu Leu Pro Arg Cys Pro Cys Ser Glu Asn Leu
370                 375                 380
Ser Gly Pro Gly Asp Ser Val Asp Pro Ala Thr Met Asp Glu Gly Ser
385                 390                 395                 400
```

```
Glu Thr Ser Ser Cys Pro Ser Asp Leu Ala Ser Lys Pro Arg Pro Glu
                405                 410                 415

Gly Thr Ser Pro Ser Ser Phe Glu Tyr Thr Ile Leu Asp Pro Ser Ser
            420                 425                 430

Lys Leu Leu Cys Pro Arg Ala Leu Pro Pro Glu Leu Pro Pro Thr Pro
        435                 440                 445

Pro His Leu Lys Tyr Leu Tyr Leu Val Val Ser Asp Ser Gly Ile Ser
    450                 455                 460

Thr Asp Tyr Ser Ser Gly Gly Ser Gln Gly Val His Gly Asp Ser Ser
465                 470                 475                 480

Asp Gly Pro Tyr Ser His Pro Tyr Glu Asn Ser Leu Val Pro Asp Thr
                485                 490                 495

Glu Pro Leu Arg Pro Ser Tyr Val Ala Cys Ser
            500                 505

<210> SEQ ID NO 32
<211> LENGTH: 452
<212> TYPE: PRT
<213> ORGANISM: Rattus norvegicus

<400> SEQUENCE: 32

Met Asp Gln Leu Arg Val Ala Arg Trp Pro Arg Val Ser Pro Leu Cys
1               5                   10                  15

Leu Leu Leu Ala Gly Ala Ala Trp Ala Ser Ser Pro Ser Leu Pro Asp
            20                  25                  30

Pro Lys Phe Glu Ser Lys Ala Ala Leu Leu Ala Ser Arg Gly Ser Glu
        35                  40                  45

Glu Leu Leu Cys Phe Thr Gln Arg Leu Glu Asp Leu Val Cys Phe Trp
    50                  55                  60

Glu Glu Ala Ala Asn Ser Gly Met Gly Phe Asn Tyr Ser Phe Ser Tyr
65                  70                  75                  80

Gln Leu Glu Gly Glu Ser Arg Lys Ser Cys Arg Leu His Gln Ala Pro
                85                  90                  95

Thr Val Arg Gly Ser Met Arg Phe Trp Cys Ser Leu Pro Thr Ala Asp
            100                 105                 110

Thr Ser Ser Phe Val Pro Leu Glu Leu Gln Val Thr Glu Ala Ser Gly
        115                 120                 125

Ser Pro Arg Tyr His Arg Ile Ile His Ile Asn Glu Val Val Leu Leu
    130                 135                 140

Asp Ala Pro Ala Gly Leu Leu Ala Arg Arg Ala Glu Glu Gly Ser His
145                 150                 155                 160

Val Val Leu Arg Trp Leu Pro Pro Gly Ala Pro Met Thr Thr His
                165                 170                 175

Ile Arg Tyr Glu Val Asp Val Ser Ala Gly Asn Arg Ala Gly Gly Thr
                180                 185                 190

Gln Arg Val Glu Val Leu Glu Gly Arg Thr Glu Cys Val Leu Ser Asn
            195                 200                 205

Leu Arg Gly Gly Thr Arg Tyr Thr Phe Ala Val Arg Ala Arg Met Ala
        210                 215                 220

Glu Pro Ser Phe Ser Gly Phe Trp Ser Ala Trp Ser Glu Pro Ala Ser
225                 230                 235                 240

Leu Leu Thr Ala Ser Asp Leu Asp Pro Leu Ile Leu Thr Leu Ser Leu
                245                 250                 255

Ile Leu Val Leu Ile Ser Leu Leu Leu Thr Val Leu Ala Leu Leu Ser
```

```
                    260                 265                 270
His Arg Arg Ala Leu Arg Gln Lys Ile Trp Pro Gly Ile Pro Ser Pro
            275                 280                 285

Glu Asn Glu Phe Glu Gly Leu Phe Thr Thr His Lys Gly Asn Phe Gln
        290                 295                 300

Leu Trp Leu Leu Gln Arg Asp Gly Cys Leu Trp Ser Pro Ser Ser
305                 310                 315                 320

Pro Phe Pro Glu Asp Pro Pro Ala His Leu Glu Val Leu Ser Glu Arg
                325                 330                 335

His Trp Gly Val Thr Gln Ala Gly Asp Ala Gly Ala Glu Asp Lys Gly
            340                 345                 350

Pro Leu Leu Glu Pro Val Gly Ser Glu Arg Ala Gln Asp Thr Tyr Leu
        355                 360                 365

Val Leu Asp Glu Trp Leu Leu Pro Arg Cys Pro Cys Ser Glu Asn Leu
    370                 375                 380

Ser Gly Pro Gly Asp Ser Val Asp Pro Ala Thr Met Asp Glu Gly Ser
385                 390                 395                 400

Glu Thr Ser Ser Cys Pro Ser Asp Leu Ala Ser Lys Pro Arg Pro Glu
                405                 410                 415

Gly Thr Ser Pro Ser Ser Phe Glu Tyr Thr Ile Leu Asp Pro Ser Ser
            420                 425                 430

Lys Leu Leu Cys Pro Arg Ala Leu Pro Pro Glu Leu Pro Pro Thr Pro
        435                 440                 445

Pro His Leu Lys
    450

<210> SEQ ID NO 33
<211> LENGTH: 424
<212> TYPE: PRT
<213> ORGANISM: Rattus norvegicus

<400> SEQUENCE: 33

Met Asp Gln Leu Arg Val Ala Arg Trp Pro Arg Val Ser Pro Leu Cys
1               5                   10                  15

Leu Leu Leu Ala Gly Ala Ala Trp Ala Ser Ser Pro Ser Leu Pro Asp
            20                  25                  30

Pro Lys Phe Glu Ser Lys Ala Ala Leu Leu Ala Ser Arg Gly Ser Glu
        35                  40                  45

Glu Leu Leu Cys Phe Thr Gln Arg Leu Glu Asp Leu Val Cys Phe Trp
    50                  55                  60

Glu Glu Ala Ala Asn Ser Gly Met Gly Phe Asn Tyr Ser Phe Ser Tyr
65                  70                  75                  80

Gln Leu Glu Gly Glu Ser Arg Lys Ser Cys Arg Leu His Gln Ala Pro
                85                  90                  95

Thr Val Arg Gly Ser Met Arg Phe Trp Cys Ser Leu Pro Thr Ala Asp
            100                 105                 110

Thr Ser Ser Phe Val Pro Leu Glu Leu Gln Val Thr Glu Ala Ser Gly
        115                 120                 125

Ser Pro Arg Tyr His Arg Ile Ile His Ile Asn Glu Val Val Leu Leu
    130                 135                 140

Asp Ala Pro Ala Gly Leu Leu Ala Arg Arg Ala Glu Glu Gly Ser His
145                 150                 155                 160

Val Val Leu Arg Trp Leu Pro Pro Pro Gly Ala Pro Met Thr Thr His
                165                 170                 175
```

Ile Arg Tyr Glu Val Asp Val Ser Ala Gly Asn Arg Ala Gly Gly Thr
            180                 185                 190

Gln Arg Val Glu Val Leu Glu Gly Arg Thr Glu Cys Val Leu Ser Asn
        195                 200                 205

Leu Arg Gly Gly Thr Arg Tyr Thr Phe Ala Val Arg Ala Arg Met Ala
    210                 215                 220

Glu Pro Ser Phe Ser Gly Phe Trp Ser Ala Trp Ser Glu Pro Ala Ser
225                 230                 235                 240

Leu Leu Thr Ala Ser Asp Leu Asp Pro Leu Ile Leu Thr Leu Ser Leu
                245                 250                 255

Ile Leu Val Leu Ile Ser Leu Leu Leu Thr Val Leu Ala Leu Leu Ser
            260                 265                 270

His Arg Arg Ala Leu Arg Gln Lys Ile Trp Pro Gly Ile Pro Ser Pro
        275                 280                 285

Glu Asn Glu Phe Glu Gly Leu Phe Thr Thr His Lys Gly Asn Phe Gln
    290                 295                 300

Leu Trp Leu Leu Gln Arg Asp Gly Cys Leu Trp Trp Ser Pro Ser Ser
305                 310                 315                 320

Pro Phe Pro Glu Asp Pro Pro Ala His Leu Glu Val Leu Ser Glu Arg
                325                 330                 335

His Trp Gly Val Thr Gln Ala Gly Asp Ala Gly Ala Glu Asp Lys Gly
            340                 345                 350

Pro Leu Leu Glu Pro Val Gly Ser Glu Arg Ala Gln Asp Thr Tyr Leu
        355                 360                 365

Val Leu Asp Glu Trp Leu Leu Pro Arg Cys Pro Cys Ser Glu Asn Leu
    370                 375                 380

Ser Gly Pro Gly Asp Ser Val Asp Pro Ala Thr Met Asp Glu Gly Ser
385                 390                 395                 400

Glu Thr Ser Ser Cys Pro Ser Asp Leu Ala Ser Lys Pro Arg Pro Glu
                405                 410                 415

Gly Thr Ser Pro Ser Ser Phe Glu
            420

<210> SEQ ID NO 34
<211> LENGTH: 483
<212> TYPE: PRT
<213> ORGANISM: Rattus norvegicus

<400> SEQUENCE: 34

Ala Ser Ser Pro Ser Leu Pro Asp Pro Lys Phe Glu Ser Lys Ala Ala
1               5                   10                  15

Leu Leu Ala Ser Arg Gly Ser Glu Glu Leu Leu Cys Phe Thr Gln Arg
            20                  25                  30

Leu Glu Asp Leu Val Cys Phe Trp Glu Glu Ala Ala Asn Ser Gly Met
        35                  40                  45

Gly Phe Asn Tyr Ser Phe Ser Tyr Gln Leu Glu Gly Glu Ser Arg Lys
    50                  55                  60

Ser Cys Arg Leu His Gln Ala Pro Thr Val Arg Gly Ser Met Arg Phe
65                  70                  75                  80

Trp Cys Ser Leu Pro Thr Ala Asp Thr Ser Ser Phe Val Pro Leu Glu
                85                  90                  95

Leu Gln Val Thr Glu Ala Ser Gly Ser Pro Arg Tyr His Arg Ile Ile
            100                 105                 110

His Ile Asn Glu Val Val Leu Leu Asp Ala Pro Ala Gly Leu Leu Ala
        115                 120                 125

Arg Arg Ala Glu Glu Gly Ser His Val Val Leu Arg Trp Leu Pro Pro
            130                 135                 140

Pro Gly Ala Pro Met Thr Thr His Ile Arg Tyr Glu Val Asp Val Ser
145                 150                 155                 160

Ala Gly Asn Arg Ala Gly Gly Thr Gln Arg Val Glu Val Leu Glu Gly
                165                 170                 175

Arg Thr Glu Cys Val Leu Ser Asn Leu Arg Gly Gly Thr Arg Tyr Thr
                180                 185                 190

Phe Ala Val Arg Ala Arg Met Ala Glu Pro Ser Phe Ser Gly Phe Trp
            195                 200                 205

Ser Ala Trp Ser Glu Pro Ala Ser Leu Leu Thr Ala Ser Asp Leu Asp
210                 215                 220

Pro Leu Ile Leu Thr Leu Ser Leu Ile Leu Val Leu Ile Ser Leu Leu
225                 230                 235                 240

Leu Thr Val Leu Ala Leu Leu Ser His Arg Arg Ala Leu Arg Gln Lys
                245                 250                 255

Ile Trp Pro Gly Ile Pro Ser Pro Glu Asn Glu Phe Glu Gly Leu Phe
                260                 265                 270

Thr Thr His Lys Gly Asn Phe Gln Leu Trp Leu Leu Gln Arg Asp Gly
            275                 280                 285

Cys Leu Trp Trp Ser Pro Ser Ser Pro Phe Pro Glu Asp Pro Pro Ala
290                 295                 300

His Leu Glu Val Leu Ser Glu Arg His Trp Gly Val Thr Gln Ala Gly
305                 310                 315                 320

Asp Ala Gly Ala Glu Asp Lys Gly Pro Leu Leu Glu Pro Val Gly Ser
                325                 330                 335

Glu Arg Ala Gln Asp Thr Tyr Leu Val Leu Asp Glu Trp Leu Leu Pro
            340                 345                 350

Arg Cys Pro Cys Ser Glu Asn Leu Ser Gly Pro Gly Asp Ser Val Asp
            355                 360                 365

Pro Ala Thr Met Asp Glu Gly Ser Glu Thr Ser Ser Cys Pro Ser Asp
370                 375                 380

Leu Ala Ser Lys Pro Arg Pro Glu Gly Thr Ser Pro Ser Ser Phe Glu
385                 390                 395                 400

Tyr Thr Ile Leu Asp Pro Ser Ser Lys Leu Leu Cys Pro Arg Ala Leu
                405                 410                 415

Pro Pro Glu Leu Pro Pro Thr Pro His Leu Lys Tyr Leu Tyr Leu
            420                 425                 430

Val Val Ser Asp Ser Gly Ile Ser Thr Asp Tyr Ser Ser Gly Gly Ser
            435                 440                 445

Gln Gly Val His Gly Asp Ser Asp Gly Pro Tyr Ser His Pro Tyr
            450                 455                 460

Glu Asn Ser Leu Val Pro Asp Thr Glu Pro Leu Arg Pro Ser Tyr Val
465                 470                 475                 480

Ala Cys Ser

<210> SEQ ID NO 35
<211> LENGTH: 428
<212> TYPE: PRT
<213> ORGANISM: Rattus norvegicus

<400> SEQUENCE: 35

Ala Ser Ser Pro Ser Leu Pro Asp Pro Lys Phe Glu Ser Lys Ala Ala
1               5                   10                  15

```
Leu Leu Ala Ser Arg Gly Ser Glu Glu Leu Cys Phe Thr Gln Arg
         20                  25                  30

Leu Glu Asp Leu Val Cys Phe Trp Glu Glu Ala Ala Asn Ser Gly Met
             35                  40                  45

Gly Phe Asn Tyr Ser Phe Ser Tyr Gln Leu Glu Gly Glu Ser Arg Lys
         50                  55                  60

Ser Cys Arg Leu His Gln Ala Pro Thr Val Arg Gly Ser Met Arg Phe
 65                  70                  75                  80

Trp Cys Ser Leu Pro Thr Ala Asp Thr Ser Ser Phe Val Pro Leu Glu
                 85                  90                  95

Leu Gln Val Thr Glu Ala Ser Gly Ser Pro Arg Tyr His Arg Ile Ile
                100                 105                 110

His Ile Asn Glu Val Val Leu Leu Asp Ala Pro Ala Gly Leu Leu Ala
            115                 120                 125

Arg Arg Ala Glu Glu Gly Ser His Val Val Leu Arg Trp Leu Pro Pro
130                 135                 140

Pro Gly Ala Pro Met Thr Thr His Ile Arg Tyr Glu Val Asp Val Ser
145                 150                 155                 160

Ala Gly Asn Arg Ala Gly Gly Thr Gln Arg Val Glu Val Leu Glu Gly
                165                 170                 175

Arg Thr Glu Cys Val Leu Ser Asn Leu Arg Gly Gly Thr Arg Tyr Thr
            180                 185                 190

Phe Ala Val Arg Ala Arg Met Ala Glu Pro Ser Phe Ser Gly Phe Trp
        195                 200                 205

Ser Ala Trp Ser Glu Pro Ala Ser Leu Leu Thr Ala Ser Asp Leu Asp
        210                 215                 220

Pro Leu Ile Leu Thr Leu Ser Leu Ile Leu Val Leu Ile Ser Leu Leu
225                 230                 235                 240

Leu Thr Val Leu Ala Leu Leu Ser His Arg Arg Ala Leu Arg Gln Lys
                245                 250                 255

Ile Trp Pro Gly Ile Pro Ser Pro Glu Asn Glu Phe Glu Gly Leu Phe
                260                 265                 270

Thr Thr His Lys Gly Asn Phe Gln Leu Trp Leu Leu Gln Arg Asp Gly
            275                 280                 285

Cys Leu Trp Trp Ser Pro Ser Ser Pro Phe Pro Glu Asp Pro Pro Ala
290                 295                 300

His Leu Glu Val Leu Ser Glu Arg His Trp Gly Val Thr Gln Ala Gly
305                 310                 315                 320

Asp Ala Gly Ala Glu Asp Lys Gly Pro Leu Leu Glu Pro Val Gly Ser
                325                 330                 335

Glu Arg Ala Gln Asp Thr Tyr Leu Val Leu Asp Glu Trp Leu Leu Pro
            340                 345                 350

Arg Cys Pro Cys Ser Glu Asn Leu Ser Gly Pro Gly Asp Ser Val Asp
        355                 360                 365

Pro Ala Thr Met Asp Glu Gly Ser Glu Thr Ser Ser Cys Pro Ser Asp
        370                 375                 380

Leu Ala Ser Lys Pro Arg Pro Glu Gly Thr Ser Pro Ser Ser Phe Glu
385                 390                 395                 400

Tyr Thr Ile Leu Asp Pro Ser Ser Lys Leu Leu Cys Pro Arg Ala Leu
                405                 410                 415

Pro Pro Glu Leu Pro Pro Thr Pro Pro His Leu Lys
            420                 425
```

<210> SEQ ID NO 36
<211> LENGTH: 400
<212> TYPE: PRT
<213> ORGANISM: Rattus norvegicus

<400> SEQUENCE: 36

```
Ala Ser Ser Pro Ser Leu Pro Asp Pro Lys Phe Glu Ser Lys Ala Ala
1               5                   10                  15

Leu Leu Ala Ser Arg Gly Ser Glu Glu Leu Leu Cys Phe Thr Gln Arg
            20                  25                  30

Leu Glu Asp Leu Val Cys Phe Trp Glu Glu Ala Ala Asn Ser Gly Met
        35                  40                  45

Gly Phe Asn Tyr Ser Phe Ser Tyr Gln Leu Glu Gly Glu Ser Arg Lys
    50                  55                  60

Ser Cys Arg Leu His Gln Ala Pro Thr Val Arg Gly Ser Met Arg Phe
65                  70                  75                  80

Trp Cys Ser Leu Pro Thr Ala Asp Thr Ser Ser Phe Val Pro Leu Glu
                85                  90                  95

Leu Gln Val Thr Glu Ala Ser Gly Ser Pro Arg Tyr His Arg Ile Ile
            100                 105                 110

His Ile Asn Glu Val Val Leu Leu Asp Ala Pro Ala Gly Leu Leu Ala
        115                 120                 125

Arg Arg Ala Glu Glu Gly Ser His Val Val Leu Arg Trp Leu Pro Pro
130                 135                 140

Pro Gly Ala Pro Met Thr Thr His Ile Arg Tyr Glu Val Asp Val Ser
145                 150                 155                 160

Ala Gly Asn Arg Ala Gly Gly Thr Gln Arg Val Glu Val Leu Glu Gly
                165                 170                 175

Arg Thr Glu Cys Val Leu Ser Asn Leu Arg Gly Gly Thr Arg Tyr Thr
            180                 185                 190

Phe Ala Val Arg Ala Arg Met Ala Glu Pro Ser Phe Ser Gly Phe Trp
        195                 200                 205

Ser Ala Trp Ser Glu Pro Ala Ser Leu Leu Thr Ala Ser Asp Leu Asp
    210                 215                 220

Pro Leu Ile Leu Thr Leu Ser Leu Ile Leu Val Leu Ile Ser Leu Leu
225                 230                 235                 240

Leu Thr Val Leu Ala Leu Leu Ser His Arg Arg Ala Leu Arg Gln Lys
                245                 250                 255

Ile Trp Pro Gly Ile Pro Ser Pro Glu Asn Glu Phe Glu Gly Leu Phe
            260                 265                 270

Thr Thr His Lys Gly Asn Phe Gln Leu Trp Leu Leu Gln Arg Asp Gly
        275                 280                 285

Cys Leu Trp Trp Ser Pro Ser Ser Pro Phe Pro Glu Asp Pro Pro Ala
    290                 295                 300

His Leu Glu Val Leu Ser Glu Arg His Trp Gly Val Thr Gln Ala Gly
305                 310                 315                 320

Asp Ala Gly Ala Glu Asp Lys Gly Pro Leu Leu Glu Pro Val Gly Ser
                325                 330                 335

Glu Arg Ala Gln Asp Thr Tyr Leu Val Leu Asp Glu Trp Leu Leu Pro
            340                 345                 350

Arg Cys Pro Cys Ser Glu Asn Leu Ser Gly Pro Gly Asp Ser Val Asp
        355                 360                 365

Pro Ala Thr Met Asp Glu Gly Ser Glu Thr Ser Ser Cys Pro Ser Asp
    370                 375                 380
```

```
Leu Ala Ser Lys Pro Arg Pro Glu Gly Thr Ser Pro Ser Ser Phe Glu
385                 390                 395                 400

<210> SEQ ID NO 37
<211> LENGTH: 61
<212> TYPE: DNA
<213> ORGANISM: Gallus gallus

<400> SEQUENCE: 37
atcgatttgc tgccccctag cggggagggg acgtaattac atccctgggt ctagacagct    60
g                                                                   61

<210> SEQ ID NO 38
<211> LENGTH: 42
<212> TYPE: DNA
<213> ORGANISM: Gallus gallus

<400> SEQUENCE: 38
tgctgccccc tagcggggga gggacgtaat tacatccctg gg                       42
```